United States Patent
Boehme et al.

(10) Patent No.: US 8,846,666 B2
(45) Date of Patent: Sep. 30, 2014

(54) OXATHIAZINE DERIVATIVES WHICH ARE SUBSTITUTED WITH BENZYL OR HETEROMETHYLENE GROUPS, METHOD FOR PRODUCING THEM, THEIR USE AS MEDICINE AND DRUG CONTAINING SAID DERIVATIVES AND THE USE THEREOF

(75) Inventors: Thomas Boehme, Frankfurt am Main (DE); Christian Engel, Frankfurt am Main (DE); Stefan Guessregen, Frankfurt am Main (DE); Torsten Haack, Frankfurt am Main (DE); Kurt Ritter, Frankfurt am Main (DE); Georg Tschank, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/003,392

(22) PCT Filed: Mar. 7, 2012

(86) PCT No.: PCT/EP2012/053941
§ 371 (c)(1),
(2), (4) Date: Sep. 5, 2013

(87) PCT Pub. No.: WO2012/120058
PCT Pub. Date: Sep. 13, 2012

(65) Prior Publication Data
US 2014/0066437 A1 Mar. 6, 2014

(30) Foreign Application Priority Data
Mar. 8, 2011 (EP) .................................. 11305246

(51) Int. Cl.
*C07D 291/06* (2006.01)
*C07D 419/14* (2006.01)
*C07D 419/10* (2006.01)
*A61K 31/54* (2006.01)

(52) U.S. Cl.
USPC ............................................ 514/222.5; 544/2

(58) Field of Classification Search
CPC .. C07D 291/06; C07D 419/10; C07D 419/14; A61K 31/54
USPC .......................................... 544/2; 514/222.5
See application file for complete search history.

(56) References Cited

FOREIGN PATENT DOCUMENTS

JP 60-214743 A 10/1985

OTHER PUBLICATIONS

Seigo Suzue et al., Studies on Hypoglycemic Agents. IV. 1) Synthesis of 1,4,3-Benzoxathiazine-4,4-dioxides, Chemical and Pharmaceutical Bulletin, (May 25, 1968), vol. 16, No. 5, pp. 806-813.
International Search Report dated Jul. 9, 2012 issued in PCT/EP2012/053941.

*Primary Examiner* — Kahsay Habte
(74) *Attorney, Agent, or Firm* — Scully, Scott, Murphy & Presser, P.C.

(57) ABSTRACT

The invention relates to the compounds of formula (I) and to the physiologically acceptable salts thereof. Said compounds are suitable for the treatment of hyperglycemia.

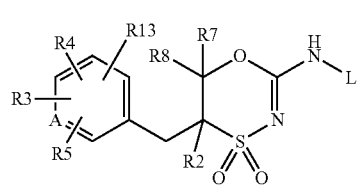

13 Claims, No Drawings

OXATHIAZINE DERIVATIVES WHICH ARE SUBSTITUTED WITH BENZYL OR HETEROMETHYLENE GROUPS, METHOD FOR PRODUCING THEM, THEIR USE AS MEDICINE AND DRUG CONTAINING SAID DERIVATIVES AND THE USE THEREOF

Oxathiazine derivatives which are substituted with benzyl or heteromethylene groups, method for producing them, their use as medicine and drug containing said derivatives and the use thereof.

The invention relates to substituted oxathiazine derivatives and to the physiologically compatible salts thereof.

It was an object of the invention to provide compounds which display a therapeutically utilizable action. More particularly, it was a further object to find novel compounds suitable for treatment of diabetes, hyperglycemia, insulin resistance, obesity or lipid metabolism disorders.

The invention therefore relates to compounds of the formula I

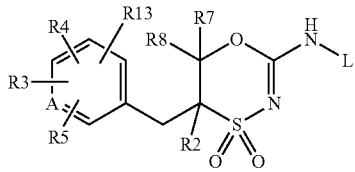

in which

A is CH, N;

L is R1, —CH(R10)(R11);

R10, R11 are each independently H, F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, $NH(C_1-C_6)$-alkyl, $N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$, $(C_1-C_6)$-alkylene-(R6), $(C_3-C_8)$-cycloalkylene-(R6), $(C_1-C_6)$-alkylene-$(C_3-C_8)$-cycloalkylene-(R6), $(C_6-C_{10})$-aryl, $(C_1-C_6)$-alkylene-$(C_6-C_{10})$-aryl, —$(C_6-C_{10})$-heteroaryl, $(C_1-C_6)$-alkylene-$(C_6-C_{10})$-heteroaryl;

where the aryl radical or heteroaryl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$;

R6 is H, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, O—(CO)—$NH_2$, $SF_5$;

R1 is

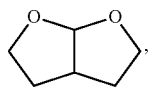

$(C_6-C_{10})$-aryl, $(C_3-C_8)$-cycloalkyl, $(C_3-C_8)$-carbocyclyl, where the

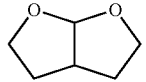

radical, aryl radical, cycloalkyl radical or carbocyclyl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$;

R2 is H, F, $(C_1-C_3)$-alkyl, where the alkyl radical may be mono- to trisubstituted by fluorine;

R3, R4, R5, R13 are each independently

H, F, Cl, Br, I, OH, $CF_3$, $CHF_2$, $CH_2F$, $NO_2$, CN, $OCF_3$, $OCHF_2$, —$(C_1-C_6)$-alkylene-(R9), O—$(C_1-C_6)$-alkylene-(R9), tert-butyl, isopropylene-(R9), (C=O)—$(C_1-C_6)$-alkylene-(R9), $(C_1-C_6)$-alkylene-(R9), $NH_2$, $NH(C_1-C_6)$-alkylene-(R9), $N((C_1-C_6)$-alkylene-R9$)_2$, $(C_1-C_6)$-alkylene-$NH_2$, $(C_1-C_6)$-alkylene-$NH(C_1-C_6)$-alkylene-(R9), $(C_1-C_6)$-alkylene-$N((C_{1-C6})$-alkylene-R9$)_2$, —O—$(C_1-C_6)$-alkylene-$NH_2$, —O—$(C_1-C_6)$-alkylene-$NH(C_1-C_6)$-alkylene-(R9), —O—$(C_1-C_6)$-alkylene-$N((C_1-C_6)$-alkylene-R9$)_2$, —NH—$(C_1-C_6)$-alkylene-$NH_2$, —NH—$(C_1-C_6)$-alkylene-$NH(C_1-C_6)$-alkylene-(R9), —NH—$(C_1-C_6)$-alkylene-$N((C_1-C_6)$-alkylene-R9$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$;

$(C_6-C_{10})$-aryl, —$(C_1-C_6)$-alkylene-$(C_6-C_{10})$-aryl, where the aryl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $NH_2$, $NH(C_1-C_6)$-alkyl, $N((C_1-C_6)$-alkyl$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$, $(C_6-C_{10})$-aryl, $(C_3-C_8)$-cycloalkyl, 4 to 12-membered heterocycle;

where the $(C_6-C_{10})$-aryl radical, $(C_3-C_8)$-cycloalkyl radical, 4 to 12-membered heterocycle radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$;

4 to 12-membered heterocycle, —$(C_1-C_6)$-alkylene-4 to 12-membered heterocycle, where the heterocyclyl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkylene-(R9), $(C_1-C_6)$-alkylene-(R9), $NH_2$, $NH(C_1-C_6)$-alkylene-(R9), $N((C_1-C_6)$-alkyl$)_2$, $SO_2$—$(C_1-C_6)$-alkylene-(R9), $SO_2$—$C_2H_2F_3$, $SO_2$—$CH_3$, $SO_2$—$NH_2$, $SO_2$—$NH(C_1-C_6)$-alkylene-(R9), $SO_2$—$N((C_1-C_6)$-alkyl$)_2$, COOH, COO—$(C_1-C_6)$-alkylene-(R9), $CONH_2$, $CONH(C_1-C_6)$-alkylene-(R9), $CON((C_1-C_6)$-alkyl$)_2$, $SF_5$, $(C_6-C_{10})$-aryl, $(C_3-C_8)$-cycloalkyl, 4 to 12-membered heterocycle;

where the $(C_6-C_{10})$-aryl radical, $(C_3-C_8)$-cycloalkyl radical, 4 to 12-membered heterocycle radical may be mono- to trisubstituted by F, Cl, Br, I, OH, $CF_3$, CHF$_2$, CH$_2$F, NO$_2$, CN, OCF$_3$, OCHF$_2$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, SO$_2$—NH$_2$, SO$_2$—NH(C$_1$-C$_6$)-alkyl, SO$_2$—N((C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-alkyl)$_2$, SF$_5$;

or R4 and R5 together form a —CH=CH—CH=CH— chain;

R7, R8 are each independently H, mono- or poly-fluorine-substituted (C$_1$-C$_3$)-alkyl, or R7 and R8 together with the carbon atom to which they are bonded form a 3-8-membered carbocycle or heterocycle;

R9 is H, OH, OCH$_3$, OCF$_3$, CHF$_2$, CF$_3$;

and pharmaceutically acceptable salts thereof.

Preference is given to compounds of the formula I in which

A is CH, N;

L is R1, —CH(R10)(R11);

R10, R11 are each independently H, F, Cl, Br, I, OH, CF$_3$, CHF$_2$, CH$_2$F, NO$_2$, CN, OCF$_3$, OCHF$_2$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-alkyl)$_2$, SF$_5$, (C$_1$-C$_6$)-alkylene-(R6), (C$_3$-C$_8$)-cycloalkylene-(R6), (C$_1$-C$_6$)-alkylene-(C$_3$-C$_8$)-cycloalkylene-(R6), (C$_6$-C$_{10}$)-aryl, (C$_1$-C$_6$)-alkylene-(C$_6$-C$_{10}$)-aryl, —(C$_6$-C$_{10}$)-heteroaryl, (C$_1$-C$_6$)-alkylene-(C$_6$-C$_{10}$)-heteroaryl;

where the aryl radical or heteroaryl radical may be mono- to trisubstituted by F, Cl, Br, I, OH, CF$_3$, CHF$_2$, CH$_2$F, NO$_2$, CN, OCF$_3$, OCHF$_2$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, SO$_2$—NH$_2$, SO$_2$—NH(C$_1$-C$_6$)-alkyl, SO$_2$—N((C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-alkyl)$_2$, SF$_5$;

R6 is H, OH, CF$_3$, CHF$_2$, CH$_2$F, NO$_2$, CN, OCF$_3$, OCHF$_2$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, SO$_2$—NH$_2$, SO$_2$—NH(C$_1$-C$_6$)-alkyl, SO$_2$—N((C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-alkyl)$_2$, O—(CO)—NH$_2$, SF$_5$;

R1 is (C$_6$-C$_{10}$)-aryl, (C$_3$-C$_8$)-cycloalkyl, (C$_3$-C$_8$)-carbocyclyl, where the aryl radical, cycloalkyl radical or carbocyclyl radical may be mono- to trisubstituted by F, Cl, Br, I, OH, CF$_3$, CHF$_2$, CH$_2$F, NO$_2$, CN, OCF$_3$, OCHF$_2$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, SO$_2$—NH$_2$, SO$_2$—NH(C$_1$-C$_6$)-alkyl, SO$_2$—N((C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-alkyl)$_2$, SF$_5$;

R2 is H, F, (C$_1$-C$_3$)-alkyl, where the alkyl radical may be mono- to trisubstituted by fluorine;

R3, R4, R5, R13 are each independently

H, F, Cl, Br, I, OH, CF$_3$, CHF$_2$, CH$_2$F, NO$_2$, CN, OCF$_3$, OCHF$_2$, —(C$_1$-C$_6$)-alkylene-(R9), O—(C$_1$-C$_6$)-alkylene-(R9), tert-butyl, isopropylene-(R9), (C=O)—(C$_1$-C$_6$)-alkylene-(R9), (C$_1$-C$_6$)-alkylene-(R9), NH$_2$, NH(C$_1$-C$_6$)-alkylene-(R9), N((C$_1$-C$_6$)-alkylene-R9)$_2$, (C$_1$-C$_6$)-alkylene-NH$_2$, (C$_1$-C$_6$)-alkylene-NH(C$_1$-C$_6$)-alkylene-(R9), (C$_1$-C$_6$)-alkylene-N((C$_1$-C$_6$)-alkylene-R9)$_2$, —O—(C$_1$-C$_6$)-alkylene-NH$_2$, H$_2$, —O—(C$_1$-C$_6$)-alkylene-NH(C$_1$-C$_6$)-alkylene-(R9), —O—(C$_1$-C$_6$)-alkylene-N((C$_1$-C$_6$)-alkylene-R9)$_2$, —NH—(C$_1$-C$_6$)-alkylene-NH$_2$, —NH—(C$_1$-C$_6$)-alkylene-NH(C$_1$-C$_6$)-alkylene-(R9), —NH—(C$_1$-C$_6$)-alkylene-N((C$_1$-C$_6$)-alkylene-R9)$_2$, SO$_2$—CH$_3$, SO$_2$—NH$_2$, SO$_2$—NH (C$_1$-C$_6$)-alkyl, SO$_2$—N((C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-alkyl)$_2$, SF$_5$;

phenyl, where the phenyl radical may be mono- to trisubstituted by F, Cl, Br, I, OH, CF$_3$, CHF$_2$, CH$_2$F, NO$_2$, CN, OCF$_3$, OCHF$_2$, (C$_1$-C$_6$)-alkyl, NH$_2$, NH(C$_1$-C$_6$)-alkyl, N((C$_1$-C$_6$)-alkyl)$_2$, SO$_2$—CH$_3$, SO$_2$—NH$_2$, SO$_2$—NH(C$_1$-C$_6$)-alkyl, SO$_2$—N((C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-alkyl)$_2$, SF$_5$, (C$_6$-C$_{10}$)-aryl, (C$_3$-C$_8$)-cycloalkyl, 4 to 12-membered heterocycle;

where the (C$_6$-C$_{10}$)-aryl radical, (C$_3$-C$_8$)-cycloalkyl radical, 4 to 12-membered heterocycle radical may be mono- to trisubstituted by F, Cl, Br, I, OH, CF$_3$, CHF$_2$, CH$_2$F, NO$_2$, CN, OCF$_3$, OCHF$_2$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, SO$_2$—NH$_2$, SO$_2$—NH(C$_1$-C$_6$)-alkyl, SO$_2$—N((C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-alkyl)$_2$, SF$_5$;

4 to 12-membered heterocycle, —(C$_1$-C$_6$)-alkylene-4 to 12-membered heterocycle, where the heterocyclyl radical may be mono- to trisubstituted by F, Cl, Br, I, OH, CF$_3$, CHF$_2$, CH$_2$F, NO$_2$, CN, OCF$_3$, OCHF$_2$, O—(C$_1$-C$_6$)-alkylene-(R9), (C$_1$-C$_6$)-alkylene-(R9), NH$_2$, NH(C$_1$-C$_6$)-alkylene-(R9), N((C$_1$-C$_6$)-alkyl)$_2$, SO$_2$—(C$_1$-C$_6$)-alkylene-(R9), SO$_2$—C$_2$H$_2$F$_3$, SO$_2$—CH$_3$, SO$_2$—NH$_2$, SO$_2$—NH(C$_1$-C$_6$)-alkylene-(R9), SO$_2$—N((C$_1$-C$_6$)-alkyl)$_2$, COOH, COO—(C$_1$-C$_6$)-alkylene-(R9), CONH$_2$, CONH(C$_1$-C$_6$)-alkylene-(R9), CON((C$_1$-C$_6$)-alkyl)$_2$, SF$_5$, (C$_6$-C$_{10}$)-aryl, (C$_3$-C$_8$)-cycloalkyl, 4 to 12-membered heterocycle;

where the (C$_6$-C$_{10}$)-aryl radical, (C$_3$-C$_8$)-cycloalkyl radical, 4 to 12-membered heterocycle radical may be mono- to trisubstituted by F, Cl, Br, I, OH, CF$_3$, CHF$_2$, CH$_2$F, NO$_2$, CN, OCF$_3$, OCHF$_2$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, SO$_2$—NH$_2$, SO$_2$—NH(C$_1$-C$_6$)-alkyl, SO$_2$—N((C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-alkyl)$_2$, SF$_5$;

or R4 and R5 together form a —CH=CH—CH=CH— chain;

R7, R8 are each independently (C$_1$-C$_3$)-alkyl;

R9 is H, OH, OCH$_3$, OCF$_3$, CHF$_2$, CF$_3$;

and pharmaceutically acceptable salts thereof.

Preference is further given to compounds of the formula I in which

A is CH, N;

L is R1, —CH(R10)(R11);

R10, R11 are each independently (C$_1$-C$_6$)-alkyl, (C$_1$-C$_6$)-alkylene-(R6), (C$_6$-C$_{10}$)-aryl, —(C$_6$-C$_{10}$)-heteroaryl;

where the aryl radical or heteroaryl radical may be mono- to trisubstituted by F, Cl, Br, I, OH, CF$_3$, CHF$_2$, CH$_2$F, NO$_2$, CN, OCF$_3$, OCHF$_2$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, SO$_2$—NH$_2$, SO$_2$—NH(C$_1$-C$_6$)-alkyl, SO$_2$—N((C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-allyl)$_2$, SF$_5$;

R6 is H, OH, O—(CO)—NH$_2$, SO$_2$NH$_2$;

R1 is (C$_3$-C$_8$)-cycloalkyl, (C$_3$-C$_8$)-carbocyclyl, where the cycloalkyl radical or carbocyclyl radical may be mono- to trisubstituted by F, Cl, Br, I, OH, CF$_3$, CHF$_2$, CH$_2$F, NO$_2$, CN, OCF$_3$, OCHF$_2$, O—(C$_1$-C$_6$)-alkyl, ($C_1$-$C_6$)-alkyl, $NH_2$, $NH(C_1$-$C_6)$-alkyl, $N((C_1$-$C_6)$-alkyl)$_2$, $SO_2$—$CH_3$, $SO_2$—$NH_2$, $SO_2$—$NH(C_1$-$C_6)$-alkyl, $SO_2$—$N((C_1$-$C_6)$-alkyl)$_2$, COOH, COO—($C_1$-$C_6$)-alkyl, $CONH_2$, $CONH(C_1$-$C_6)$-alkyl, $CON((C_1$-$C_6)$-alkyl)$_2$, $SF_5$;

R2 is H, F, ($C_1$-$C_3$)-alkyl, where the alkyl radical may be mono- to trisubstituted by fluorine;

R3 is F, Cl, Br, I, OH, $CF_3$, $CHF_2$, $CH_2F$, $NO_2$, CN, $OCF_3$, $OCHF_2$, —($C_1$-$C_6$)-alkylene-(R9), O—($C_1$-$C_6$)-alkylene-(R9), tert-butyl, isopropylene-(R9), (C═O)—($C_1$-$C_6$)-alkylene-(R9), ($C_1$-$C_6$)-alkylene-(R9), $NH_2$, $NH(C_1$-$C_6)$-alkylene-(R9), $N((C_1$-$C_6)$-alkylene-R9)$_2$, ($C_1$-$C_6$)-alkylene-$NH_2$, ($C_1$-$C_6$)-alkylene-$NH(C_1$-$C_6)$-alkylene-(R9), ($C_1$-$C_6$)-alkylene-$N((C_1$-$C_6)$-alkylene-R9)$_2$, —O—($C_1$-$C_6$)-alkylene-$NH_2$, —O—($C_1$-$C_6$)-alkylene-$NH(C_1$-$C_6)$-alkylene-(R9), —O—($C_1$-$C_6$)-alkylene-$N((C_1$-$C_6)$-alkylene-R9)$_2$, —NH—($C_1$-$C_6$)-alkylene-$NH_2$, —NH—($C_1$-$C_6$)-alkylene-$NH(C_1$-$C_6)$-alkylene-(R9), —NH—($C_1$-$C_6$)-alkylene-$N((C_1$-$C_6)$-alkylene-R9)$_2$, $SO_2$—$CH_3$, $SO_2$—$NH_2$, $SO_2$—$NH(C_1$-$C_6)$-alkyl, $SO_2$—$N((C_1$-$C_6)$-alkyl)$_2$, COOH, COO—($C_1$-$C_6$)-alkyl, $CONH_2$, $CONH(C_1$-$C_6)$-alkyl, $CON((C_1$-$C_6)$-alkyl)$_2$, $SF_5$;

phenyl,
where the phenyl radical may be mono- to trisubstituted by F, Cl, Br, I, OH, $CF_3$, $CHF_2$, $CH_2F$, $NO_2$, CN, $OCF_3$, ($C_1$-$C_6$)-alkyl, $NH_2$, $NH(C_1$-$C_6)$-alkyl, $N((C_1$-$C_6)$-alkyl)$_2$, $SO_2$—$CH_3$, $SO_2$—$NH_2$, $SO_2$—$NH(C_1$-$C_6)$-alkyl, $SO_2$—$N((C_1$-$C_6)$-alkyl)$_2$, COOH, COO—($C_1$-$C_6$)-alkyl, $CONH_2$, $CONH(C_1$-$C_6)$-alkyl, $CON((C_1$-$C_6)$-alkyl)$_2$, $SF_5$, ($C_6$-$C_{10}$)-aryl, ($C_3$-$C_8$)-cycloalkyl, 4 to 12-membered heterocycle;
where the ($C_6$-$C_{10}$)-aryl radical, ($C_3$-$C_8$)-cycloalkyl radical, 4 to 12-membered heterocycle radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SO_2$—$CH_3$, $SO_2$—$NH_2$, $SO_2$—$NH(C_1$-$C_6)$-alkyl, $SO_2$—$N((C_1$-$C_6)$-alkyl)$_2$, COOH, COO—($C_1$-$C_6$)-alkyl, $CONH_2$, $CONH(C_1$-$C_6)$-alkyl, $CON((C_1$-$C_6)$-alkyl)$_2$, $SF_5$;

4 to 12-membered heterocycle, —($C_1$-$C_6$)-alkylene-4 to 12-membered heterocycle,
where the heterocyclyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkylene-(R9), ($C_1$-$C_6$)-alkylene-(R9), $NH_2$, $NH(C_1$-$C_6)$-alkylene-(R9), $N((C_1$-$C_6)$-alkyl)$_2$, $SO_2$—($C_1$-$C_6$)-alkylene-(R9), $SO_2$—$C_2H_2F_3$, $SO_2$—$CH_3$, $SO_2$—$NH_2$, $SO_2$—$NH(C_1$-$C_6)$-alkylene-(R9), $SO_2$—$N((C_1$-$C_6)$-alkyl)$_2$, COOH, COO—($C_1$-$C_6$)-alkylene-(R9), $CONH_2$, $CONH(C_1$-$C_6)$-alkylene-(R9), $CON((C_1$-$C_6)$-alkyl)$_2$, $SF_5$, ($C_6$-$C_{10}$)-aryl, ($C_3$-$C_8$)-cycloalkyl, 4 to 12-membered heterocycle;
where the ($C_6$-$C_{10}$)-aryl radical, ($C_3$-$C_8$)-cycloalkyl radical, 4 to 12-membered heterocycle radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SO_2$—$CH_3$, $SO_2$—$NH_2$, $SO_2$—$NH(C_1$-$C_6)$-alkyl, $SO_2$—$N((C_1$-$C_6)$-alkyl)$_2$, COOH, COO—($C_1$-$C_6$)-alkyl, $CONH_2$, $CONH(C_1$-$C_6)$-alkyl, $CON((C_1$-$C_6)$-alkyl)$_2$, $SF_5$;

R4, R5, R13 are each independently
H, F, Cl, Br, I, OH, $CF_3$, $NO_2$, CN, $OCF_3$, —($C_1$-$C_6$)-alkylene-(R9), O—($C_1$-$C_6$)-alkylene-(R9), $NH_2$;

R7, R8 are each independently ($C_1$-$C_3$)-alkyl;

R9 is H, OH, $OCH_3$, $OCF_3$, $CHF_2$, $CF_3$;

and pharmaceutically acceptable salts thereof.

Preference is further given to compounds of the formula I in which

A is CH, N;

L is R1, —CH(R10)(R11);

R10 is ($C_1$-$C_6$)-alkyl, ($C_1$-$C_6$)-alkylene-(R6);

R11 is ($C_6$-$C_{10}$)-aryl;
where the aryl radical or heteroaryl radical may be mono- to trisubstituted by F, Cl, Br, ($C_1$-$C_6$)-alkyl;

R6 is OH;

R1 is 2,2,2-bicyclooctyl,
where the 2,2,2-bicyclooctyl radical may be mono- to trisubstituted by F, Cl, Br;

R2 is H, ($C_1$-$C_3$)-alkyl;

R3 is F, Cl, Br, I, OH, $CF_3$, $CHF_2$, $CH_2F$, $NO_2$, CN, $OCF_3$, $OCHF_2$, —($C_1$-$C_6$)-alkylene-(R9), O—($C_1$-$C_6$)-alkylene-(R9), tert-butyl, isopropylene-(R9), (C═O)—($C_1$-$C_6$)-alkylene-(R9), ($C_1$-$C_6$)-alkylene-(R9), $NH_2$, $NH(C_1$-$C_6)$-alkylene-(R9), $N((C_1$-$C_6)$-alkylene-R9)$_2$, ($C_1$-$C_6$)-alkylene-$NH_2$, ($C_1$-$C_6$)-alkylene-$NH(C_1$-$C_6)$-alkylene-(R9), ($C_1$-$C_6$)-alkylene-$N((C_1$-$C_6)$-alkylene-R9)$_2$, —O—($C_1$-$C_6$)-alkylene-$NH_2$, —O—($C_1$-$C_6$)-alkylene-$NH(C_1$-$C_6)$-alkylene-(R9), —O—($C_1$-$C_6$)-alkylene-$N((C_1$-$C_6)$-alkylene-R9)$_2$, —NH—($C_1$-$C_6$)-alkylene-$NH_2$, —NH—($C_1$-$C_6$)-alkylene-$NH(C_1$-$C_6)$-alkylene-(R9), —NH—($C_1$-$C_6$)-alkylene-$N((C_1$-$C_6)$-alkylene-R9)$_2$, $SO_2$—$CH_3$, $SO_2$—$NH_2$, $SO_2$—$NH(C_1$-$C_6)$-alkyl, $SO_2$—$N((C_1$-$C_6)$-alkyl)$_2$, COOH, COO—($C_1$-$C_6$)-alkyl, $CONH_2$, $CONH(C_1$-$C_6)$-alkyl, $CON((C_1$-$C_6)$-alkyl)$_2$, $SF_5$;

phenyl,
where the phenyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SO_2$—$CH_3$, $SO_2$—$NH_2$, $SO_2$—$NH(C_1$-$C_6)$-alkyl, $SO_2$—$N((C_1$-$C_6)$-alkyl)$_2$, COOH, COO—($C_1$-$C_6$)-alkyl, $CONH_2$, $CONH(C_1$-$C_6)$-alkyl, $CON((C_1$-$C_6)$-alkyl)$_2$, $SF_5$;

pyridine, tetrahydropyridine, piperidine, morpholine, piperazine,
where the pyridine, tetrahydropyridine, piperidine, morpholine or piperazine radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkylene-(R9), ($C_1$-$C_6$)-alkylene-(R9), $NH_2$, $NH(C_1$-$C_6)$-alkylene-(R9), $N((C_1$-$C_6)$-alkyl)$_2$, $SO_2$—($C_1$-$C_6$)-alkylene-(R9), $SO_2$—$C_2H_2F_3$, $SO_2$—$CH_3$, $SO_2$—$NH_2$, $SO_2$—$NH(C_1$-$C_6)$-alkylene-(R9), $SO_2$—$N((C_1$-$C_6)$-alkyl)$_2$, COOH, COO—($C_1$-$C_6$)-alkylene-(R9), $CONH_2$, $CONH(C_1$-$C_6)$-alkylene-(R9), $CON((C_1$-$C_6)$-alkyl)$_2$, $SF_5$ ($C_6$-$C_{10}$)-aryl, ($C_3$-$C_8$)-cycloalkyl, —($C_1$-$C_6$)-alkylene-($C_3$-$C_8$)-cycloalkyl, 4 to 12-membered heterocycle;

R4, R5, R13 are each independently
H, F, Cl, Br, I, OH, $CF_3$, $NO_2$, CN, $OCF_3$, —($C_1$-$C_6$)-alkylene-(R9), O—($C_1$-$C_6$)-alkylene-(R9), $NH_2$;

R7, R8 are each independently ($C_1$-$C_3$)-alkyl;

R9 is H, OH, $OCH_3$, $OCF_3$, $CHF_2$, $CF_3$;

and pharmaceutically acceptable salts thereof.

Preference is further given to compounds of the formula I in which

A is CH, N;

L is R1, —CH(R10)(R11);

R10 is ($C_1$-$C_6$)-alkyl, ($C_1$-$C_6$)-alkylene-(R6);

R11 is ($C_6$-$C_{10}$)-aryl;
where the aryl radical or heteroaryl radical may be mono- to trisubstituted by F, Cl, Br, ($C_1$-$C_6$)-alkyl;

R6 is OH;
R1 is 2,2,2-bicyclooctyl,
  where the 2,2,2-bicyclooctyl radical may be mono- to trisubstituted by F, Cl, Br;
R2 is H, $(C_1$-$C_3)$-alkyl;
R3 is F, Cl, Br, I, OH, $CF_3$, $CHF_2$, $CH_2F$, $NO_2$, CN, $OCF_3$, $OCHF_2$, —$(C_1$-$C_6)$-alkylene-(R9), O—$(C_1$-$C_6)$-alkylene-(R9), tert-butyl, isopropylene-(R9), (C=O)—$(C_1$-$C_6)$-alkylene-(R9), $(C_1$-$C_6)$-alkylene-(R9), $NH_2$, $NH(C_1$-$C_6)$-alkylene-(R9), $N((C_1$-$C_6)$-alkylene-R9$)_2$, $(C_1$-$C_6)$-alkylene-$NH_2$, $(C_1$-$C_6)$-alkylene-$NH(C_1$-$C_6)$-alkylene-(R9), $(C_1$-$C_6)$-alkylene-$N((C_1$-$C_6)$-alkylene-R9$)_2$, —O—$(C_1$-$C_6)$-alkylene-$NH_2$, —O—$(C_1$-$C_6)$-alkylene-$NH(C_1$-$C_6)$-alkylene-(R9), —O—$(C_1$-$C_6)$-alkylene-$N((C_1$-$C_6)$-alkylene-R9$)_2$, —NH—$(C_1$-$C_6)$-alkylene-$NH_2$, —NH—$(C_1$-$C_6)$-alkylene-$NH(C_1$-$C_6)$-alkylene-(R9), —NH—$(C_1$-$C_6)$-alkylene-$N((C_1$-$C_6)$-alkylene-R9$)_2$, $SO_2$—$CH_3$, $SO_2$—$NH_2$, $SO_2$—$NH(C_1$-$C_6)$-alkyl, $SO_2$—$N((C_1$-$C_6)$-alkyl$)_2$, COOH, COO—$(C_1$-$C_6)$-alkyl, $CONH_2$, CONH$(C_1$-$C_6)$-alkyl, CON$((C_1$-$C_6)$-alkyl$)_2$, $SF_5$;
phenyl,
  where the phenyl radical may be mono- to trisubstituted by F, Cl, Br, $CF_3$;
pyridine, tetrahydropyridine, piperidine, morpholine, piperazine,
  where the pyridine, tetrahydropyridine, piperidine, morpholine or piperazine radical may be mono- to trisubstituted by F, Cl, Br, $CF_3$, $(C_1$-$C_6)$-alkylene-(R9), COO—$(C_1$-$C_6)$-alkylene-(R9), $(C_3$-$C_8)$-cycloalkyl, oxetane;
R4, R5, R13 are each independently
  H, F, Cl, Br, I, OH, $CF_3$, $NO_2$, CN, $OCF_3$, —$(C_1$-$C_6)$-alkylene-(R9), O—$(C_1$-$C_6)$-alkylene-(R9), $NH_2$;
R7, R8 are each independently $(C_1$-$C_3)$-alkyl;
R9 is H, OH, $OCH_3$, $OCF_3$, $CHF_2$, $CF_3$;
and pharmaceutically acceptable salts thereof.

In a further embodiment, preference is given to compounds of the formula I having an R3 radical other than H in the para position.

If radicals or substituents can occur more than once in the compounds of the formula I, they may each independently be defined as specified and be the same or different.

If the A radical in the compounds of the formula I is defined as —CH—, the carbon atom in this group may be substituted by R3 or R5.

The invention relates to compounds of the formula I in the form of their tautomers, racemates, racemic mixtures, stereoisomer mixtures, pure stereoisomers, diastereoisomer mixtures and pure diastereoisomers. The mixtures are separated, for example, by a chromatographic route.

Because of their higher water solubility compared to the starting or base compounds, pharmaceutically acceptable salts are particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic acid, phosphoric acid, metaphosphoric acid, nitric acid and sulfuric acid, and of organic acids, for example acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Salts with a pharmaceutically unacceptable anion, for example trifluoroacetate, are likewise within the scope of the invention as useful intermediates for the preparation or purification of pharmaceutically acceptable salts and/or for use in nontherapeutic, for example in vitro, applications.

The inventive compounds may also exist in various polymorphic forms, for example as amorphous and crystalline polymorphic forms. All polymorphic forms of the inventive compounds are within the scope of the invention and are a further aspect of the invention.

All references to "compound(s) of formula I" hereinafter refer to compound(s) of the formula I as described above, and the salts and solvates thereof as described herein.

An alkyl radical is understood to mean a straight-chain or branched hydrocarbon chain having one to eight carbons, for example methyl, ethyl, isopropyl, tert-butyl, hexyl, heptyl, octyl. The alkyl radicals may be mono- or polysubstituted as described above.

An alkylene radical is understood to mean a straight-chain or branched hydrocarbon chain having two free valences, for example methylene, ethylene, isopropylene, tert-butylene.

A carbocycle or carbocyclyl radical is understood to mean a ring in saturated or partially unsaturated form (with one or two double bonds), formed exclusively from carbon atoms.

An aryl radical is understood to mean a phenyl, naphthyl, biphenyl, tetrahydronaphthyl, alpha- or beta-tetralonyl, indanyl or indan-1-onyl radical.

The aryl radicals may be mono- or polysubstituted by suitable groups as described above.

Heterocycle and heterocyclic radical are understood to mean rings and ring systems which, apart from carbon, also contain heteroatoms, for example nitrogen, oxygen or sulfur. In addition, this definition also includes ring systems in which the heterocycle or the heterocyclic radical is fused to a further ring system. The heterocycle or the heterocyclic radical may be saturated, partly saturated or aromatic.

Suitable "heterocycles" or "heterocyclic radicals" are acridinyl, azepanyl, azocinyl, benzimidazolyl, benzofuryl, benzothienyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, 5,6-dihydro-4H-cyclopentathiazol-2-yl, 4,5-dihydrothiazol-2-yl, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, 4,5,6,7-tetrahydrobenzooxazol-2-yl, 4,5,6,7-tetrahydro-benzothiazol-2-yl, 4,5,6,7-tetrahydrobenzoimidazol-2-yl, 4,5,6,7-tetrahydro-pyrazolo[1,5-a]pyridin-2-yl, tetrahydrofuranyl, tetrahydropyranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazinyl, triazolyl, tetrazolyl, thiazolo[4,5-b]pyridinyl, thieno[2,3-d]thiazol-2-yl, tropanyl and xanthenyl.

The heterocycles or heterocyclic radicals may be mono- or polysubstituted by suitable groups as described above.

The compound(s) of the formula I can also be administered in combination with further active ingredients.

The amount of a compound of the formula I required to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of body weight, for example 3-10 mg/kg/day. An intravenous dose may be, for example, in the range from 0.3 mg to 1.0 mg/kg, which can suitably be administered as infusion of 10 ng to 100 ng per kilogram per minute. Suitable infusion solutions for these purposes may contain, for example, 0.1 ng to 10 mg, typically 1 ng to 10 mg, per milliliter. Single doses may contain, for example, 1 mg to 10 g of the active ingredient. Thus, ampoules for injections may contain, for example, from 1 mg to 100 mg, and orally administrable single-dose formulations, for example tablets or capsules, may contain, for example, from 1.0 to 1000 mg, typically from 10 to 600 mg. For treatment of the abovementioned conditions, the compounds of the formula I themselves may be used as the compound, but they are preferably present with a compatible carrier in the form of a pharmaceutical composition. The carrier must of course be acceptable in the sense that it is compatible with the other constituents of the composition and is not harmful to the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Inventive pharmaceutical compositions are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations are also within the scope of the invention. Preference is given to acid- and gastric juice-resistant formulations. Suitable gastric juice-resistant coatings comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units, for example capsules, cachets, lozenges or tablets, each of which contains a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. For example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surfactant(s)/dispersant(s) in a suitable machine. Molded tablets can be produced by molding the pulverulent compound moistened with an inert liquid diluent in a suitable machine.

Pharmaceutical compositions suitable for peroral (sublingual) administration include lozenges which contain a compound of formula I with a flavoring, typically sucrose, and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable inventive compositions generally contain from 0.1 to 5% by weight of the active compound.

Pharmaceutical compositions suitable for rectal administration are preferably in the form of single-dose suppositories. These can be produced by mixing a compound of formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of 0.1 to 15% by weight of the composition, for example 0.5 to 2%.

Transdermal administration is also possible. Pharmaceutical compositions suitable for transdermal uses may be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular option is for the active ingredient to be released by electrotransport or iontophoresis as described, for example, in Pharmaceutical Research, 2(6): 318 (1986).

Further suitable active ingredients for the combination products are:

All antidiabetics mentioned in the Rote Liste 2009, chapter 12; all weight-reducing agents/appetite suppressants mentioned in the Rote Liste 2009, chapter 1; all lipid-lowering agents mentioned in the Rote Liste 2009, chapter 58. They can be combined with the inventive compound of the formula I, especially for a synergistic improvement in action. The active ingredient combination can be administered either by separate administration of the active ingredients to the patient or in the form of combination products in which a plurality of active ingredients are present in one pharmaceutical preparation. Most of the active ingredients mentioned hereinafter are disclosed in the USP Dictionary of USAN and International Drug Names, US Pharmacopeia, Rockville 2001.

Antidiabetics include insulin and insulin derivatives, for example Lantus® (see www.lantus.com) or EIMR 1964 or Levemir® (insulin detemir), or those as described in WO2005005477 (Novo Nordisk), fast-acting insulins (see U.S. Pat. No. 6,221,633), inhalable insulins, for example Exubera®, or oral insulins, for example TN-105 (Nobex) or Oral-lyn™ (Generex Biotechnology), GLP-1 derivatives, for example exenatide, liraglutide or those which have been disclosed in WO 98/08871, WO2005027978, WO2006037811, WO2006037810 to Novo Nordisk A/S, in WO 01/04156 to Zealand or in WO 00/34331 to Beaufour-Ipsen, pramlintide acetate (Symlin; Amylin Pharmaceuticals), and oral hypoglycemic active ingredients.

The orally active hypoglycemic ingredients preferably include sulfonylureas,
biguanidines,
meglitinides,
oxadiazolidinediones,
thiazolidinediones,
glucosidase inhibitors,
inhibitors of glycogen phosphorylase,
glucagon antagonists,
glucokinase activators,
inhibitors of fructose 1,6-bisphosphatase,
modulators of glucose transporter 4 (GLUT4),
inhibitors of glutamine:fructose-6-phosphate amidotransferase (GFAT),
GLP-1 agonists, potassium channel openers, for example those which have been disclosed in WO 97/26265 and WO 99/03861 to Novo Nordisk A/S, or those described in WO2006045799
(Solvay),
inhibitors of dipeptidyl peptidase-IV (DPP-IV),
insulin sensitizers,
inhibitors of liver enzymes involved in stimulating gluconeogenesis and/or glycogenolysis,
modulators of glucose uptake, of glucose transport and of glucose reabsorption,
inhibitors of 11β-HSD1,
inhibitors of protein tyrosine phosphatase-1B (PTP1B),
modulators of sodium-dependent glucose transporter 1 or 2 (SGLT1, SGLT2), compounds which modify the lipid metabolism, such as active antihyperlipidemic ingredients and active antilipidemic ingredients,
compounds which reduce food intake,
compounds which increase thermogenesis,
PPAR and RXR modulators and
active ingredients which act on the ATP-dependent potassium channel of the beta cells.

In one embodiment of the invention, the compound of the formula I is administered in combination with an HMG-CoA reductase inhibitor such as simvastatin, fluvastatin, pravastatin, lovastatin, atorvastatin, cerivastatin, rosuvastatin, L-659699.

In one embodiment of the invention, the compound of the formula I is administered in combination with a cholesterol absorption inhibitor, for example ezetimibe, tiqueside, pamaqueside, FM-VP4 (sitostanol/campesterol ascorbyl phosphate; Forbes Medi-Tech, WO2005042692, WO2005005453), MD-0727 (Microbia Inc., WO2005021497, WO2005021495) or with compounds as described in WO2002066464, (Kotobuki Pharmaceutical Co. Ltd.) or WO2005044256 or WO2005062824 (Merck & Co.) or WO2005061451 and WO2005061452 (AstraZeneca AB) and WO2006017257 (Phenomix) or WO2005033100 (Lipideon Biotechnology AG).

In one embodiment of the invention, the compound of the formula I is administered in combination with Vytorin™, a solid combination of ezetimibe with simvastatin.

In one embodiment of the invention, the compound of the formula I is administered in combination with a solid combination of ezetimibe with fenofibrate.

In a further embodiment of the invention, the compound of the formula I is administered in combination with a solid combination of fenofibrate with rosuvastatin.

In one embodiment of the invention, the compound of the formula I is administered in combination with ISIS-301012, an antisense oligonucleotide which is capable of regulating the apolipoprotein B gene.

In one embodiment of the invention, the compound of the formula I is administered in combination with a PPAR gamma agonist, for example rosiglitazone, pioglitazone, JTT-501, Gl 262570, R-483, CS-011 (rivoglitazone).

In one embodiment of the invention, the compound of the formula I is administered in combination with Competact™, a solid combination of pioglitazone hydrochloride with metformin hydrochloride.

In one embodiment of the invention, the compound of the formula I is administered in combination with Duetact™, a solid combination of pioglitazone hydrochloride with glimepiride.

In one embodiment of the invention, the compound of the formula I is administered in combination with Avandamet®, a solid combination of rosiglitazone maleate with metformin hydrochloride.

In one embodiment of the invention, the compound of the formula I is administered in combination with PPAR alpha agonists, for example GW9578, GW-590735, K-111, LY-674, KRP-101, DRF-10945.

In one embodiment of the invention, the compound of the formula I is administered in combination with a mixed PPAR alpha/gamma agonist, for example naveglitazar, LY-510929, ONO-5129, E-3030, AVE 8042, AVE 8134, AVE 0847, or as described in PCT/US 00/11833, PCT/US 00/11490, DE10142734.4 or in J. P. Berger et al., TRENDS in Pharmacological Sciences 28(5), 244-251, 2005.

In one embodiment of the invention, the compound of the formula I is administered in combination with a PPAR delta agonist, for example GW-501516.

In one embodiment, the compound of the formula I is administered in combination with metaglidasen or with MBX-2044 or other partial PPAR gamma agonists/antagonists.

In a further embodiment of the invention, the compound of the formula I is administered in combination with an activator of AMP-activated protein kinase (AMPK), for example A-769662 or those compounds as described in US20050038068.

In one embodiment of the invention, the compound of the formula I is administered in combination with a fibrate, for example fenofibrate, clofibrate, bezafibrate.

In one embodiment of the invention, the compound of the formula I is administered in combination with an MTP inhibitor, for example implitapide, BMS-201038, R-103757 or those as described in WO2005085226, WO2005121091, WO2006010423.

In one embodiment of the invention, the compound of the formula I is administered in combination with a CETP inhibitor, for example torcetrapib or JTT-705, or those as described in WO2006002342, WO2006010422, WO2006012093.

In one embodiment of the invention, the compound of the formula I is administered in combination with bile acid reabsorption inhibitor (see, for example, U.S. Pat. Nos. 6,245,744, 6,221,897 or WO00/61568), for example HMR 1741, or those as described in DE 10 2005 033099.1 and DE 10 2005 033100.9.

In one embodiment of the invention, the compound of the formula I is administered in combination with a polymeric bile acid adsorber, for example cholestyramine, colesevelam.

In one embodiment of the invention, the compound of the formula I is administered in combination with an LDL receptor inducer (see U.S. Pat. No. 6,342,512), for example HMR1171, HMR1586, or those as described in WO2005097738.

In one embodiment, the compound of the formula I is administered in combination with Omacor® (omega-3 fatty acids; highly concentrated ethyl esters of eicosapentaenoic acid and of docosahexaenoic acid).

In one embodiment of the invention, the compound of the formula I is administered in combination with an ACAT inhibitor, for example avasimibe or SMP-797.

In one embodiment of the invention, the compound of the formula I is administered in combination with an antioxidant, for example OPC-14117, probucol, tocopherol, ascorbic acid, (β-carotene or selenium.

In one embodiment of the invention, the compound of the formula I is administered in combination with a vitamin, for example vitamin B6 or vitamin B 12.

In one embodiment of the invention, the compound of the formula I is administered in combination with a lipoprotein lipase modulator, for example ibrolipim (NO-1886).

In one embodiment of the invention, the compound of the formula I is administered in combination with an ATP citrate lyase inhibitor, for example SB-204990.

In one embodiment of the invention, the compound of the formula I is administered in combination with a squalene synthetase inhibitor, for example BMS-188494, or as described in WO2005077907.

In one embodiment of the invention, the compound of the formula I is administered in combination with a lipoprotein (a) antagonist, for example gemcabene (CI-1027).

In one embodiment of the invention, the compound of the formula I is administered in combination with an agonist of GPR109A (HM74A receptor agonist), for example nicotinic acid or "extended release niacin" in conjunction with MK-0524A, or those compounds as described in WO2006045565, WO2006045564, WO2006069242.

In another embodiment of the invention, the compound of the formula I is administered in combination with an agonist of GPR116, as described, for example, in WO2006067531, WO2006067532.

In one embodiment of the invention, the compound of the formula I is administered in combination with a lipase inhibitor, for example orlistat or cetilistat (ATL-962).

In one embodiment of the invention, the compound of the formula I is administered in combination with insulin.

In one embodiment, the compound of the formula I is administered in combination with a sulfonylurea, for example tolbutamide, glibenclamide, glipizide or glimepiride.

In one embodiment, the compound of the formula I is administered in combination with a substance which enhances insulin secretion, for example KCP-265 (WO2003097064).

In one embodiment, the compound of the formula I is administered in combination with agonists of the glucose-dependent insulinotropic receptor (GDIR), for example APD-668.

In one embodiment, the compound of the formula I is administered in combination with a biguanide, for example metformin.

In yet another embodiment, the compound of the formula I is administered in combination with a meglitinide, for example repaglinide or nateglinide.

In one embodiment, the compound of the formula I is administered in combination with a thiazolidinedione, for example troglitazone, ciglitazone, pioglitazone, rosiglitazone or the compounds disclosed in WO 97/41097 to Dr. Reddy's Research Foundation, especially 5-[[4-[(3,4-dihydro-3-methyl-4-oxo-2-quinazolinylmethoxy]phenyl]methyl]-2,4-thiazolidinedione.

In one embodiment, the compound of the formula I is administered in combination with an α-glucosidase inhibitor, for example miglitol or acarbose.

In one embodiment, the compound of the formula I is administered in combination with an active ingredient which acts on the ATP-dependent potassium channel of the beta cells, for example tolbutamide, glibenclamide, glipizide, glimepiride or repaglinide.

In one embodiment, the compound of the formula I is administered in combination with more than one of the aforementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment, the compound of the formula I is administered in combination with an inhibitor of glycogen phosphorylase, for example PSN-357 or FR-258900, or those as described in WO2003084922, WO2004007455, WO2005073229-31, WO2005067932.

In one embodiment, the compound of the formula I is administered in combination with glucagon receptor antagonists, for example A-770077 or NNC-25-2504 or as described in WO2004100875, WO2005065680.

In one embodiment, the compound of the formula I is administered in combination with activators of glucokinase, for example LY-2121260 (WO2004063179), PSN-105, PSN-110, GKA-50, or those as described, for example, in WO2004072031, WO2004072066, WO2005080360, WO2005044801, WO2006016194, WO2006058923.

In one embodiment, the compound of the formula I is administered in combination with an inhibitor of gluconeogenesis, for example FR-225654.

In one embodiment, the compound of the formula I is administered in combination with inhibitors of fructose 1,6-bisphosphatase (FBPase), for example CS-917 (MB-06322) or MB-07803, or those as described in WO2006023515.

In one embodiment, the compound of the formula I is administered in combination with modulators of glucose transporter 4 (GLUT4), for example KST-48 (D.-O. Lee et al.: Arzneim.-Forsch. Drug Res. 54 (12), 835 (2004)).

In one embodiment, the compound of the formula I is administered in combination with inhibitors of glutamine: fructose-6-phosphate amidotransferase (GFAT), as described, for example, in WO2004101528.

In one embodiment, the compound of the formula I is administered in combination with inhibitors of dipeptidylpeptidase-IV (DPP-IV), for example vildagliptin (LAF-237), sitagliptin (MK-0431), saxagliptin ((BMS-477118), GSK-823093, PSN-9301, SYR-322, SYR-619, TA-6666, TS-021, GRC-8200, GW-825964X, KRP-104, DP-893 or as described in WO2003074500, WO2003106456, WO200450658, WO2005058901, WO2005012312, WO2005/012308, WO2006039325, WO2006058064, PCT/EP2005/007821, PCT/EP2005/008005, PCT/EP2005/008002, PCT/EP2005/008004, PCT/EP2005/008283, DE 10 2005 012874.2 or DE 10 2005 012873.4.

In one embodiment, the compound of the formula I is administered in combination with Januvia™, a solid combination of sitagliptin phosphate with metformin hydrochloride.

In one embodiment, the compound of the formula I is administered in combination with inhibitors of 11-beta-hydroxysteroid dehydrogenase 1 (11β-HSD1), for example BVT-2733, JNJ-25918646, INCB-13739, or those as described, for example, in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004058730, WO2004065351, WO2004089367, WO2004089380, WO2004089470-71, WO2004089896, WO2005016877, WO2005097759, WO2006010546, WO2006012227, WO2006012173, WO2006017542, WO2006034804, WO2006040329, WO2006051662, WO2006048750, WO2006049952, WO2006048331, WO2006050908, WO2006024627, WO2006040329, WO2006066109.

In one embodiment, the compound of the formula I is administered in combination with inhibitors of protein tyrosine phosphatase 1B (PTP1B), as described, for example, in WO200119830-31, WO200117516, WO2004506446, WO2005012295, WO2005116003, PCT/EP2005/005311, PCT/EP2005/005321, PCT/EP2005/007151, PCT/EP2005/01294 or DE 10 2004 060542.4.

In one embodiment, the compound of the formula I is administered in combination with modulators of sodium-dependent glucose transporter 1 or 2 (SGLT1, SGLT2), for example KGA-2727, T-1095, SGL-0010, AVE 2268 and SAR 7226, or as described, for example, in WO2004007517, WO200452903, WO200452902, PCT/EP2005/005959, WO2005085237, JP2004359630, WO2005121161, WO2006018150, WO2006035796, WO2006062224, WO2006058597 or by A. L. Handlon in Expert Opin. Ther. Patents (2005) 15(11), 1531-1540.

In one embodiment, the compound of the formula I is administered in combination with GPR40 modulators.

In one embodiment, the compound of the formula I is administered in combination with GPR119b modulators, as described, for example, in WO2004041274.

In one embodiment, the compound of the fotinula I is administered in combination with GPR119 modulators, as described, for example, in WO2005061489 (PSN-632408).

In one embodiment, the compound of the formula I is administered in combination with inhibitors of hormone-sensitive lipase (HSL), as described, for example, in WO2005073199.

In one embodiment, the compound of the formula I is administered in combination with inhibitors of acetyl-CoA carboxylase (ACC), for example those as described in WO199946262, WO200372197, WO2003072197, WO2005044814, WO2005108370, JP2006131559.

In one embodiment, the compound of the formula I is administered in combination with an inhibitor of phosphoenolpyruvate carboxykinase (PEPCK), for example those as described in WO2004074288.

In one embodiment, the compound of the formula I is administered in combination with an inhibitor of glycogen synthase kinase-3 beta (GSK-3 beta), as described, for example, in US2005222220, WO2005085230, PCT/EP2005/005346, WO2003078403, WO2004022544, WO2003106410, WO2005058908, US2005038023, WO2005009997, US2005026984, WO2005000836, WO2004106343, EP1460075, WO2004014910, WO2003076442, WO2005087727, WO2004046117.

In one embodiment, the compound of the formula I is administered in combination with an inhibitor of protein kinase C beta (PKC beta), for example ruboxistaurin.

In one embodiment, the compound of the formula I is administered in combination with an endothelin A receptor antagonist, for example avosentan (SPP-301).

In one embodiment, the compound of the formula I is administered in combination with inhibitors of "I-kappaB kinase" (IKK inhibitors), as described, for example, in WO2001000610, WO2001030774, WO2004022553, WO2005097129.

In one embodiment, the compound of the formula I is administered in combination with modulators of the glucocorticoid receptor, as described, for example, in WO2005090336.

In a further embodiment, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists, for example 4-[(4-aminoquinazolin-2-ylamino)methyl]-cyclohexylmethylnaphthalene-1-sulfonamide hydrochloride (CGP 71683A);

NPY-5 receptor antagonists such as L-152804, S-2367 or as described, for example, in WO2006001318;

peptide YY 3-36 (PYY3-36) or analogous compounds, for example CJC-1682 (PYY3-36 conjugated with human serum albumin via Cys34) or CJC-1643 (derivative of PYY3-36, which is conjugated in vivo to serum albumin), or those as described in WO2005080424;

CB1R (cannabinoid receptor 1) antagonists (for example rimonabant, SR147778, SLV-319, AVE-1625, MK-0364 or salts thereof, or those as described in, for example, EP 0656354, WO 00/15609, WO2001/64632, WO2001/64633, WO2001/64634, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509, WO2005077897, WO2006047516, WO2006060461, WO2006067428, WO2006067443);

MC4 agonists (for example N-[2-(3a-benzyl-2-methyl-3-oxo-2,3,3a,4,6,7-hexahydropyrazolo[4,3-c]-pyridin-5-yl)-1-(4-chlorophenyl)-2-oxoethyl]-1-amino-1,2,3,4-tetrahydronaphthalene-2-carboxamide; (WO 01/91752)) or LB53280, LB53279, LB53278 or THIQ, MB243, RY764, CHIR-785, PT-141, or those as described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO200501921, WO200509184, WO2005000339, EP1460069, WO2005047253, WO2005047251, EP1538159, WO2004072076, WO2004072077, WO2006021655-57;

orexin receptor antagonists (for example 1-(2-methylbenzoxazol-6-yl)-3-[1,5]naphthyridin-4-ylurea hydrochloride (SB-334867-A), or those as described, for example, in WO200196302, WO200185693, WO2004085403, WO2005075458, WO2006067224);

histamine H3 receptor agonists (for example 3-cyclohexyl-1-(4,4-dimethyl-1,4,6,7-tetrahydroimidazo[4,5-c]pyridin-5-yl)-propan-1-one oxalic acid salt (WO 00/63208), or those as described in WO200064884, WO2005082893);

CRF antagonists (for example [2-Methyl-9-(2,4,6-trimethylphenyl)-9H-1,3,9-triazafluoren-4-yl]dipropylamine (WO 00/66585));

CRF BP antagonists (e.g. urocortin);

urocortin agonists;

agonists of the beta-3 adrenoceptor, for example 1-(4-chloro-3-methanesulfonylmethylphenyl)-2-[2-(2,3-dimethyl-1H-indol-6-yloxy)ethylamino]-ethanol hydrochloride (WO 01/83451) or solabegron (GW-427353) or N-5984 (KRP-204), or those as described in JP2006111553;

MSH (melanocyte-stimulating hormone) agonists;

MCH (melanine-concentrating hormone) receptor antagonists (for example NBI-845, A-761, A-665798, A-798, ATC-0175, T-226296, T-71, GW-803430, or those compounds as described in WO2003/15769, WO2005085200, WO2005019240, WO2004011438, WO2004012648, WO2003015769, WO2004072025, WO2005070898, WO2005070925, WO2004039780, WO2003033476, WO2002006245, WO2002089729, WO2002002744, WO2003004027, FR2868780, WO2006010446, WO2006038680, WO2006044293, WO2006044174);

CCK-A agonists (for example {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525) or SR-146131 (WO 0244150) or SSR-125180), or those as described in WO2005116034;

serotonin reuptake inhibitors (for example dexfenfluramine);

mixed serotoninergic and noradrenergic compounds (e.g. WO 00/71549);

5-HT receptor agonists, for example 1-(3-ethylbenzofuran-7-yl)piperazine oxalic acid salt (WO 01/09111);

5-HT2C receptor agonists (for example lorcaserine hydrochloride (APD-356) or BVT-933, or those as described in WO200077010, WO20077001-02, WO2005019180, WO2003064423, WO200242304, WO2005082859);

5-HT6 receptor antagonists, as described, for example in WO2005058858;

bombesin receptor agonists (BRS-3 agonists);

galanin receptor antagonists;

growth hormone (e.g. human growth hormone or AOD-9604);

growth hormone releasing compounds (tert-butyl 6-benzyloxy-1-(2-diisopropylaminoethylcarbamoyl)-3,4-dihydro-1H-isoquinoline-2-carboxylate (WO 01/85695));

growth hormone secretagogue receptor antagonists (ghrelin antagonists), for example A-778193, or those as described in WO2005030734;

TRH agonists (see, for example, EP 0 462 884);

decoupling protein 2 or 3 modulators;

leptin agonists (see, for example, Lee, Daniel W.; Leinung, Matthew C.; Rozhayskaya-Arena, Marina; Grasso, Patricia. Leptin agonists as a potential approach to the treatment of obesity.

Drugs of the Future (2001), 26(9), 873-881);

dopamine agonists (DA agonists, for example bromocriptine, Doprexin);

lipase/amylase inhibitors (e.g. WO 00/40569);

inhibitors of diacylglycerol O-acyltransferases (DGATs), for example BAY-74-4113, or as described, for example, in US2004/0224997, WO2004094618, WO200058491, WO2005044250, WO2005072740, JP2005206492, WO2005013907, WO2006004200, WO2006019020, WO2006064189;

inhibitors of fatty acid synthase (FAS), for example C75, or those as described in WO2004005277;

oxyntomodulin;

oleoyl-estrone or thyroid hormone receptor agonists, for example: KB-2115, or those as described in WO20058279, WO200172692, WO200194293, WO2003084915, WO2004018421, WO2005092316.

In one embodiment, the further active ingredient is varenicline tartrate, a partial agonist of the alpha 4-beta 2 nicotinic acetylcholine receptor.

In one embodiment, the further active ingredient is trodusquemine.

In one embodiment, the further active ingredient is a modulator of the enzyme SIRT1, a member of the human sirtuin enzyme family.

In one embodiment of the invention, the further active ingredient is leptin;

see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the further active ingredient is dexamphetamine or amphetamine.

In one embodiment, the further active ingredient is fenfluramine or dexfenfluramine.

In another embodiment, the further active ingredient is sibutramine.

In one embodiment, the further active ingredient is mazindol or phentermin.

In one embodiment, the further active ingredient is a diphenylazetidinone derivative, as described, for example, in U.S. Pat. Nos. 6,992,067 or 7,205,290.

In one embodiment, the compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can also be administered in the form of food products such as, for example, in bakery products or muesli bars.

It will be appreciated that every suitable combination of the compounds of the invention with one or more of the aforementioned compounds and optionally one or more other pharmacologically active substances is considered to be covered by the scope of protection conferred by the present invention.

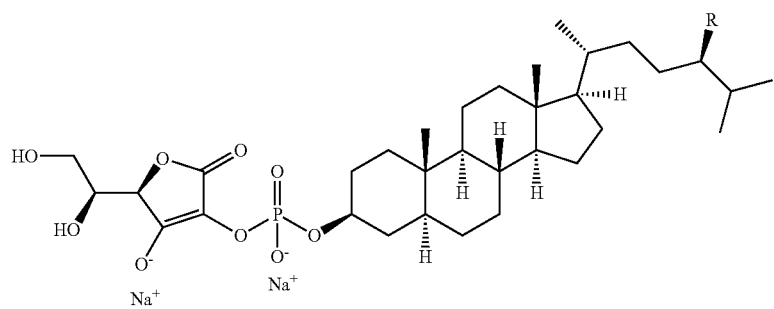
FM-VP4
R = CH₃; CH₂—CH₃
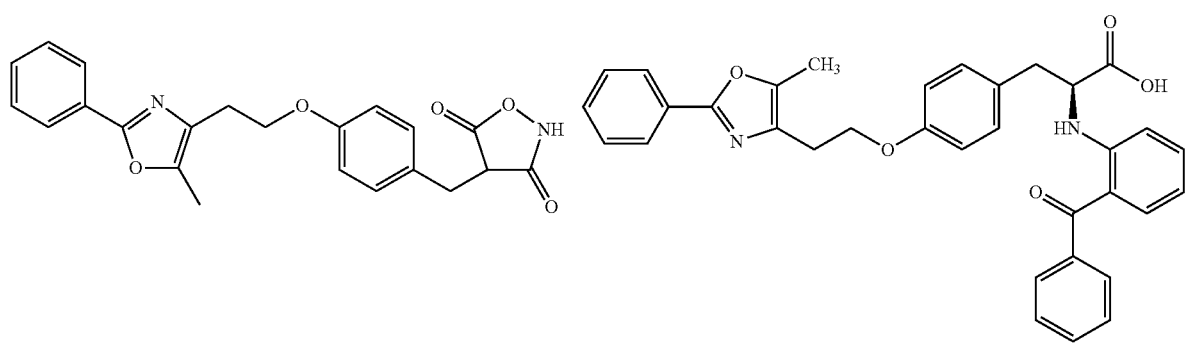
JTT-501  GI 262570
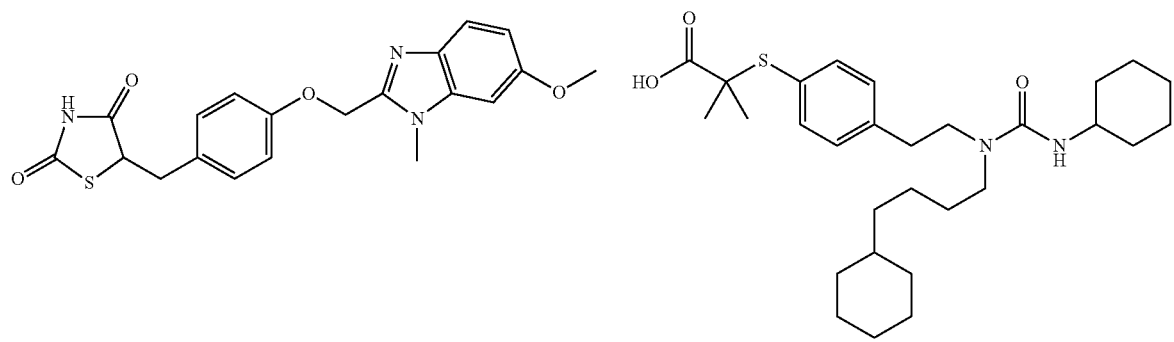
CS-011
Rivoglitazone
GW-9578
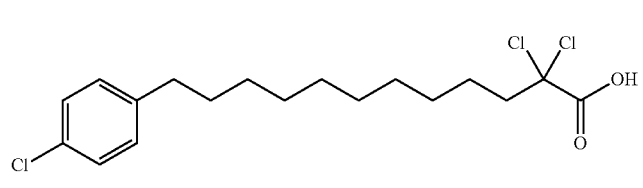
K-111
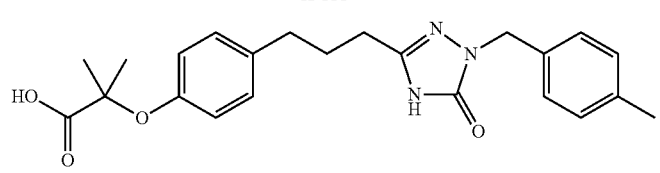
LY-518674

-continued
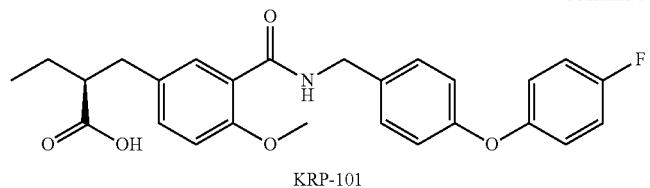
KRP-101
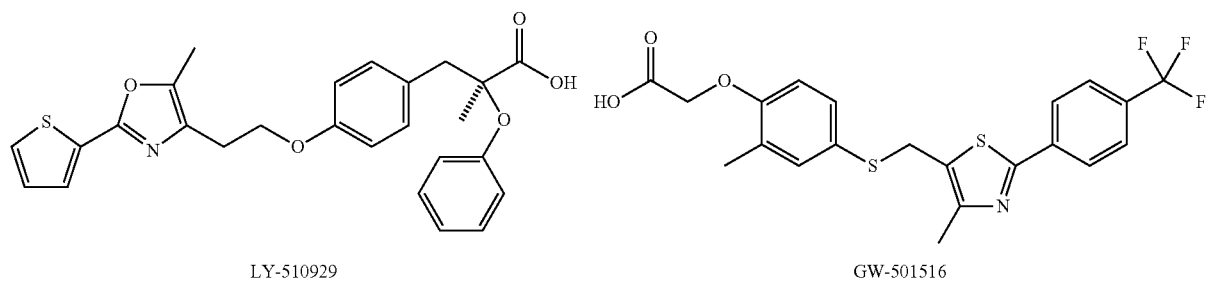
LY-510929
GW-501516
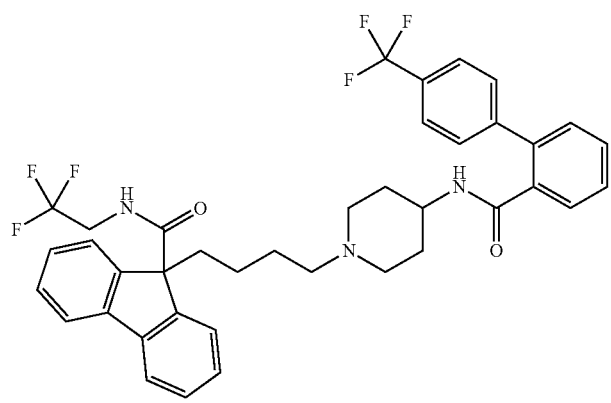
BMS-201038
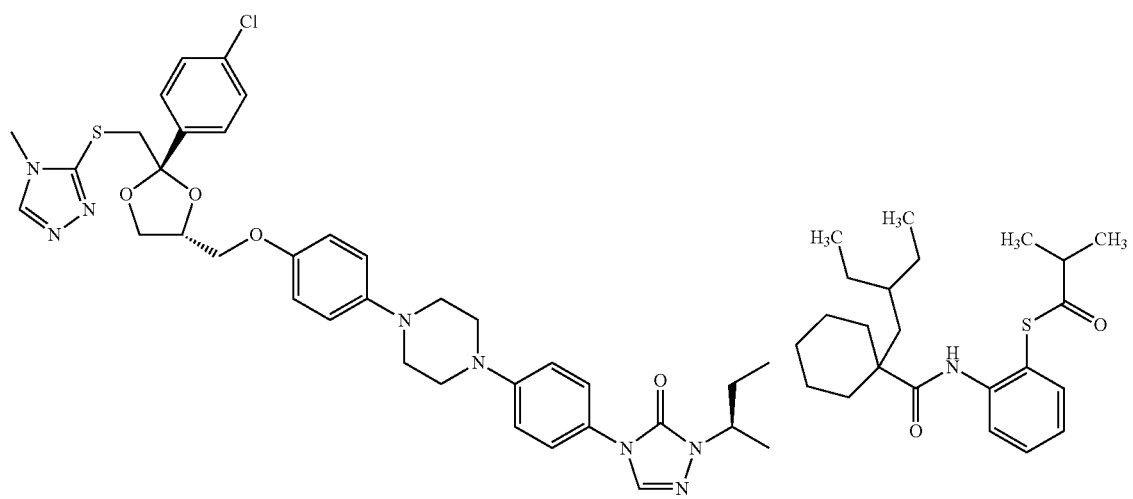
R-103757
JTT-705

-continued
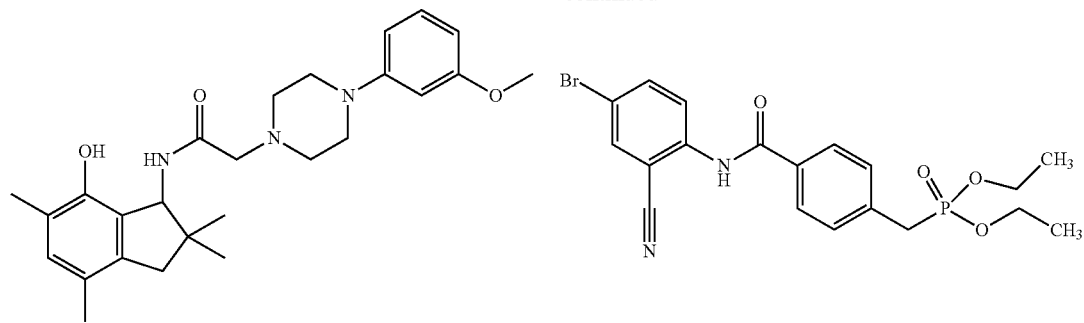
OPC-14117
NO-1886
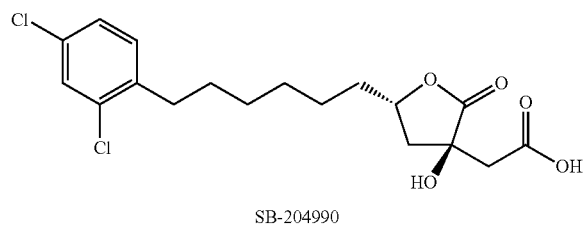
SB-204990
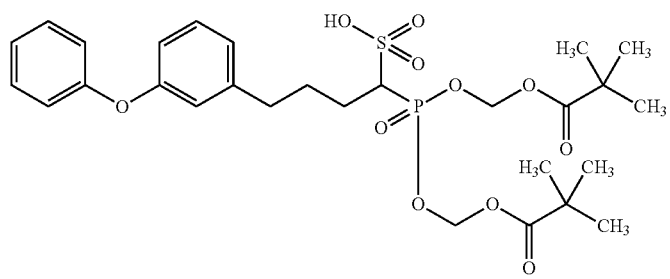
BMS-188494
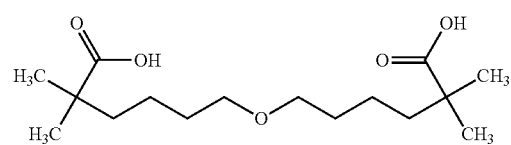
CI-1027
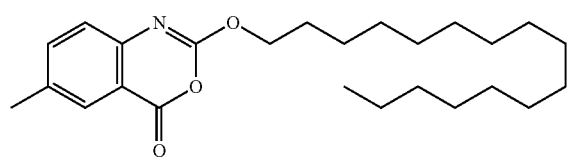
ATL-962
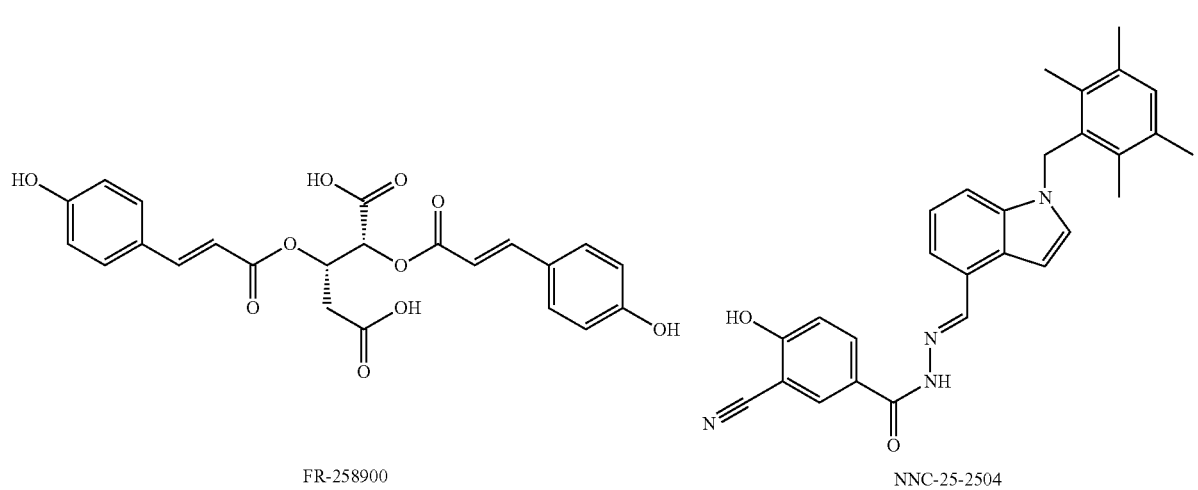
FR-258900
NNC-25-2504

-continued
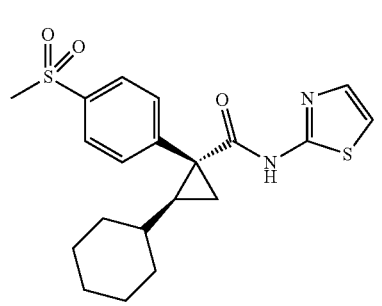
LY-2121260
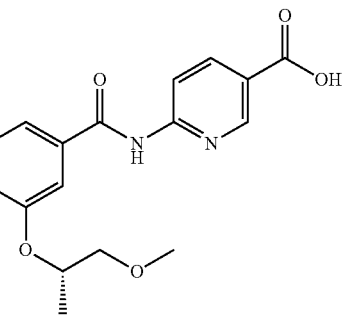
GKA-50
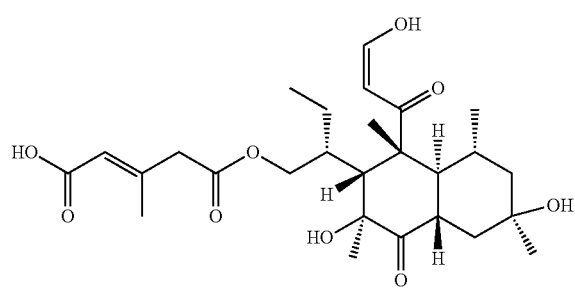
FR-225654
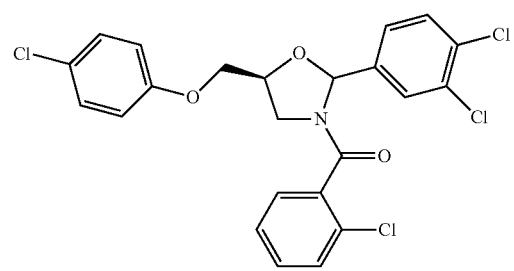
KST-48
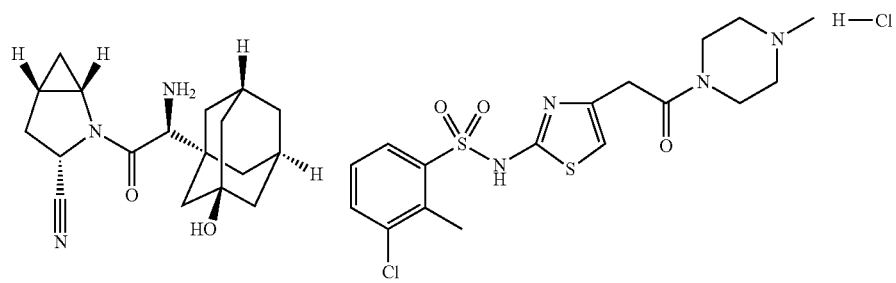
BMS-477118
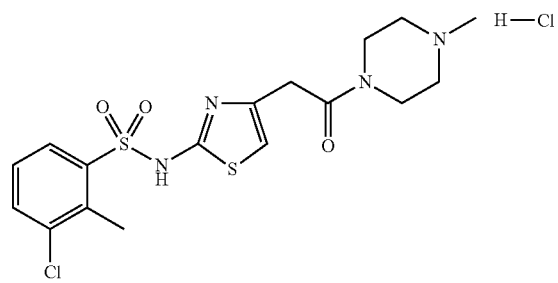
BVT-2733
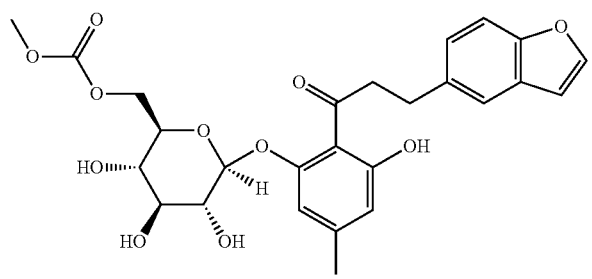
T-1095
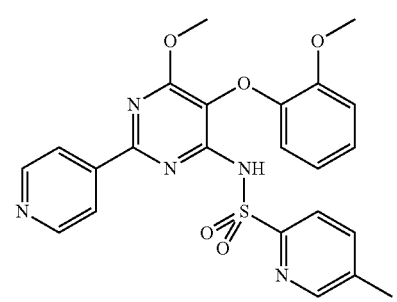
SPP-301

-continued
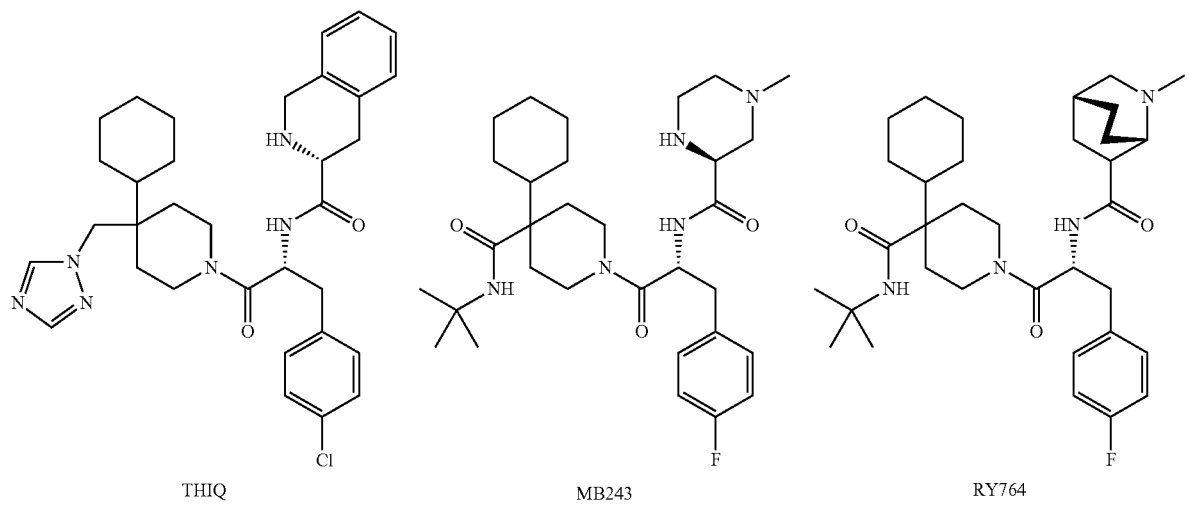
THIQ
MB243
RY764
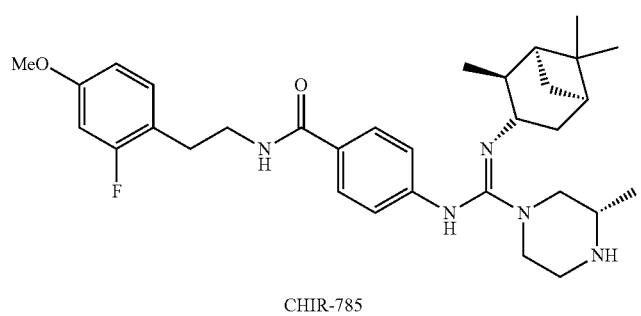
CHIR-785
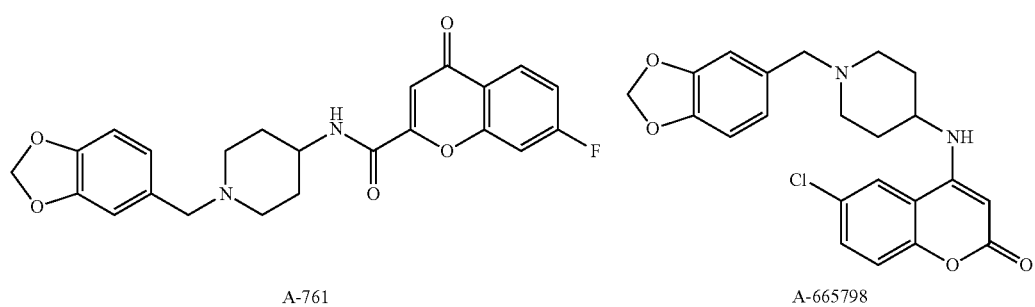
A-761
A-665798
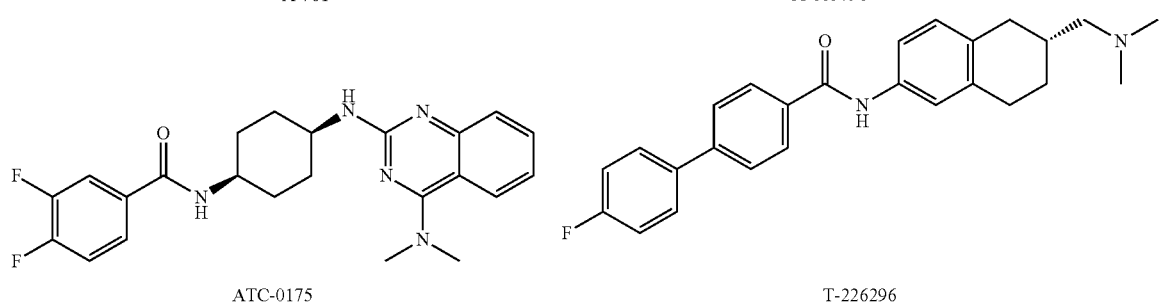
ATC-0175
T-226296
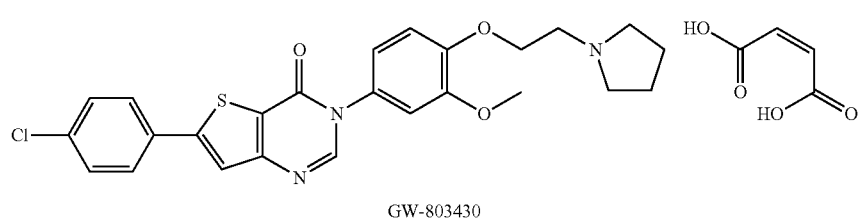
GW-803430

-continued
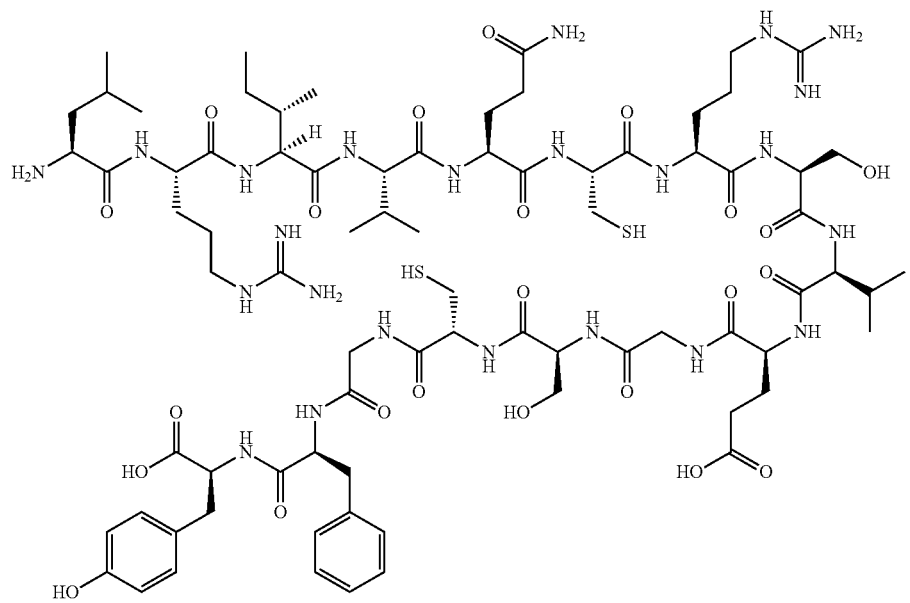
AOD-9604
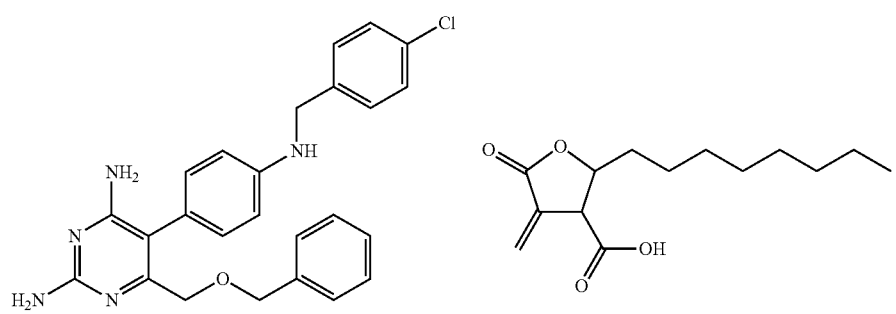
A-778193     C75
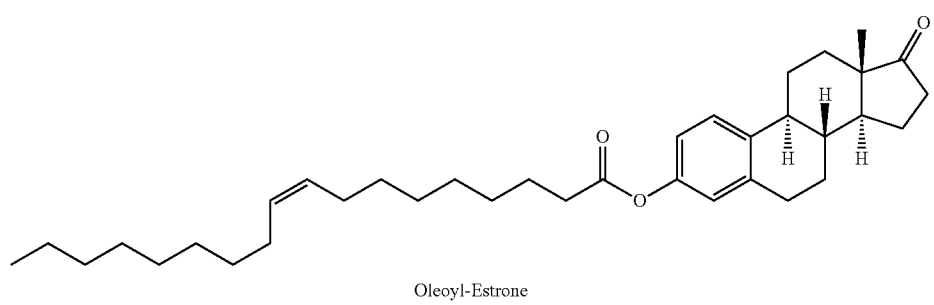
Oleoyl-Estrone
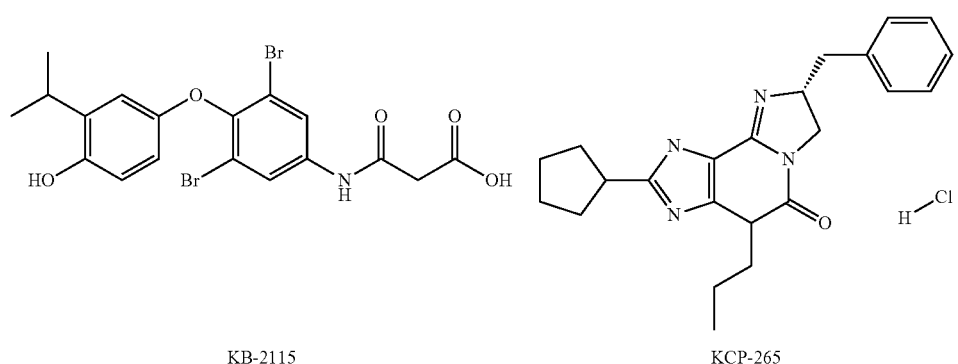
KB-2115     KCP-265

-continued
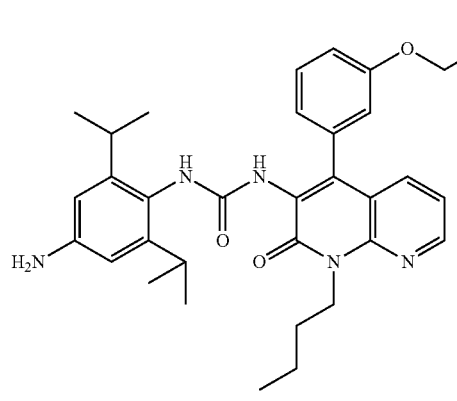
SMP-797
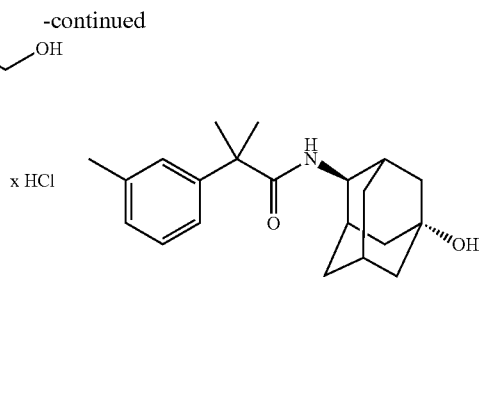
JNJ-25918646
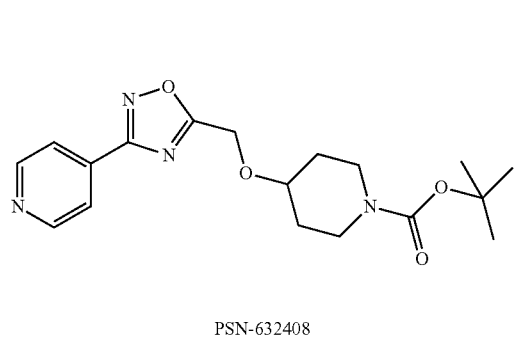
PSN-632408
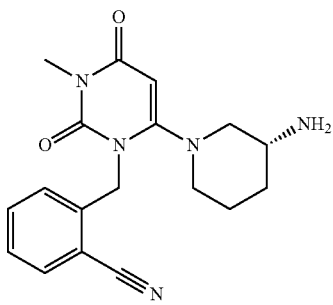
SYR-322
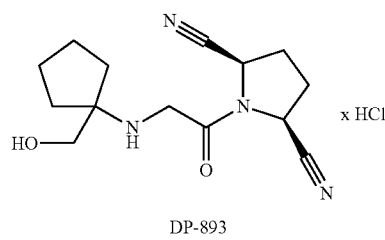
DP-893
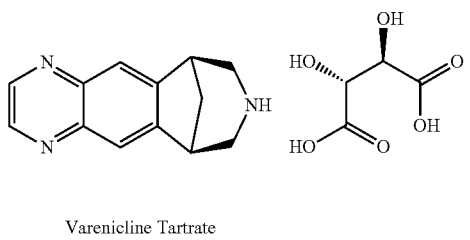
Varenicline Tartrate
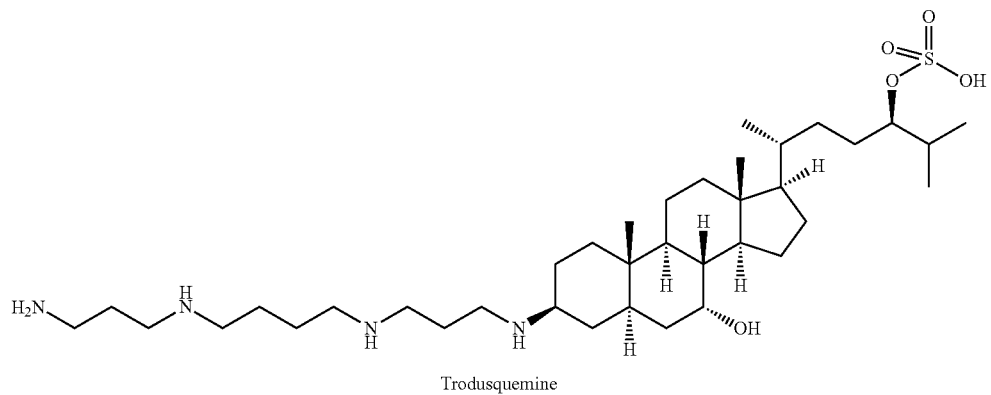
Trodusquemine x HCl
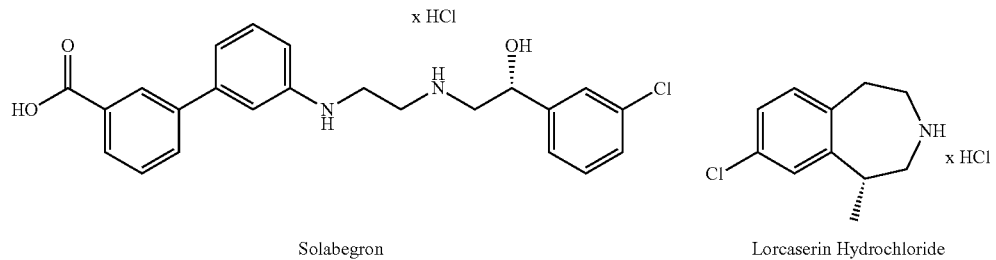
Solabegron                                    Lorcaserin Hydrochloride

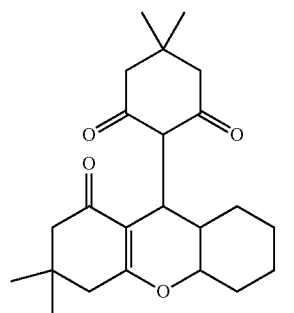
L-152804

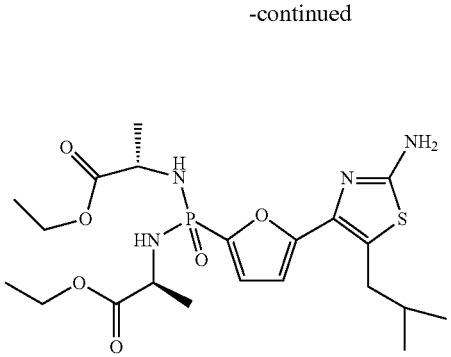
MB-06322
CS-917

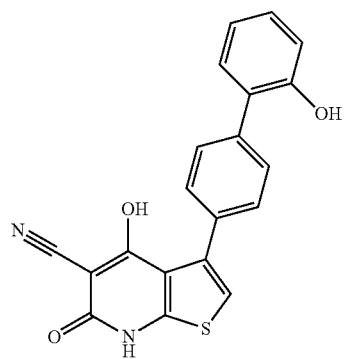
N-5984

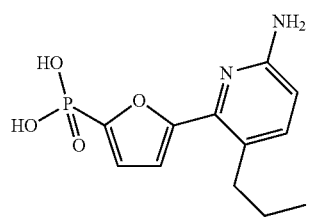
MB-07803

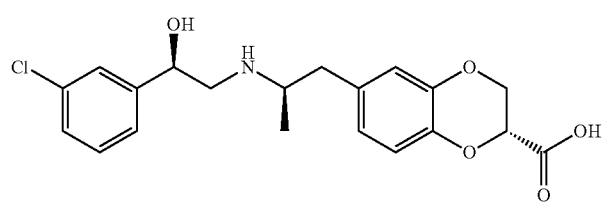
A-769662

EXAMPLES

The examples and preparation methods adduced below serve to illustrate the invention, but without limiting it.

The inventive compounds of the formula I can be prepared with the aid of reactions known in principle. For example, the compounds were prepared according to the general reaction schemes which follow.

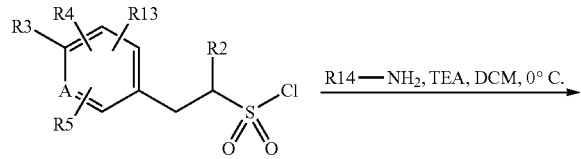

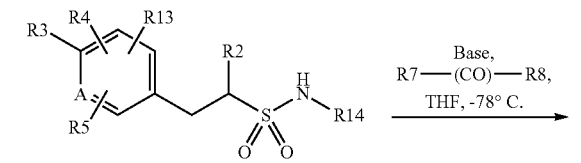

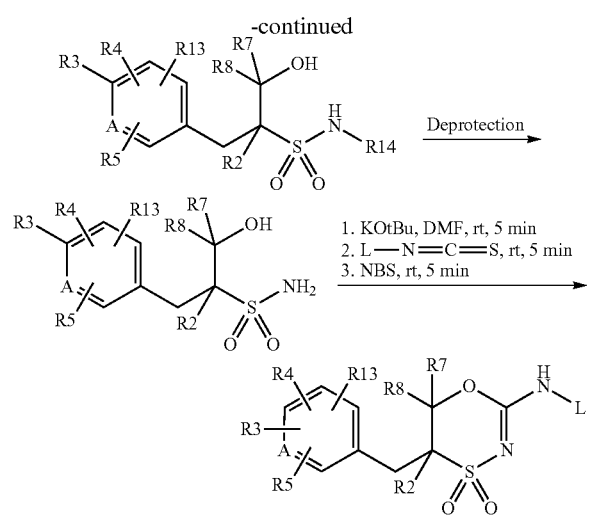

A methanesulfonyl chloride substituted by benzyl or heteromethylene and R2, through the reaction with a suitable amine and triethylamine (TEA) in a suitable solvent, for example dichloromethane (DCM), is used to prepare a correspondingly substituted methanesulfonamide protected by R14 (e.g. Boc, benzyl, 2,4-dimethoxybenzyl). By treatment with a suitable base (e.g. methyllithium) at low temperature, it is then possible to produce a dianion, which is reacted with a ketone (e.g. R7—(CO)—R8) or an aldehyde (e.g. R7—CHO) in a suitable solvent, e.g. tetrahydrofuran (THF), to give the R14-protected hydroxysulfonamide. By deprotection of R14 (for example, by acid treatment in the case of a Boc group or of a 2,4-dimethoxybenzyl group, or by hydrogenation in the case of a benzyl group), the free hydroxysulfonamide is formed. The reaction of the hydroxysulfonamide thus obtained with base and an isothiocyanate (L-N=C=S) in a suitable solvent, for example dimethylformamide (DMF), and subsequent oxidative ring closure with N-bromosuccinimide (NBS) gives the desired 4,4-dioxooxathiazines.

In the cases in which the functional groups (for example a hydroxyl group) are introduced in protected form (for example benzyl-protected or as the ester), these are released at the end of the synthesis by a suitable method (for example hydrogenation or reduction).

The isothiocyanates used are obtained by the reaction of a primary amine with thiocarbonyldiimidazole, in which case any troublesome functional groups present, for example hydroxyl groups, are blocked with suitable protecting groups, for example silyl ethers. The protecting groups are removed at the end of the sequence by suitable methods, for example silyl groups by treatment with methanolic hydrochloric acid.

In the cases in which diastereomers or racemates form during the synthesis, these can be separated from one another by preparative HPLC.

Some of the primary amines used are commercially available.

4-Fluorobicyclo[2.2.2]octan-1-amine can be prepared as described in the literature (JOC 1982, 47, 1952-7).

Other inventive compounds can be obtained in other ways outlined by way of example in the scheme which follows.

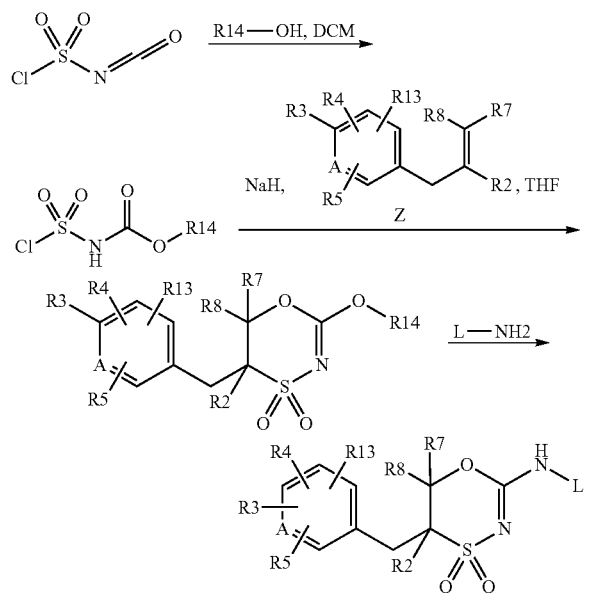

In analogy to a literature method (JACS 1972, 94, 4386-7), chlorosulfonyl isocyanate is reacted with an alcohol (R14—OH, e.g. methanol), forming a corresponding carboalkoxysulfamoyl chloride (e.g. carbomethoxysulfamoyl chloride). This is deprotonated with sodium hydride, and the intermediate formed after chloride elimination (e.g. methyl-N-sulfonylurethane) is reacted in a 2+4 cycloaddition with a suitable alkene of the formula Z to give the alkoxy-substituted (e.g. methoxy-substituted) 4,4-dioxooxathiazine. The alkoxy group (—O—R14) is then replaced by means of an amine (L-NH$_2$) in a suitable solvent (e.g. dichloromethane), forming the desired 4,4-dioxooxathiazines In the cases in which diastereomers or racemates form during the synthesis, these can be separated from one another by preparative HPLC.

Other inventive compounds can be obtained in other ways outlined by way of example in the scheme which follows.

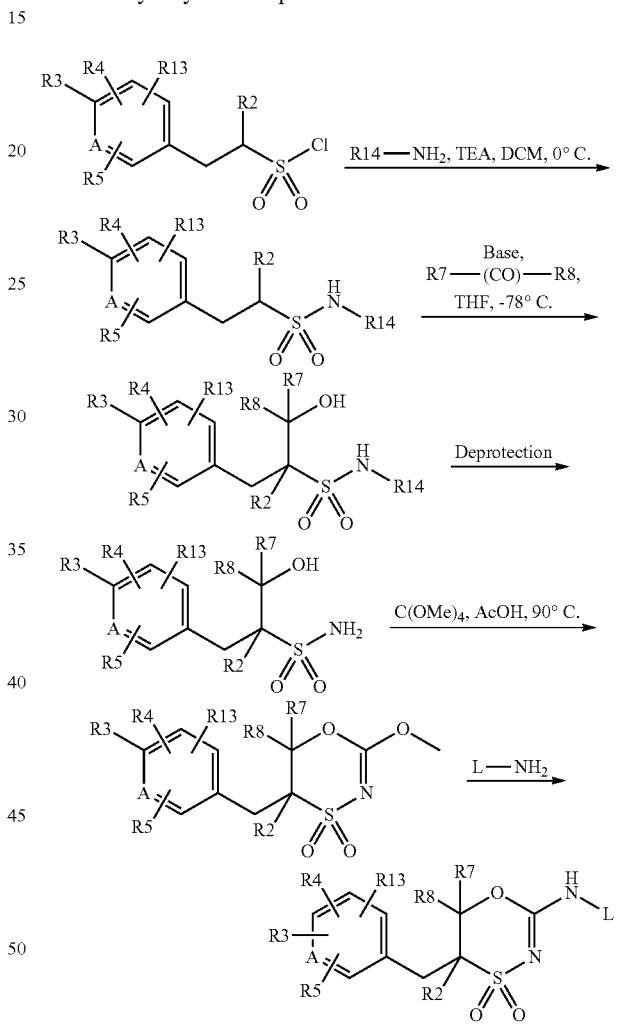

A methanesulfonyl chloride substituted by benzyl or heteromethylene and R2, through the reaction with a suitable amine and triethylamine (TEA) in a suitable solvent, for example dichloromethane (DCM), is used to prepare a correspondingly substituted methanesulfonamide protected by R14 (e.g. Boc, benzyl, 2,4-dimethoxybenzyl). By treatment with a suitable base (e.g. methyllithium) at low temperature, it is then possible to produce a dianion, which is reacted with a ketone (e.g. R7—(CO)—R8) or an aldehyde (e.g. R7—CHO) in a suitable solvent, e.g. tetrahydrofuran (THF), to give the R14-protected hydroxysulfonamide. By deprotection of R14 (for example, by acid treatment in the case of a Boc group or of a 2,4-dimethoxybenzyl group, or by hydrogenation in the case of a benzyl group), the free hydroxysulfonamide is formed. The reaction of the hydroxysulfonamide thus obtained with tetramethyl orthocarbonate gives methoxy-substituted 4,4-dioxooxathiazines. The methoxy group (—O—CH$_3$) is then replaced by means of an amine (L-NH$_2$) in a suitable solvent (e.g. dichloromethane), forming the desired 4,4-dioxooxathiazines.

In the cases in which the functional groups (for example a hydroxyl group) are introduced in protected form (for example benzyl-protected or as the ester), these are released at the end of the synthesis by a suitable method (for example hydrogenation or reduction).

If the molecule which forms includes a haloaryl unit, the halogen can be replaced by standard metal-catalyzed coupling methods. For example, a bromide can be converted further with the aid of a Suzuki reaction or a Sonogashira reaction or a palladium-catalyzed amination. In addition, simple synthesis steps may follow in some cases; for example, a triple bond can be hydrogenated to a single bond or a Boc-protected amine can be deprotected and then alkylated.

Some of the amines used are commercially available or can be prepared by methods known from the literature.

Others among the primary amines used were prepared as outlined in the scheme which follows.

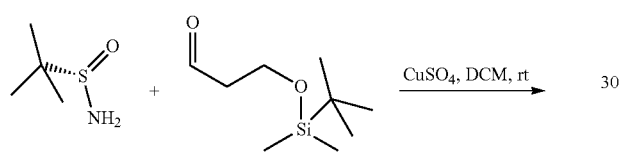

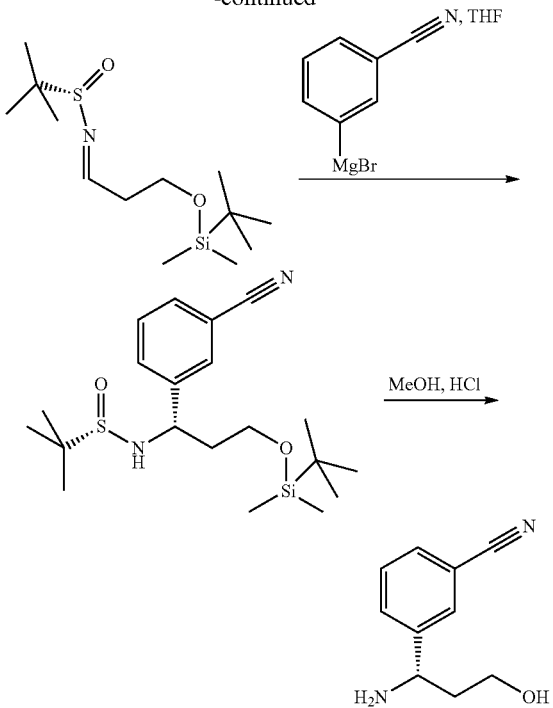

The examples adduced hereinafter serve to illustrate the invention, but without restricting it. Table 1:

| Example | CHEMISTRY | Method | Retention time | Molar mass (g/mol) | Name |
|---|---|---|---|---|---|
| 1 | | A | 1.046 | 437.0 | (S)-3-[5-(4-Chlorobenzyl)-6,6-dimethyl-4,4-dioxo-5,6-dihydro-4H-4lambda6-[1,4,3]oxathiazin-2-ylamino]-3-phenyl-propan-1-ol |
| 2 | | A | 0.992 | 402.5 | (S)-3-(5-Benzyl-6,6-dimethyl-4,4-dioxo-5,6-dihydro-4H-4lambda6-[1,4,3]oxathiazin-2-ylamino)-3-phenyl-propan-1-ol |
| 3 | | A | 1.174 | 483.4 | [5-(4-Bromobenzyl)-5,6,6-trimethyl-4,4-dioxo-5,6-dihydro-4H-4lambda6-[1,4,3]oxathiazin-2-yl]-[(S)-1-(2-fluorophenyl)-ethyl]-amine |

-continued

| Example | CHEMISTRY | Method | Retention time | Molar mass (g/mol) | Name |
|---|---|---|---|---|---|
| 4 | | A | 1.083 | 513.4 | (S)-3-[5-(4-Bromobenzyl)-5,6,6-trimethyl-4,4-dioxo-5,6-dihydro-4H-4lambda6-[1,4,3]oxathiazin-2-ylamino]-3-(2-fluorophenyl)-propan-1-ol |
| 5 | | A | 1.115 | 404.5 | (5-Benzyl-5,6,6-trimethyl-4,4-dioxo-5,6-dihydro-4H-4lambda6-[1,4,3]oxathiazin-2-yl)-[(S)-1-(2-fluorophenyl)-ethyl]-amine |
| 6 | | A | 0.827 | 511.6 | (S)-3-(2-Fluorophenyl)-3-[5,6,6-trimethyl-4,4-dioxo-5-(4-pyridin-2-yl-benzyl)-5,6-dihydro-4H-4lambda6-[1,4,3]oxathiazin-2-ylamino]-propan-1-ol |
| 7 | | A | 1.135 | 579.6 | (S)-3-(2-Fluorophenyl)-3-{5,6,6-trimethyl-4,4-dioxo-5-[4-(5-trifluoromethyl-pyridin-2-yl)-benzyl]-5,6-dihydro-4H-4lambda6-[1,4,3]oxathiazin-2-ylamino}-propan-1-ol |
| 8 | | A | 1.115 | 565.6 | (S)-3-{6,6-Dimethyl-4,4-dioxo-5-[4-(5-trifluoromethyl-pyridin-2-yl)-benzyl]-5,6-dihydro-4H-4lambda6-[1,4,3]oxathiazin-2-ylamino}-3-(2-fluoro-phenyl)-propan-1-ol |
| 9 | | A | 1.09 | 496.6 | (S)-3-(5-Biphenyl-3-ylmethyl-6,6-dimethyl-4,4-dioxo-5,6-dihydro-4H-4lambda6-[1,4,3]oxathiazin-2-ylamino)-3-(2-fluoro-phenyl)-propan-1-ol |

-continued

| Example | CHEMISTRY | Method | Retention time | Molar mass (g/mol) | Name |
|---|---|---|---|---|---|
| 10 | | A | 1.114 | 496.6 | (S)-3-(5-Biphenyl-4-ylmethyl-6,6-dimethyl-4,4-dioxo-5,6-dihydro-4H-4lambda6-[1,4,3]oxathiazin-2-ylamino)-3-(2-fluoro-phenyl)-propan-1-ol |
| 11 | | A | 1.023 | 437.0 | (S)-3-(5-Benzyl-6,6-dimethyl-4,4-dioxo-5,6-dihydro-4H-4lambda6-[1,4,3]oxathiazin-2-ylamino)-3-(2-chlorophenyl)-propan-1-ol |
| 12 | | A | 0.998 | 420.5 | (S)-3-(5-Benzyl-6,6-dimethyl-4,4-dioxo-5,6-dihydro-4H-4lambda6-[1,4,3]oxathiazin-2-ylamino)-3-(2-fluorophenyl)-propan-1-ol |
| 13 | | A | 1.032 | 454.9 | (S)-3-(5-Benzyl-6,6-dimethyl-4,4-dioxo-5,6-dihydro-4H-4lambda6-[1,4,3]oxathiazin-2-ylamino)-3-(2-chloro-3-fluorophenyl)-propan-1-ol |
| 14 | | A | 1.039 | 454.9 | (S)-3-(5-Benzyl-6,6-dimethyl-4,4-dioxo-5,6-dihydro-4H-4lambda6-[1,4,3]oxathiazin-2-ylamino)-3-(5-chloro-2-fluorophenyl)-propan-1-ol |
| 15 | | A | 1.042 | 437.0 | (S)-3-(5-Benzyl-6,6-dimethyl-4,4-dioxo-5,6-dihydro-4H-4lambda6-[1,4,3]oxathiazin-2-ylamino)-3-(4-chlorophenyl)-propan-1-ol |

-continued

| Example | CHEMISTRY | Method | Retention time | Molar mass (g/mol) | Name |
|---|---|---|---|---|---|
| 16 | | A | 1.034 | 437.0 | (S)-3-(5-Benzyl-6,6-dimethyl-4,4-dioxo-5,6-dihydro-4H-4lambda6-[1,4,3]oxathiazin-2-ylamino)-3-(3-chlorophenyl)-propan-1-ol |
| 17 | | A | 0.989 | 438.5 | (S)-3-(5-Benzyl-6,6-dimethyl-4,4-dioxo-5,6-dihydro-4H-4lambda6-[1,4,3]oxathiazin-2-ylamino)-3-(2,5-difluorophenyl)-propan-1-ol |
| 18 | | A | 0.998 | 438.5 | (S)-3-(5-Benzyl-6,6-dimethyl-4,4-dioxo-5,6-dihydro-4H-4lambda6-[1,4,3]oxathiazin-2-ylamino)-3-(2,4-difluorophenyl)-propan-1-ol |
| 19 | | A | 1.007 | 434.5 | (S)-3-(5-Benzyl-6,6-dimethyl-4,4-dioxo-5,6-dihydro-4H-4lambda6-[1,4,3]oxathiazin-2-ylamino)-3-(5-fluoro-2-methyl-phenyl)-propan-1-ol |
| 20 | | A | 1.075 | 394.5 | (5-Benzyl-6,6-dimethyl-4,4-dioxo-5,6-dihydro-4H-4lambda6-[1,4,3]oxathiazin-2-yl)-(4-fluoro-bicyclo[2.2.2]oct-1-yl)-amine |
| 21 | | A | 1.052 | 470.5 | (S)-3-(6,6-Dimethyl-5-naphthalen-1-ylmethyl-4,4-dioxo-5,6-dihydro-4H-4lambda6-[1,4,3]oxathiazin-2-ylamino)-3-(2-fluorophenyl)-propan-1-ol |

-continued

| Example | CHEMISTRY | Method | Retention time | Molar mass (g/mol) | Name |
|---|---|---|---|---|---|
| 22 | | A | 0.798 | 503.6 | (S)-3-[6,6-Dimethyl-4,4-dioxo-5-(4-piperidin-4-yl-benzyl)-5,6-dihydro-4H-4lambda6-[1,4,3]oxathiazin-2-ylamino]-3-(2-fluorophenyl)-propan-1-ol |
| 23 | | A | 0.798 | 501.6 | (S)-3-{6,6-Dimethyl-4,4-dioxo-5-[4-(1,2,3,6-tetrahydro-pyridin-4-yl)-benzyl]-5,6-dihydro-4H-4lambda6-[1,4,3]oxathiazin-2-ylamino}-3-(2-fluoro-phenyl)-propan-1-ol |
| 24 | | A | 0.812 | 515.6 | (S)-3-{6,6-Dimethyl-5-[4-(1-methyl-1,2,3,6-tetrahydro-pyridin-4-yl)-benzyl]-4,4-dioxo-5,6-dihydro-4H-4lambda6-[1,4,3]oxathiazin-2-ylamino}-3-(2-fluorophenyl)-propan-1-ol |
| 25 | | A | 0.812 | 517.7 | (S)-3-{6,6-Dimethyl-5-[4-(1-methyl-piperidin-4-benzyl]-4,4-dioxo-5,6-dihydro-4H-4lambda6-[1,4,3]oxathiazin-2-ylamino}-3-(2-fluorophenyl)-propan-1-ol |
| 26 | | A | 0.811 | 561.7 | (S)-3-(2-fluorophenyl)-3-(5-{4-[1-(3-propyl)-piperidin-4-yl]-benzyl}-6,6-dimethyl-4,4-dioxo-5,6-dihydro-4H-4lambda6-[1,4,3]oxathiazin-2-ylamino)-propan-1-ol |
| 27 | | A | 0.808 | 547.7 | (S)-3-(2-fluorophenyl)-3-(5-{4-[1-(2-hydroxy-piperidin-4-yl]-benzyl}-6,6-dimethyl-4,4-dioxo-5,6-dihydro-4H-4lambda6-[1,4,3]oxathiazin-2-ylamino)-propan-1-ol |

-continued

| Example | CHEMISTRY | Method | Retention time | Molar mass (g/mol) | Name |
|---|---|---|---|---|---|
| 28 | 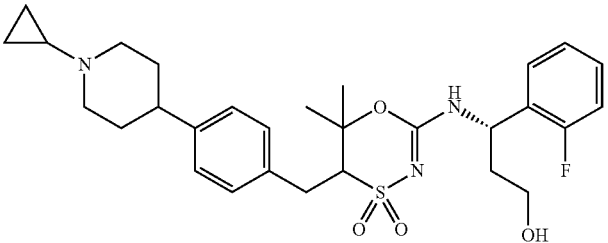 [SMILES: CC1(C)OC(N[C@@H](CCO)c2ccccc2F)=NS(=O)(=O)C1Cc1ccc(C2CCN(C3CC3)CC2)cc1] | A | 0.832 | 543.7 | (S)-3-{5-[4-(1-Cyclopropyl-piperidin-4-yl)-benzyl]-6,6-dimethyl-4,4-dioxo-5,6-dihydro-4H-4lambda6-[1,4,3]oxathiazin-2-ylamino}-3-(2-fluorophenyl)-propan-1-ol |
| 29 | 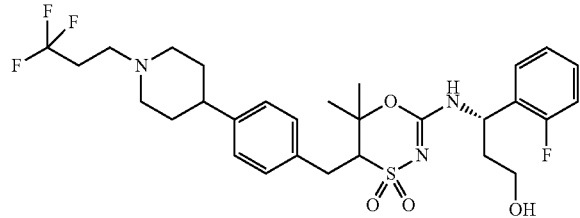 [SMILES: CC1(C)OC(N[C@@H](CCO)c2ccccc2F)=NS(=O)(=O)C1Cc1ccc(C2CCN(CCC(F)(F)F)CC2)cc1] | A | 0.863 | 599.7 | (S)-3-(6,6-Dimethyl-4,4-dioxo-5-{4-[1-(3,3,3-trifluoropropyl)-piperidin-4-yl]-benzyl}-5,6-dihydro-4H-4lambda6-[1,4,3]oxathiazin-2-ylamino)-3-(2-fluorophenyl)-propan-1-ol |
| 30 | 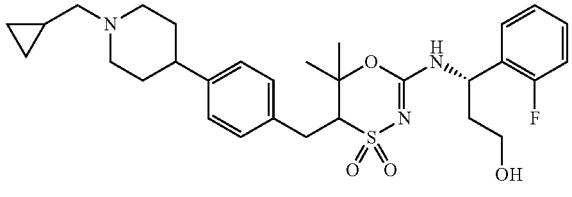 [SMILES: CC1(C)OC(N[C@@H](CCO)c2ccccc2F)=NS(=O)(=O)C1Cc1ccc(C2CCN(CC3CC3)CC2)cc1] | A | 0.844 | 557.7 | (S)-3-{5-[4-(1-Cyclopropylmethyl-piperidin-4-yl)-benzyl]-6,6-dimethyl-4,4-dioxo-5,6-dihydro-4H-4lambda6-[1,4,3]oxathiazin-2-ylamino}-3-(2-fluorophenyl)-propan-1-ol |
| 31 | 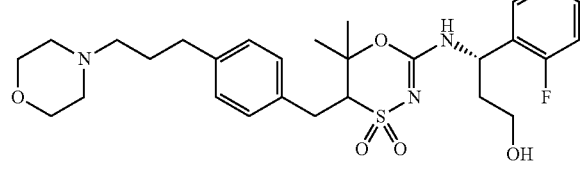 | A | 0.823 | 547.7 | (S)-3-{6,6-Dimethyl-5-[4-(3-morpholin-4-yl-benzyl]-4,4-dioxo-5,6-dihydro-4H-4lambda6-[1,4,3]oxathiazin-2-ylamino}-3-(2-fluorophenyl)-propan-1-ol |
| 32 | 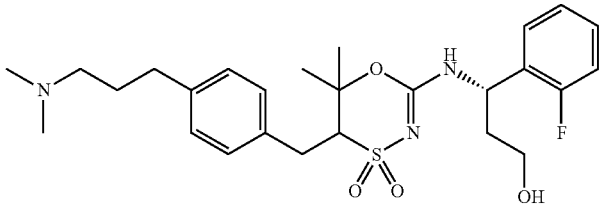 [SMILES: CN(C)CCCc1ccc(CC2C(C)(C)OC(N[C@@H](CCO)c3ccccc3F)=NS2(=O)=O)cc1] | A | 0.825 | 505.6 | (S)-3-{5-[4-(3-Dimethylamino-propyl)-benzyl]-6,6-dimethyl-4,4-dioxo-5,6-dihydro-4H-4lambda6-[1,4,3]oxathiazin-2-ylamino}-3-(2-fluorophenyl)-propan-1-ol |
| 33 | 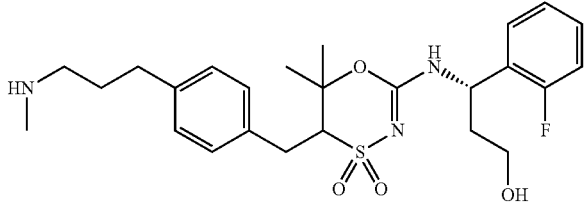 [SMILES: CNCCCc1ccc(CC2C(C)(C)OC(N[C@@H](CCO)c3ccccc3F)=NS2(=O)=O)cc1] | A | 0.818 | 491.6 | (S)-3-{6,6-Dimethyl-5-[4-(3-methylamino-propyl)-benzyl]-4,4-dioxo-5,6-dihydro-4H-4lambda6-[1,4,3]oxathiazin-2-ylamino}-3-(2-fluorophenyl)-propan-1-ol |
| 34 | 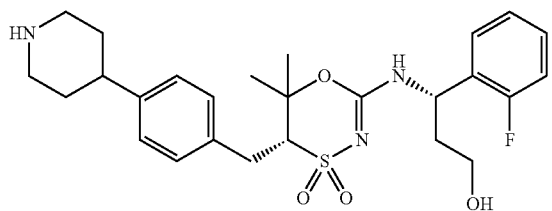 | A | 0.802 | 503.6 | (S)-3-[(R)-6,6-Dimethyl-4,4-dioxo-5-(4-piperidin-4-yl-benzyl)-5,6-dihydro-4H-4lambda6-[1,4,3]oxathiazin-2-ylamino]-3-(2-fluorophenyl)-propan-1-ol * |

-continued

| Example | CHEMISTRY | Method | Retention time | Molar mass (g/mol) | Name |
|---|---|---|---|---|---|
| 35 | 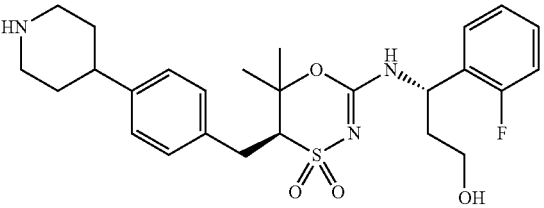 [SMILES: CC1(C)OC(N[C@@H](CCO)c2ccccc2F)=NS(=O)(=O)[C@H]1Cc1ccc(C2CCNCC2)cc1] | A | 0.797 | 503.6 | (S)-3-[(S)-6,6-Dimethyl-4,4-dioxo-5-(4-piperidin-4-yl-benzyl)-5,6-dihydro-4H-4lambda6-[1,4,3]oxathiazin-2-ylamino]-3-(2-fluorophenyl)-propan-1-ol * |
| 36 | 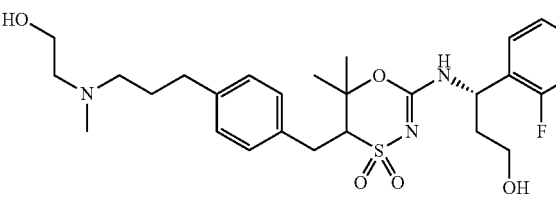 | A | 0.798 | 535.7 | (S)-3-(2-fluorophenyl)-3-[5-(4-{3-[(2-hydroxy-methyl-amino]-propyl}-benzyl)-6,6-dimethyl-4,4-dioxo-5,6-dihydro-4H-4lambda6-[1,4,3]oxathiazin-2-ylamino]-propan-1-ol |
| 37 | 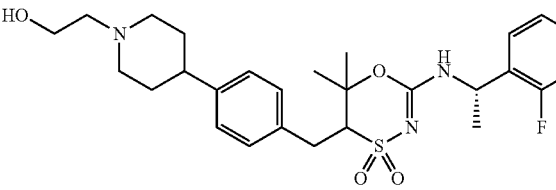 | A | 0.875 | 517.7 | 2-[4-(4-{2-[(S)-1-(2-fluorophenyl)-ethylamino]-6,6-dimethyl-4,4-dioxo-5,6-dihydro-4H-4lambda6-[1,4,3]oxathiazin-5-ylmethyl}-phenyl)-piperidin-1-yl]-ethanol |
| 38 | 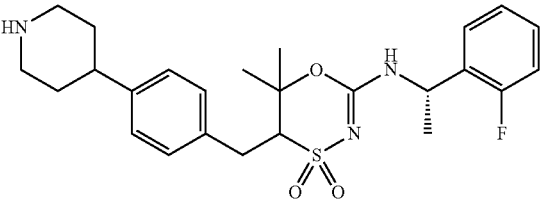 [SMILES: C[C@H](NC1=NS(=O)(=O)[C@H](Cc2ccc(N3CCNCC3)cc2)C(C)(C)O1)c1ccccc1F] HCl | A | 0.856 | 473.6 | [6,6-Dimethyl-4,4-dioxo-5-(4-piperidin-4-yl-benzyl)-5,6-dihydro-4H-4lambda6-[1,4,3]oxathiazin-2-yl]-[(S)-1-(2-fluorophenyl)-ethyl]-amine |
| 39 | 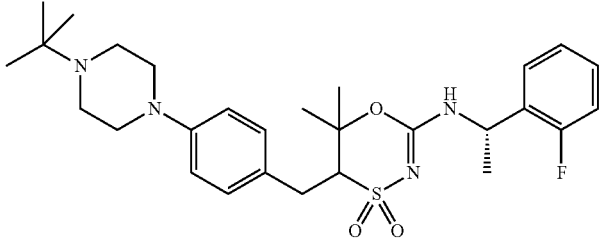 [SMILES: C[C@H](NC1=NS(=O)(=O)C(Cc2ccc(N3CCN(C(C)(C)C)CC3)nc2)C(C)(C)O1)c1ccccc1F] HCl | A | 0.903 | 530.7 | {5-[4-(4-tert-Butyl-piperazin-1-yl)-benzyl]-6,6-dimethyl-4,4-dioxo-5,6-dihydro-4H-4lambda6-[1,4,3]oxathiazin-2-yl}-[(S)-1-(2-fluorophenyl)-ethyl]-amine |
| 40 | 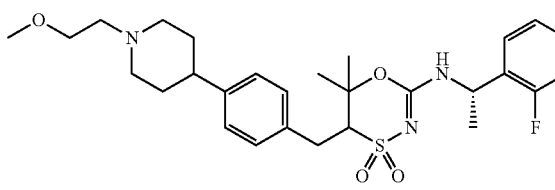 HCl | A | 0.889 | 531.7 | [(S)-1-(2-fluorophenyl)-ethyl]-(5-{4-[1-(2-methoxy-ethyl)-piperidin-4-yl]-benzyl}-6,6-dimethyl-4,4-dioxo-5,6-dihydro-4H-4lambda6-[1,4,3]oxathiazin-2-yl)-amine |

-continued

| Example | CHEMISTRY | Method | Retention time | Molar mass (g/mol) | Name |
|---|---|---|---|---|---|
| 41 | HCl | A | 0.828 | 543.7 | (S)-3-{(R)-5-[4-(1-Cyclopropyl-piperidin-4-yl)-benzyl]-6,6-dimethyl-4,4-dioxo-5,6-dihydro-4H-4lambda6-[1,4,3]oxathiazin-2-ylamino}-3-(2-fluoro-phenyl)-propan-1-ol * |
| 42 | HCl | A | 0.829 | 543.7 | (S)-3-{(S)-5-[4-(1-Cyclopropyl-piperidin-4-yl)-benzyl]-6,6-dimethyl-4,4-dioxo-5,6-dihydro-4H-4lambda6-[1,4,3]oxathiazin-2-ylamino}-3-(2-fluoro-phenyl)-propan-1-ol * |
| 43 | H Cl | A | 0.894 | 513.7 | {5-[4-(1-Cyclopropyl-piperidin-4-yl)-benzyl]-6,6-dimethyl-4,4-dioxo-5,6-dihydro-4H-4lambda6-[1,4,3]oxathiazin-2-yl}-[(S)-1-(2-fluorophenyl)-ethyl]-amine |
| 44 | | A | 0.86 | 532.6 | 5-{2-[(S)-1-(2-fluorophenyl)-ethylamino]-6,6-dimethyl-4,4-dioxo-5,6-dihydro-4H-4lambda6-[1,4,3]oxathiazin-5-ylmethyl}-3',4',5',6'-tetrahydro-2'H-[2,4']bipyridinyl-1'-carboxylic acid methyl ester |
| 45 | | A | 0.865 | 474.6 | [(R)-6,6-Dimethyl-4,4-dioxo-5-(4-piperazin-1-yl-benzyl)-5,6-dihydro-4H-4lambda6-[1,4,3]oxathiazin-2-yl]-[(S)-1-(2-fluorophenyl)-ethyl]-amine * |
| 46 | | A | 0.893 | 477.6 | {(R)-5-[4-(2-Amino-2-methyl-propoxy)-benzyl]-6,6-dimethyl-4,4-dioxo-5,6-dihydro-4H-4lambda6-[1,4,3]oxathiazin-2-yl}-[(S)-1-(2-fluorophenyl)-ethyl]-amine * |

-continued

| Example | CHEMISTRY | Method | Retention time | Molar mass (g/mol) | Name |
|---|---|---|---|---|---|
| 47 | | A | 0.862 | 488.6 | {(R)-6,6-Dimethyl-5-[4-(4-methyl-piperazin-1-benzyl]-4,4-dioxo-5,6-dihydro-4H-4lambda6-[1,4,3]oxathiazin-2-yl}-[(S)-1-(2-fluorophenyl)-ethyl]-amine * |
| 48 | HCl | A | 0.905 | 530.7 | {(R)-5-[4-(4-tert-Butyl-piperazin-1-yl)-benzyl]-dimethyl-4,4-dioxo-5,6-dihydro-4H-4lambda6-[1,4,3]oxathiazin-2-yl}-[(S)-1-(2-fluorophenyl)-ethyl]-amine * |
| 49 | HCl | A | 0.911 | 513.7 | {(R)-5-[4-(1-Cyclopropyl-piperidin-4-yl)-benzyl]-6,6-dimethyl-4,4-dioxo-5,6-dihydro-4H-4lambda6-[1,4,3]oxathiazin-2-yl}-[(S)-1-(2-fluorophenyl)-ethyl]-amine * |
| 50 | HCl | B | 6.2 | 487.6 | {(R)-6,6-Dimethyl-5-[4-(1-methyl-piperidin-4-benzyl]-4,4-dioxo-5,6-dihydro-4H-4lambda6-[1,4,3]oxathiazin-2-yl}-[(S)-1-(2-fluorophenyl)-ethyl]-amine * |
| 51 | | B | 8.909 | 487.6 | {(S)-6,6-Dimethyl-5-[4-(1-methyl-piperidin-4-benzyl]-4,4-dioxo-5,6-dihydro-4H-4lambda6-[1,4,3]oxathiazin-2-yl}-[(S)-1-(2-fluorophenyl)-ethyl]-amine * |
| 52 | | A | 0.874 | 476.6 | N-(4-{(R)-2-[(S)-1-(2-fluorophenyl)-ethylamino]-dimethyl-4,4-dioxo-5,6-dihydro-4H-4lambda6-[1,4,3]oxathiazin-5-ylmethyl}-phenyl)-N',N',-dimethyl-ethane-1,2-diamine * |

| Example | CHEMISTRY | Method | Retention time | Molar mass (g/mol) | Name |
|---|---|---|---|---|---|
| 53 | SAR248 (structure) HCl | A | 0.886 | 529.7 | {(S)-6,6-Dimethyl-5-[4-(1-oxetan-3-yl-piperidin-4-yl)-benzyl]-4,4-dioxo-5,6-dihydro-4H-4lambda6-[1,4,3]oxathiazin-2-yl}-[(S)-1-(2-fluorophenyl)-ethyl]-amine * |
| 54 | (structure) HCl | A | 0.81 | 514.7 | [5-(1'-Cyclopropyl-1',2',3',4',5',6'-hexahydro-[2,4']bipyridinyl-5-ylmethyl)-6,6-dimethyl-4,4-dioxo-5,6-dihydro-4H-4lambda6-[1,4,3]oxathiazin-2-yl]-[(S)-1-(2-fluorophenyl)-ethyl]-amine |
| 55 | (structure) H Cl | A | 0.881 | 477.6 | {(S)-5-[4-(2-Amino-2-methyl-propoxy)-benzyl]-6,6-dimethyl-4,4-dioxo-5,6-dihydro-4H-4lambda6-[1,4,3]oxathiazin-2-yl}-[(S)-1-(2-fluorophenyl)-ethyl]-amine * |
| 56 | (structure) | A | 0.747 | 530.7 | [6,6-Dimethyl-5-(1'-oxetan-3-yl-1',2',3',4',5',6'-hexahydro-[2,4']bipyridinyl-5-ylmethyl)-4,4-dioxo-5,6-dihydro-4H-4lambda6-[1,4,3]oxathiazin-2-yl]-[(S)-1-(2-fluorophenyl)-ethyl]-amine |
| 57 | (structure) | A | 0.784 | 531.7 | {5-[6-(4-tert-Butyl-piperazin-1-yl)-pyridin-ylmethyl]-6,6-dimethyl-4,4-dioxo-5,6-dihydro-4H-4lambda6-[1,4,3]oxathiazin-2-yl}-[(S)-1-(2-fluorophenyl)-ethyl]-amine |

\* isomerically pure compound
\*\* trans compound

Chromatography Methods:
Method A
Column: YMC J' spere ODS H80, 80 Å, S-4 μm, 20×2.1 mm
Eluent: 0 min 90% $H_2O$ (0.05% TFA)—1.9 min 95% acetonitrile—2.4 min 95% acetonitrile—2.45 min 10% acetonitrile (30° C., flow rate 1 ml/min)

The efficacy of the compounds was tested as follows:
Enzymatic 11Beta-HSD1 Test:

To measure the activity of the compounds, an SPA-based detection method (Solly et al. 2005) was employed. First of all, 20 μl of the human 11β-HSD1 microsome fraction (0.2 μg of protein), prepared in 50 mM HEPES, 0.1% BSA (w/v), were applied to a plate with 384 wells. The test compounds (0.09 µl) were applied to the assay plate in 100% DMSO. The reaction was started by addition of 20 µl of [1,2-$^3$H]-cortisone (0.1 µCi/100 mM) in assay buffer comprising 25 mM HEPES, 100 mM KCl, 5 mM NaCl, 2 mM $MgCl_2$ and 0.25 mM NADPH. The plate was agitated at 37° C. for 1 hour. At the same time, a stop solution comprising 20 mg/ml SPA-PVT beads, 1.6 mg/ml monoclonal cortisol antibody and 0.01 mM SSR110887 (inhibitor from the Biovitrium patent) in 50 mM HEPES, 1 M NaCl and 1 M KCl was stirred at room temperature. To stop the reaction, 25 µl of the stop solution were added to each well. The plate was agitated gently at room temperature for 1 further hour and then centrifuged at 500 $g_{av}$ for 1 min, in order that the SPA beads could settle out. The plate was then read in a Wallac-1450-Microbeta unit with a standard SPA program (counting time 1 min/well). The comparative compound was glycyrrhetinic acid.

Protein and radioactive substrate were dispensed with a Biomek FX unit (Beckman Coulter) for handling liquids. The test compounds were added with a Cybi-Well equipped with a 90 nl pin tool (CyBio).

Lit.: Solly S, Mundt S S, Zokian H J, Juy-Fang Ding G, Hermanowski-Vosatka A, Strulovici B and Zheng W. High-throughput screening of 11β-Hydroxysteroid dehydrogenase type 1 in scintillation proximity format. Assay Drug Dev Technol 2005; 3:377-384.

TABLE 2

| Biological activity | |
|---|---|
| Example | $IC_{50}$ (nM) |
| 1 | 5 |
| 2 | 7 |
| 3 | 4 |
| 4 | 3 |
| 5 | 5 |
| 6 | 6 |
| 7 | 12 |
| 8 | 7 |
| 9 | 5 |
| 10 | 4 |
| 11 | 8 |
| 12 | 4 |
| 13 | 6 |
| 14 | 4 |
| 15 | 10 |
| 16 | 6 |
| 17 | 4 |
| 18 | 5 |
| 19 | 4 |
| 20 | 5 |
| 21 | 5 |
| 22 | 7 |
| 23 | 17 |
| 25 | 20 |
| 26 | 16 |
| 27 | 5 |
| 28 | 9 |
| 29 | 7 |
| 30 | 29 |
| 31 | 17 |
| 32 | 32 |
| 33 | 30 |
| 34 | 8 |
| 35 | 11 |
| 36 | 38 |
| 37 | 37 |
| 38 | 7 |
| 39 | 17 |
| 40 | 25 |
| 41 | 32 |
| 42 | 5 |
| 43 | 11 |

TABLE 2-continued

| Biological activity | |
|---|---|
| Example | $IC_{50}$ (nM) |
| 44 | 5 |
| 45 | 44 |
| 50 | 52 |
| 51 | 6 |
| 52 | 62 |
| 53 | 9 |
| 55 | 8 |
| 56 | 24 |

It can be inferred from the test data that the compounds of the formula I inhibit 11beta-HSD1 (11beta-hydroxysteroid dehydrogenase type 1), and are thus of good suitability for treatment of hyperglycemia, insulin resistance, diabetes, obesity, lipid metabolism disorders and other diseases.

The preparation of some examples is described in detail hereinafter; the remaining compounds of the formula I were obtained analogously: Experimental:

Separation of 5-(4-bromobenzyl)-2-methoxy-6,6-dimethyl-5,6-dihydro-[1,4,3]oxathiazine 4,4-dioxide into the two chiral compounds was effected by means of high-pressure liquid chromatography:

Column: Chiralcel OJ/H58; flow rate 1 ml/min; ethanol: methanol 1:1. The column was preconditioned with diethylamine. The retention times were 5.05 minutes and 6.16 minutes.

N-[1-(2-Chloro-3-fluorophenyl)meth-(E)-ylidene]-2-methylpropane-2-sulfinamide

2-Chloro-3-fluorobenzaldehyde (2.5 g) and (R)-(+)-2-methyl-2-propanesulfinamide were dissolved in dichloromethane (50 ml), and then titanium(IV) isopropoxide (23.6 ml) was added. The mixture was heated for three hours under reflux, then poured onto ice (150 g) and stirred vigorously for ten minutes. The mixture was filtered through kieselguhr and the filtrate was extracted with dichloromethane (3×50 ml). The organic phase was dried ($Na_2SO_4$), filtered and concentrated under reduced pressure. The product (4 g) was used further without further purification.

The following compounds were prepared in the same way:

N-[1-(2,4-Difluorophenyl)meth-(E)-ylidene]-2-methylpropane-2-sulfinamide

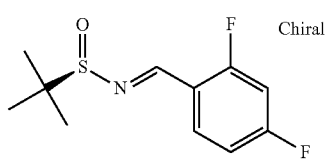 [SMILES: CC(C)(C)[S@@](=O)/N=C/c1ccc(F)cc1F]

3-Amino-3-(2,5-difluorophenyl)propionic acid

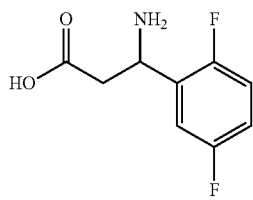 [SMILES: NC(CC(=O)O)c1cc(F)ccc1F]

A solution of 2,5-difluorobenzaldehyde (5 g), malonic acid (3.66 g) and ammonium acetate (5.42 g) in ethanol (50 ml) was heated under reflux for six hours. The mixture was cooled and left to stand overnight. The crystals formed were filtered off and washed with ethanol (5 ml).

The product (2.94 g) was used without further purification.
The following compounds were prepared in the same way:
3-Amino-3-(5-fluoro-2-methylphenyl)propionic acid

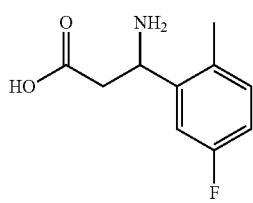

(S)-3-(2-Chloro-3-fluorophenyl)-3-((R)-2-methylpropane-2-sulfinylamino)propionic acid methyl ester

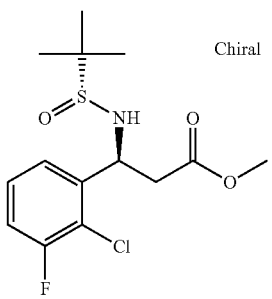 [SMILES: COC(=O)C[C@H](N[S@](=O)C(C)(C)C)c1cccc(F)c1Cl]

To diisopropylamine (4.13 ml), dissolved in THF (200 ml), was slowly added dropwise 1.6 N butyllithium (17.55 ml) at 0° C., and then the mixture was stirred for thirty minutes. Subsequently, the mixture was cooled to 75° C. and methyl acetate (2.13 ml) dissolved in THF (5 ml) was added, and the mixture was stirred for a further thirty minutes. Then chlorotitanium triisopropoxide (56.15 ml, 1 molar in hexane) was added dropwise at the same temperature and the mixture was stirred again for thirty minutes. N-[1-(2-Chloro-3-fluorophenyl)meth-(E)-ylidene]-2-methylpropane-2-sulfinamide was dissolved in THF (10 ml) and added dropwise at 75° C., and the mixture was stirred at the same temperature for three hours. The mixture was poured onto cold saturated ammonium chloride solution and admixed with ethyl acetate, and stirred for fifteen minutes. The phase mixture was then clarified using kieselguhr, the organic phase was removed and the aqueous phase was extracted with ethyl acetate (2×50 ml). The combined organic phases were dried ($Na_2SO_4$), filtered and concentrated. The residue was purified by chromatography (silica gel 40-63 μm, ethyl acetate). This gave the product (4.1 g) with a de of 72% by NMR.

The following compounds were prepared in the same way:
(S)-3-(2,4-Difluorophenyl)-3-((R)-2-methylpropane-2-sulfinylamino)propionic acid methyl ester

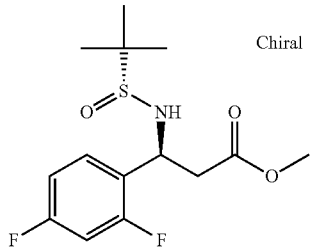 [SMILES: COC(=O)C[C@H](N[S@](=O)C(C)(C)C)c1ccc(F)cc1F]

3-Amino-3-(2,5-difluorophenyl)propionic acid ethyl ester

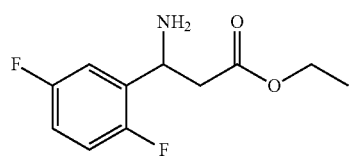 [SMILES: CCOC(=O)CC(N)c1cc(F)ccc1F]

Acetyl chloride (4 ml) was added dropwise at room temperature to a round-bottom flask containing ethanol (50 ml). 3-Amino-3-(2,5-difluorophenyl)propionic acid (2.94 g) was added to the ethanolic hydrochloric acid solution thus prepared, and the mixture was stirred at 50° C. for three hours. Subsequently, the mixture was concentrated under reduced pressure, and the residue was admixed with 1N sodium hydroxide solution (100 ml) and extracted immediately with dichloromethane (3×50 ml). The combined organic phases were dried ($Na_2SO_4$), filtered and concentrated. The product (3.2 g) was used without further purification.

The following compounds were prepared in the same way:
(S)-3-Amino-3-(5-fluoro-2-methylphenyl)propionic acid ethyl ester

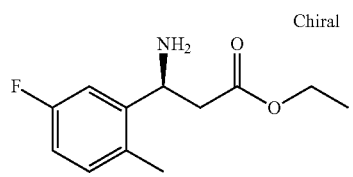 [SMILES: CCOC(=O)C[C@H](N)c1cc(F)ccc1C]

(S)-3-Amino-3-(2,5-difluorophenyl)propionic acid methyl ester

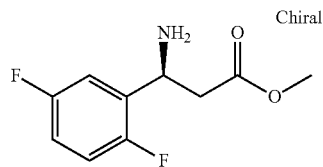

(S)-3-Amino-3-(5-fluoro-2-methylphenyl)propionic acid methyl ester

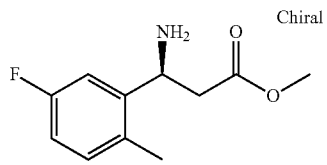

(S)-3-Amino-3-(2,5-difluorophenyl)propionic acid

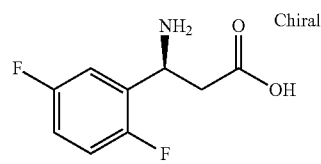 [SMILES: N[C@@H](CC(=O)O)c1cc(F)ccc1F]

3-Amino-3-(2,5-difluorophenyl)propionic acid ethyl ester (3 g) was emulsified in water (pH=9.2) and admixed with potassium dihydrogenphosphate (5 mg) (pH=8.5). After addition of Amano Lipase PS (150 mg), the mixture was stirred overnight. The pH remains at 7.5. The mixture was then admixed with water (30 ml) and filtered through kieselguhr and washed several more times with water. The aqueous phase was then extracted with dichloromethane (3×30 ml), and the organic phase was dried (Na2SO4) and concentrated. This gave the product (1.3 g) with an ee=90% by HPLC.

The following compounds were prepared in the same way:
(S)-3-Amino-3-(5-fluoro-2-methylphenyl)propionic acid

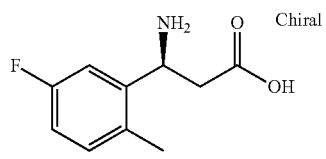

(S)-3-Amino-3-(3-chloro-2-fluorophenyl)propionic acid methyl ester

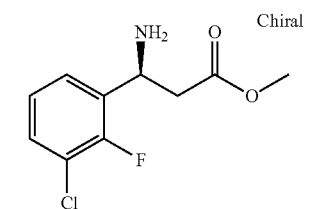

To a solution of acetyl chloride (4 ml) in methanol (50 ml) was added (S)-3-(2-chloro-3-fluorophenyl)-34(R)-2-methylpropane-2-sulfinylamino)propionic acid methyl ester (4.1 g) dissolved in methanol (10 ml) at room temperature. After one hour, the mixture was concentrated, taken up in dichloromethane (100 ml) and washed with 1N sodium hydroxide solution (100 ml). The aqueous phase was washed twice with dichloromethane. The combined organic phases were dried (Na₂SO₄), filtered and concentrated. The residue (2.8 g) was used without further purification.

The following compounds were prepared in the same way:
(S)-3-Amino-3-(2,4-difluorophenyl)propionic acid methyl ester

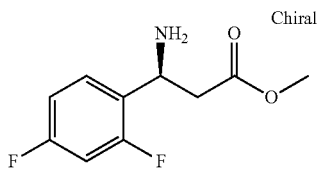

(S)-3-Amino-3-(2-chloro-3-fluorophenyl)propan-1-ol

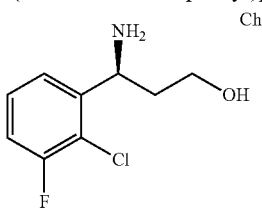

To a solution of 1N lithium aluminum hydride (24.2 ml in THY) in THF (20 ml) was added dropwise, at 0° C., (S)-3-amino-3-(3-chloro-2-fluorophenyl)propionic acid methyl ester (2.8 g) dissolved in THF (5 ml), and the mixture was stirred for one hour. Then the mixture was added dropwise to saturated sodium chloride solution (50 ml) and stirred for five minutes. Then 1N sodium hydroxide solution (50 ml) was added and the mixture was stirred for a further five minutes. The mixture was then extracted with ethyl acetate (3×50 ml), dried (Na₂SO₄) and concentrated. The product (2.23 g) was used without further purification.

The following compounds were prepared in the same way:
(S)-3-Amino-3-(2,4-difluorophenyl)propan-1-ol

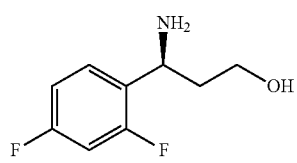

(S)-3-Amino-3-(2,5-difluorophenyl)propan-1-ol

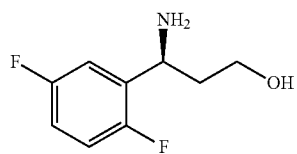

(S)-3-Amino-3-(5-fluoro-2-methylphenyl)propan-1-ol

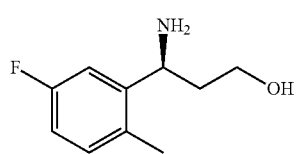

(S)-3-(tert-Butyldimethylsilanyloxy)-1-(5-chloro-2-fluorophenyl)propylamine

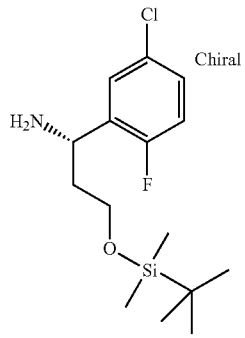 [SMILES: CC(C)(C)[Si](C)(C)OCC[C@H](N)c1cc(Cl)ccc1F]

The 1N lithium aluminum hydride (100 ml) in THF was initially charged and (S)-3-amino-3-(5-chloro-2-fluorophenyl)propionic acid methyl ester (insoluble in THF) was added in portions while cooling with ice. The cooling was then removed and the mixture was stirred for 1 hour. Subsequently 5 ml of $H_2O$ and 5 ml of 5M NaOH were added dropwise under ice and 15 ml of $H_2O$ were added cautiously, then the mixture was stirred for 4 days. The precipitate was filtered through Celite and washed through with THF (3×30 ml), then the filtrate was concentrated. The residue was taken up with dichloromethane (50 ml) and dried over MgSO4, filtered and concentrated by rotary evaporation. The residue (2.95 g) was dissolved in dichloromethane (20 ml) and admixed with DIPEA and with t-butyldimethylchlorosilane in portions. The mixture was stirred at 25° C. overnight.

The mixture was washed twice with 50 ml 5% $NaHCO_3$ solution, and the organic phase was dried over $Na_2SO_4$ and concentrated. Final weight: 5.16 g. Then purification was effected with the aid of a Flashmaster. 70 g column (normal phase); fraction size: 20 ml; flow rate: 19 ml/min Fractions 17-40 combined. This gave the product (3.64 g) with a molecular weight of 317.9 ($C_{15}H_{26}ClFNOSi$); MS (ESI): 318 (M+H+).

(S)-3-(tert-Butyldimethylsilanyloxy)-1-phenylpropylamine

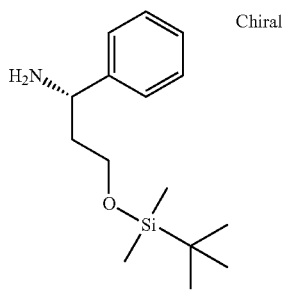 [SMILES: CC(C)(C)[Si](C)(C)OCC[C@H](N)c1ccccc1]

S-3-Amino-3-phenyl-1-propanol (4.72 g) was dissolved in dichloromethane (60 ml), admixed with triethylamine (6.36 g) and tert-butyldimethylchlorosilane (4.1 g), and the mixture was stirred at room temperature for 3 hours. Then it was washed with water (3×50 ml) and dried using a phase separator cartridge. This gave the product with a molecular weight of 265.5 g/mol (C15H27NOSi), MS (ESI): (M+H+) 266 g/mol.

The following compounds were prepared in the same way:

(S)-3-(tert-Butyldimethylsilanyloxy)-1-(2-fluorophenyl)propylamine

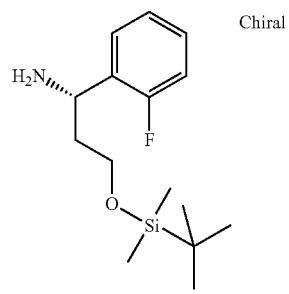 [SMILES: CC(C)(C)[Si](C)(C)OCC[C@H](N)c1ccccc1F]

(S)-3-(tert-Butyldimethylsilanyloxy)-1-(3-chlorophenyl)propylamine

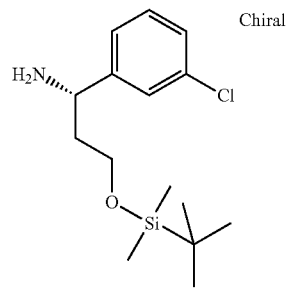 [SMILES: CC(C)(C)[Si](C)(C)OCC[C@H](N)c1cccc(Cl)c1]

(S)-3-(tert-Butyldimethylsilanyloxy)-1-(4-chlorophenyl)propylamine

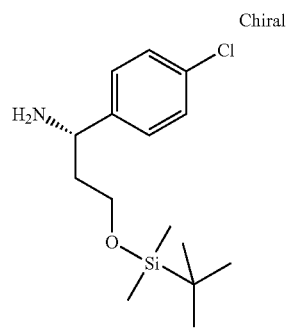 [SMILES: CC(C)(C)[Si](C)(C)OCC[C@H](N)c1ccc(Cl)cc1]

(S)-3-(tert-Butyldimethylsilanyloxy)-1-(2-chlorophenyl)propylamine

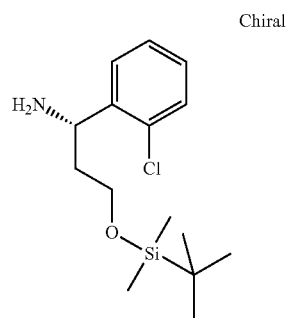

(S)-3-(tert-Butyldimethylsilanyloxy)-1-(2-chloro-3-fluorophenyl)propylamine

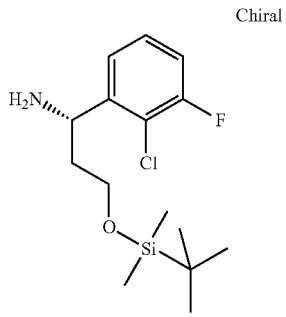 [SMILES: CC(C)(C)[Si](C)(C)OCC[C@H](N)c1cccc(F)c1Cl]

(S)-3-(tert-Butyldimethylsilanyloxy)-1-(2,4-difluorophenyl)propylamine

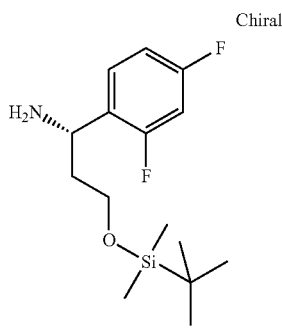 [SMILES: CC(C)(C)[Si](C)(C)OCC[C@H](N)c1ccc(F)cc1F]

(S)-3-(tert-Butyldimethylsilanyloxy)-1-(2,5-difluorophenyl)propylamine

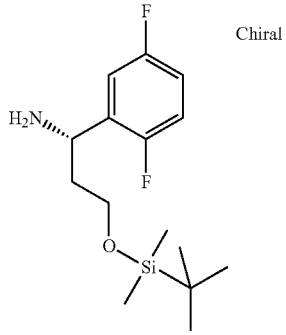 [SMILES: CC(C)(C)[Si](C)(C)OCC[C@H](N)c1cc(F)ccc1F]

(S)-3-(tert-Butyldimethylsilanyloxy)-1-(5-fluoro-2-methylphenyl)propylamine

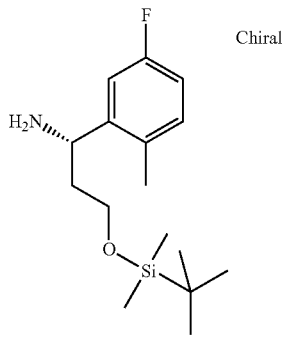 [SMILES: Cc1ccc(F)cc1[C@@H](N)CCO[Si](C)(C)C(C)(C)C]

2-(4-Bromobenzyl)-2-methylmalonic acid diethyl ester

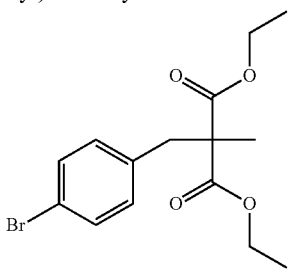

60% sodium hydride in mineral oil (6.4 g) were suspended in dry DMF (100 ml) and then, at 0° C., methylmalonic acid diethyl ester (25.2 g) was slowly added dropwise. After evolution of gas had ended, 4-bromobenzyl bromide (43.7 g) dissolved in 40 ml of DMF was added dropwise. Then the mixture was stirred at 100° C. for one hour. The suspension formed was cooled, diluted with ethyl acetate (100 ml) and washed with 5% $Na_2SO_3$ solution (3×100 ml). The organic phase was dried ($Na_2SO_4$) and concentrated under reduced pressure. The clear residue (49.6 g) was used further without further workup.

2-(4-Bromobenzyl)-2-methylmalonic acid

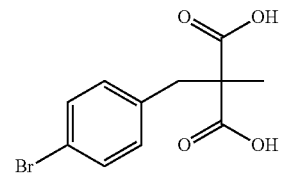

2-(4-Bromobenzyl)-2-methylmalonic acid diethyl ester (49.5 g) was dissolved in ethanol (100 ml) and water (100 ml), and the mixture was admixed with sodium hydroxide solution (28.8 g). The solution was heated under reflux overnight. Subsequently, it was poured onto water (200 ml) and washed with dichloromethane (2×100 ml). The mixture was then poured into conc. hydrochloric acid (100 ml) and ice (200 g) and extracted with ethyl acetate (2×150 ml). The organic phase was then dried with $MgSO_4$, filtered and concentrated under reduced pressure. The solid residue (41.5 g) was used further without further workup.

3-(4-Bromophenyl)-2-methylpropionic acid ethyl ester

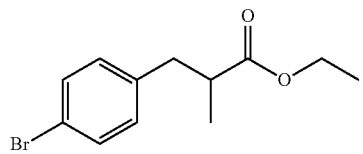

2-(4-Bromobenzyl)-2-methylmalonic acid (41.5 g) was heated to 150° C. in a flask for 45 minutes. The oil bath was then removed, the clear oil was admixed cautiously with ethanol (70 g) and oleum (4 g), and the mixture was heated under reflux for four hours. The ethanol was removed under reduced pressure. The oily residue was admixed with ethyl acetate (100 ml) and the organic phase was washed with dilute ammonia solution (2×100 ml), dried ($MgSO_4$), filtered and concentrated under reduced pressure. The product was purified by distillation at 0.26 mbar at 100° C.

This gave the product (28 g) with a molecular weight of 271.1 g/mol ($C_{12}H_{15}BrO_2$), MS (ESI): (M+H+) 272 g/mol.

4-(4-Bromophenyl)-2,3-dimethylbutan-2-ol

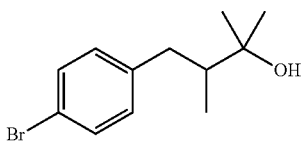

3-(4-Bromophenyl)-2-methylpropionic acid ethyl ester (28 g) was added dropwise with cooling to ethylmagnesium bromide (25.2 g) dissolved in diethyl ether (150 ml). On completion of addition, the cooling was removed and the mixture was left to stand overnight. The solution was then admixed with conc. ammonium chloride solution (10 ml) and water (5 ml). The diethyl ether was removed on a rotary evaporator and the residue was admixed with THF (100 ml) and the solution was dried with $MgSO_4$. The $MgSO_4$ was filtered off through Celite and the solution was concentrated to a high concentration and left to stand overnight. The crystals formed (13.2 g) were filtered off with suction and used further without further workup.

1-Bromo-4-(2,3-dimethylbut-2-enyl)benzene

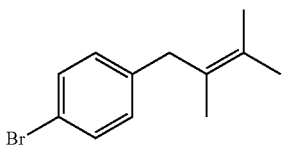

4-(4-Bromophenyl)-2,3-dimethylbutan-2-ol was added in portions to polyphosphoric acid at 100° C., and then the mixture was stirred at this temperature for one hour. After cooling, ice was added (50 g) and extraction was effected with ethyl acetate (3×50 ml). The organic phase was washed with $NaHCO_3$ solution (50 ml), dried ($MgSO_4$) and concentrated. The residue was first purified by chromatography with heptane and then distilled (0.04 mbar, 58° C.).

This gave the product (8.7 g). Characterization was effected by means of NMR.

1-Bromo-4-(3-methyl-but-2-enyl)benzene

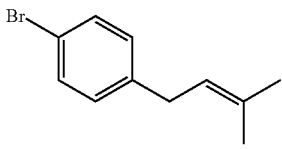

Zimmermann, H. et al. Journal of Organic Chemistry 49; 17; 1984; 3069-3083.

5-Benzyl-2-methoxy-6,6-dimethyl-5,6-dihydro-[1,4,3]oxathiazine 4,4-dioxide

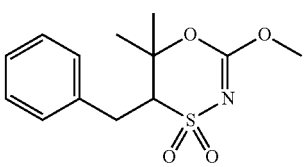 [SMILES: COC1=NS(=O)(=O)C(Cc2ccccc2)C(C)(C)O1]

Chlorosulfonyl isocyanate (4.2 g) was initially charged in dichloromethane, and methanol (1.2 ml) was added dropwise while cooling with ice. Subsequently, the mixture was stirred for 10 minutes and then the solvent was removed under reduced pressure. After addition of THF (30 ml), the mixture was cooled to −78° C., and sodium hydride was added under argon (vigorous evolution of gas). The cooling was removed and (3-methylbut-2-enyl)benzene (4.34 g) was added in one portion and then the mixture was heated to 35° C. After 30 minutes, the THF was removed, and the residue was taken up with ethyl acetate (50 ml) and washed with water (3×30 ml). The organic phase was dried ($Na_2SO_4$) and concentrated. The crude product (7.07 g) was purified by preparative HPLC.

This gave the product (0.29 g) with a molecular weight of 283.3 g/mol ($C_{13}H_{17}NO_4S$), MS (ESI): (M+H+) 284 g/mol.

The following compounds were prepared in the same way:

5-(4-Bromobenzyl)-2-methoxy-5,6,6-trimethyl-5,6-dihydro-[1,4,3]oxathiazine 4,4-dioxide

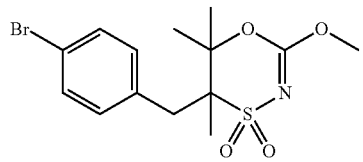 [SMILES: COC1=NS(=O)(=O)C(C)(Cc2ccc(Br)cc2)C(C)(C)O1]

5-(4-Bromobenzyl)-2-methoxy-6,6-dimethyl-5,6-dihydro-[1,4,3]oxathiazine 4,4-dioxide

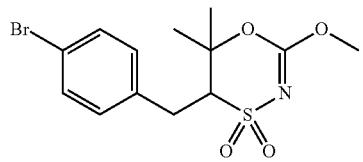 [SMILES: COC1=NS(=O)(=O)C(Cc2ccc(Br)cc2)C(C)(C)O1]

[5-(4-Bromobenzyl)-6,6-dimethyl-4,4-dioxo-5,6-dihydro-4H-4lambda6-[1,4,3]oxathiazin-2-yl]-[(S)-3-(tert-butyldimethylsilanyloxy)-1-(2-fluorophenyl)propyl]amine

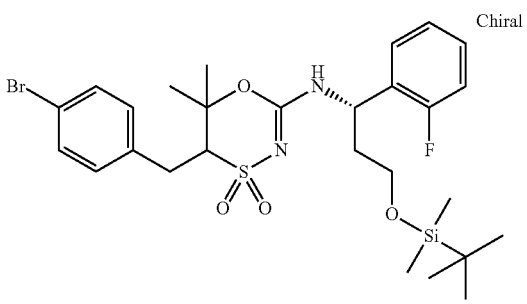 [SMILES: CC1(C)OC(N[C@@H](CCO[Si](C)(C)C(C)(C)C)c2ccccc2F)=NS(=O)(=O)C1Cc1ccc(Br)cc1]

5-(4-Bromobenzyl-2-methoxy-6,6-dimethyl-5,6-dihydro-[1,4,3]oxathiazine 4,4-dioxide (0.33 g) and (S)-3-(tert-butyldimethylsilanyloxy)-1-(2-fluorophenyl)propylamine (0.31 g) were dissolved in dichloromethane (2 ml) and stirred under a gentle argon stream until crystals formed. Then solvent was added again and blown off again gradually until no further crystals formed. The oil was then left to stand overnight. The residue was purified by chromatography with heptane/ethyl acetate. This gave the desired product (250 mg).

The following compounds were prepared in the same way:

[5-(6-Chloropyridin-3-ylmethyl)-6,6-dimethyl-4,4-dioxo-5,6-dihydro-4H-4lambda6-[1,4,3]oxathiazin-2-yl]-[(S)-1-(2-fluorophenyl)ethyl]amine

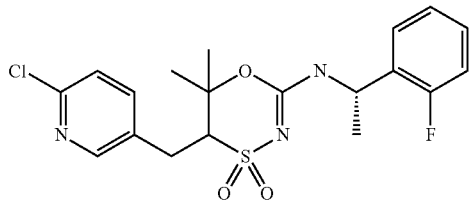 [SMILES: C[C@H](NC1=NS(=O)(=O)C(Cc2ccc(Cl)nc2)C(C)(C)O1)c1ccccc1F]

(5-Benzyl-6,6-dimethyl-4,4-dioxo-5,6-dihydro-4H-4lambda6-[1,4,3]oxathiazin-2-yl)-(4-fluorobicyclo[2.2.2]oct-1-yl)amine

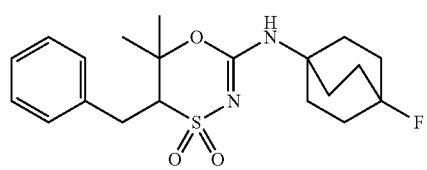 [SMILES: CC1(C)OC(NC23CCC(F)(CC2)CC3)=NS(=O)(=O)C1Cc1ccccc1]

[5-(4-Bromobenzyl)-5,6,6-trimethyl-4,4-dioxo-5,6-dihydro-4H-4lambda6-[1,4,3]oxathiazin-2-yl]-[(S)-1-(2-fluorophenyl)ethyl]amine

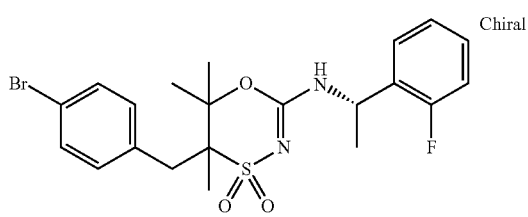 [SMILES: C[C@H](NC1=NS(=O)(=O)C(C)(Cc2ccc(Br)cc2)C(C)(C)O1)c1ccccc1F]

[5-(4-Bromobenzyl)-6,6-dimethyl-4,4-dioxo-5,6-dihydro-4H-4lambda6-[1,4,3]oxathiazin-2-yl]-[(S)-1-(2-fluorophenyl)ethyl]amine

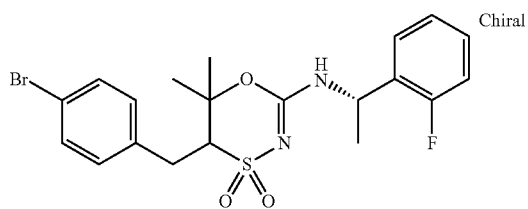 [SMILES: C[C@H](NC1=NS(=O)(=O)C(Cc2ccc(Br)cc2)C(C)(C)O1)c1ccccc1F]

[5-(4-Bromobenzyl)-6,6-dimethyl-4,4-dioxo-5,6-dihydro-4H-4lambda6-[1,4,3]oxathiazin-2-yl]-[(S)-1-(2-chlorophenyl)ethyl]amine

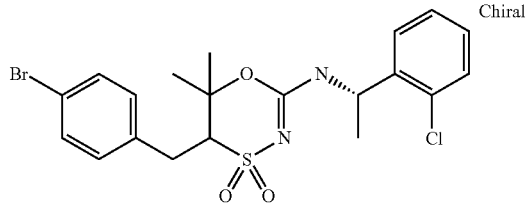 [SMILES: C[C@H](NC1=NS(=O)(=O)C(Cc2ccc(Br)cc2)C(C)(C)O1)c1ccccc1Cl]

5-(6-Chloropyridin-3-ylmethyl)-2-methoxy-6,6-dimethyl-5,6-dihydro-[1,4,3]oxathiazine 4,4-dioxide

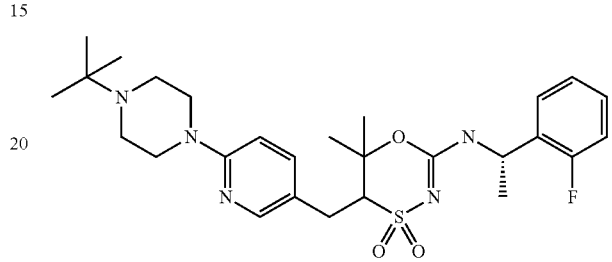

{5-[6-(4-tert-Butylpiperazin-1-yl)pyridin-3-ylmethyl]-6,6-dimethyl-4,4-dioxo-5,6-dihydro-4H-4lambda6-[1,4,3]oxathiazin-2-yl}-[(S)-1-(2-fluorophenyl)ethyl]amine

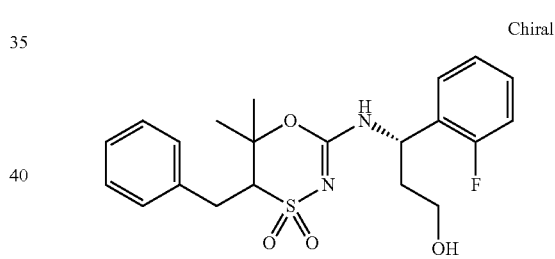

(S)-3-(5-Benzyl-6,6-dimethyl-4,4-dioxo-5,6-dihydro-4H-4lambda6-[1,4,3]oxathiazin-2-ylamino)-342-fluorophenyl)propan-1-ol 5-Benzyl-2-methoxy-6,6-dimethyl-5,6-dihydro-[1,4,3]oxathiazine 4,4-dioxide (0.2 g) and (S)-3-(tert-butyldimethylsilanyloxy)-1-(2-fluorophenyl)propylamine (0.2 g) were dissolved in dichloromethane (2 ml) and stirred under a gentle argon stream until crystals formed. Then solvent was added again and blown off again gradually until no further crystals formed. The oil was then left to stand overnight. Subsequently, the residue was taken up in methanol (3 ml) and 5 N hydrochloric acid (1.5 ml) and the solution was concentrated under reduced pressure at 40° C. The residue was purified by chromatography with heptane/ethyl acetate.

This gave the product (162 mg) with a molecular weight of 420.5 g/mol ($C_{21}H_{25}FN_2O_4S$), MS (ESI): (M+H+) 421 g/mol.

The following compounds were prepared in the same way:

(S)-3-(5-Benzyl-6,6-dimethyl-4,4-dioxo-5,6-dihydro-4H-4lambda6-[1,4,3]oxathiazin-2-ylamino)-3-(2-chlorophenyl)propan-1-ol

| 71 | 72 |
|---|---|
| 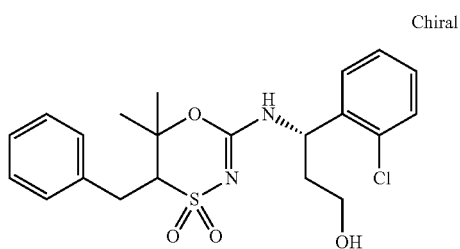 [SMILES: CC1(C)OC(N[C@@H](CCO)c2ccccc2F)=NS(=O)(=O)C1Cc1ccccc1]<br>(S)-3-(5-Benzyl-6,6-dimethyl-4,4-dioxo-5,6-dihydro-4H-4lambda6-[1,4,3]oxathiazin-2-ylamino)-3-(3-chlorophenyl)propan-1-ol | 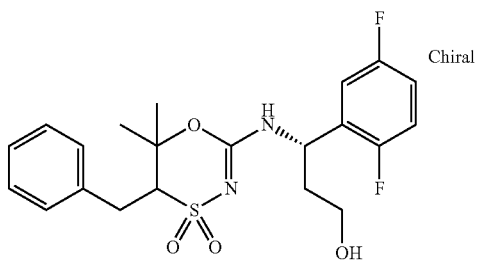<br>(S)-3-(5-Benzyl-6,6-dimethyl-4,4-dioxo-5,6-dihydro-4H-4lambda6-[1,4,3]oxathiazin-2-ylamino)-3-(2-chloro-3-fluorophenyl)propan-1-ol |
| 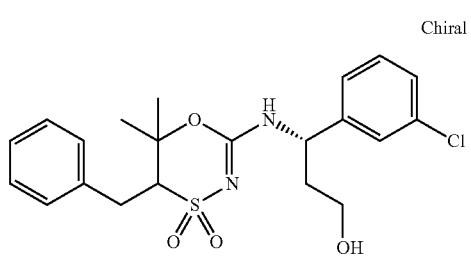 [SMILES: CC1(C)OC(N[C@@H](CCO)c2cccc(Cl)c2)=NS(=O)(=O)C1Cc1ccccc1]<br>(S)-3-(5-Benzyl-6,6-dimethyl-4,4-dioxo-5,6-dihydro-4H-4lambda6-[1,4,3]oxathiazin-2-ylamino)-3-(4-chlorophenyl)propan-1-ol | 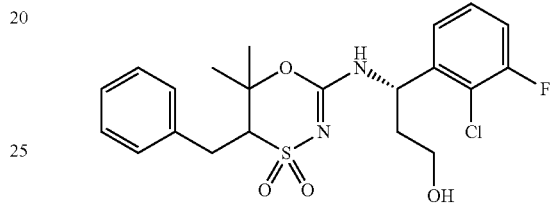<br>(S)-3-(5-Benzyl-6,6-dimethyl-4,4-dioxo-5,6-dihydro-4H-4lambda6-[1,4,3]oxathiazin-2-ylamino)-3-(5-chloro-2-fluorophenyl)propan-1-ol |
| 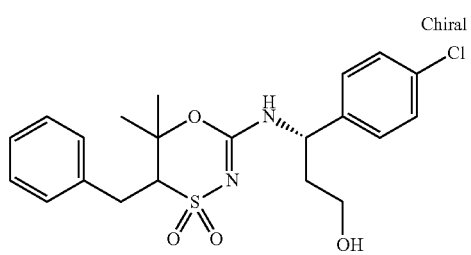 [SMILES: CC1(C)OC(N[C@@H](CCO)c2ccc(Cl)cc2)=NS(=O)(=O)C1Cc1ccccc1]<br>(S)-3-(5-Benzyl-6,6-dimethyl-4,4-dioxo-5,6-dihydro-4H-4lambda6-[1,4,3]oxathiazin-2-ylamino)-3-(2,4-difluorophenyl)propan-1-ol | 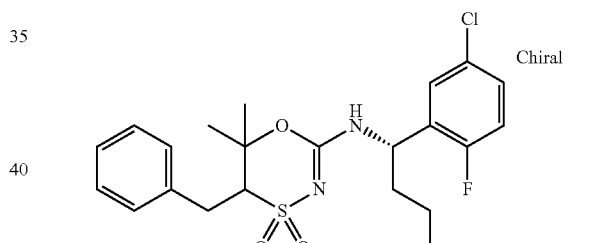<br>(S)-3-(5-Benzyl-6,6-dimethyl-4,4-dioxo-5,6-dihydro-4H-4lambda6-[1,4,3]oxathiazin-2-ylamino)-3-(5-chloro-2-methylphenyl)propan-1-ol |
| 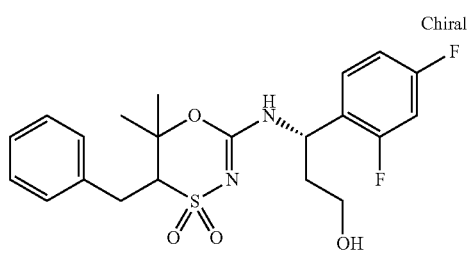 [SMILES: CC1(C)OC(N[C@@H](CCO)c2ccc(F)cc2F)=NS(=O)(=O)C1Cc1ccccc1]<br>(S)-3-(5-Benzyl-6,6-dimethyl-4,4-dioxo-5,6-dihydro-4H-4lambda6-[1,4,3]oxathiazin-2-ylamino)-3-(2,5-difluorophenyl)propan-1-ol | 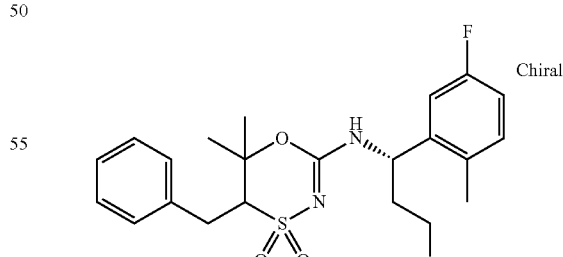<br>(S)-3-[5-(4-Bromobenzyl)-5,6,6-trimethyl-4,4-dioxo-5,6-dihydro-4H-4lambda6-[1,4,3]oxathiazin-2-ylamino]-3-(2-fluorophenyl)propan-1-ol |

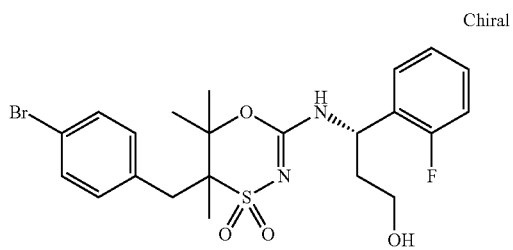 [SMILES: CC1(C)OC(N[C@@H](CCO)c2ccccc2F)=NS(=O)(=O)C1(C)Cc1ccc(Br)cc1]

(S)-3-(5-Biphenyl-3-ylmethyl-6,6-dimethyl-4,4-dioxo-5,6-dihydro-4H-4lambda6-[1,4,3]oxathiazin-2-ylamino)-3-(2-fluorophenyl)propan-1-ol

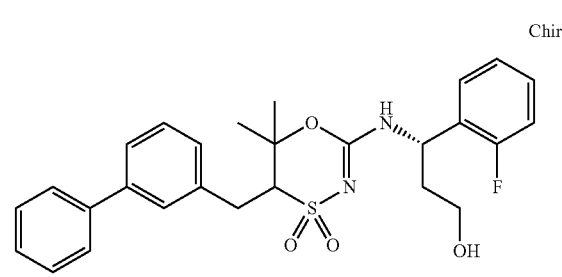

(S)-3-(5-Biphenyl-4-ylmethyl-6,6-dimethyl-4,4-dioxo-5,6-dihydro-4H-4lambda6-[1,4,3]oxathiazin-2-ylamino)-3-(2-fluorophenyl)propan-1-ol

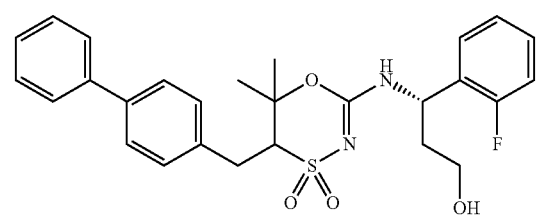

(S)-3-{6,6-Dimethyl-4,4-dioxo-5-[4-(5-trifluoromethyl-pyridin-2-yl)-benzyl]-5,6-dihydro-4H-4lambda6-[1,4,3]oxathiazin-2-ylamino}-3-(2-fluorophenyl)propan-1-ol

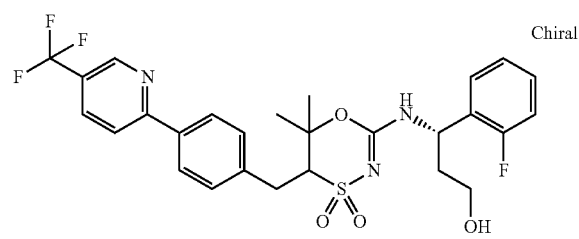 [SMILES: CC1(C)OC(N[C@@H](CCO)c2ccccc2F)=NS(=O)(=O)C1Cc1ccc(-c2ccc(C(F)(F)F)cn2)cc1]

(S)-3-(6,6-Dimethyl-5-naphthalen-1-ylmethyl-4,4-dioxo-5,6-dihydro-4H-4lambda6-[1,4,3]oxathiazin-2-ylamino)-3-(2-fluorophenyl)propan-1-ol

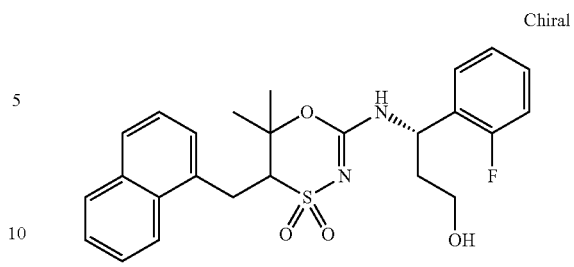

Amino-4-fluorobicyclo[2.2.2]octane

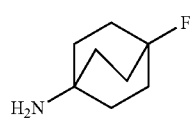

*Journal of Organic Chemistry* 1982, 47(15), 2951-2957.

(5-Benzyl-5,6,6-trimethyl-4,4-dioxo-5,6-dihydro-4H-4lambda6-[1,4,3]oxathiazin-2-yl)-[(S)-1-(2-fluorophenyl)ethyl]amine

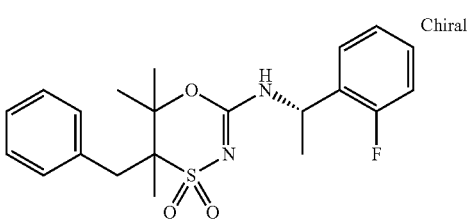 [SMILES: C[C@H](NC1=NS(=O)(=O)C(C)(Cc2ccccc2)C(C)(C)O1)c1ccccc1F]

[5-(4-Bromobenzyl)-5,6,6-trimethyl-4,4-dioxo-5,6-dihydro-4H-4lambda6-[1,4,3]oxathiazin-2-yl]-[(S)-1-(2-fluorophenyl)ethyl]amine (13.5 mg) was dissolved in ethanol and hydrogenated in an autoclave with Pd/C, hydrogen. The palladium was filtered off and the solution was concentrated. This gave the product (10 mg) with a molecular weight of 404.5 g/mol ($C_{21}H_{25}FN_2O_3S$), MS (ESI): (M+H+) 405 g/mol.

N,N-Bis(2,4-dimethoxybenzyl)methanesulfonamide

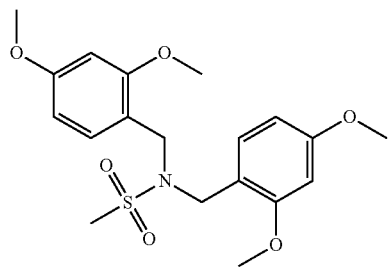 [SMILES: COc1ccc(CN(Cc2ccc(OC)cc2OC)S(C)(=O)=O)c(OC)c1]

To a solution of methanesulfonyl chloride (3.8 g) in dichloromethane (50 ml) was added bis(2,4-dimethoxybenzyl)amine (10 g) in portions at room temperature. The suspension was stirred for another 30 minutes and admixed with water (100 ml), and the organic phase was removed. The aqueous phase was extracted with dichloromethane (2×50 ml). The combined organic phases were dried (Na$_2$SO$_4$), filtered and concentrated under reduced pressure. The residue was purified by normal phase chromatography (dichloromethane). This gave the desired product (10.8 g).

N,N-b is [(2,4-Dimethoxybenzyl)]-2-[4-(5-trifluoromethylpyridin-2-yl)phenyl]ethane sulfonamide

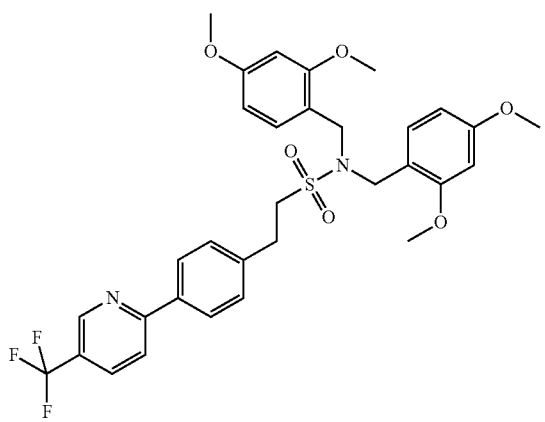 [SMILES: COc1ccc(CN(Cc2ccc(OC)cc2OC)S(=O)(=O)CCc2ccc(-c3ccc(C(F)(F)F)cn3)cc2)c(OC)c1]

To a solution of N,N-bis(2,4-dimethoxybenzyl)methanesulfonamide (1.3 g) in THF (25 ml) was added dropwise, at −78° C., 1.6 N butyllithium in hexane (2.5 ml), and the mixture was stirred for thirty minutes. Subsequently, 2-(4-chloromethylphenyl)-5-trifluoromethylpyridine (1.16 g) was added and the cooling was removed. After one hour, the solvent was removed under reduced pressure, and the residue was taken up in a little ethyl acetate and purified by chromatography (ethyl acetate/heptane). This gave the product (1.1 g) with a molecular weight of 630.6 g/mol (C$_{32}$H$_{33}$F$_3$N$_2$O$_6$S), MS (ESI): (M+H+) 631 g/mol.

The following compounds were prepared in the same way:

N,N-bis(2,4-Dimethoxybenzyl)-2-biphenyl-4-ylethane-sulfonamide

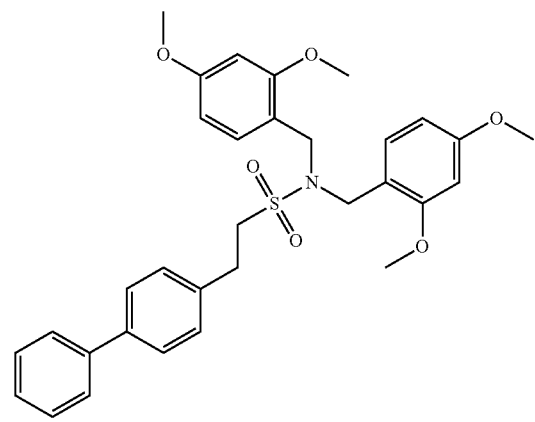 [SMILES: COc1ccc(CN(Cc2ccc(OC)cc2OC)S(=O)(=O)CCc2ccc(-c3ccccc3)cc2)c(OC)c1]

N,N-bis(2,4-Dimethoxybenzyl)-2-biphenyl-3-ylethane-sulfonamide

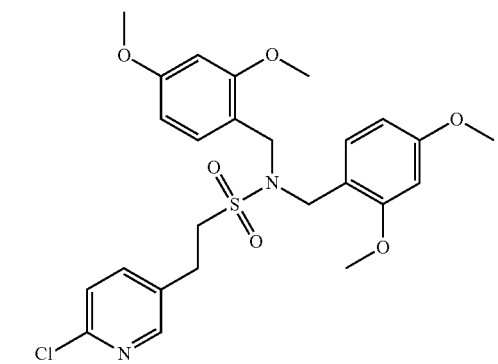 [SMILES: COc1ccc(CN(Cc2ccc(OC)cc2OC)S(=O)(=O)CCc2ccc(Cl)nc2)c(OC)c1]

N,N-bis(2,4-Dimethoxybenzyl)-2-(6-chloropyridin-3-yl)ethanesulfonamide

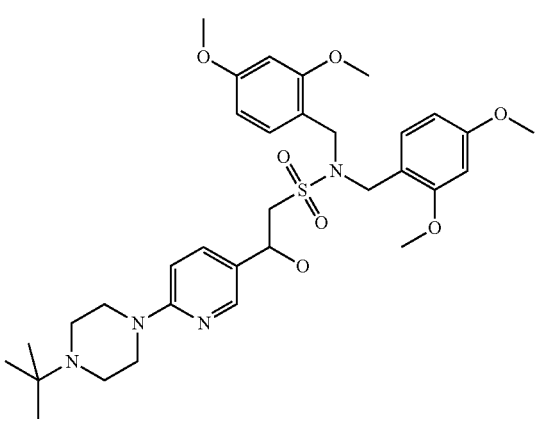 [SMILES: COc1ccc(CN(Cc2ccc(OC)cc2OC)S(=O)(=O)CC(O)c2ccc(N3CCN(C(C)(C)C)CC3)nc2)c(OC)c1]

N,N-bis(2,4-Dimethoxybenzyl)-2-[6-(4-tert-butylpiperazin-1-yl)pyridin-3-yl]-2-hydroxyethanesulfonamide N,N-bis(2,4-Dimethoxybenzyl)-2-[6-(4-tert-butylpiperazin-1-yl)pyridin-3-yl]ethenesulfonamide

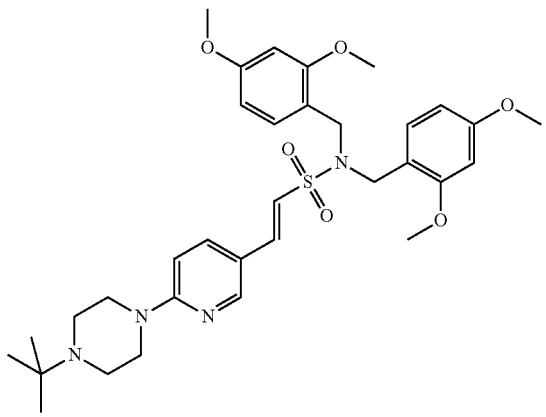 [SMILES: COc1ccc(CN(Cc2ccc(OC)cc2OC)S(=O)(=O)/C=C/c2ccc(N3CCN(C(C)(C)C)CC3)nc2)c(OC)c1]

Methylsulfonyl chloride (0.8 g) was slowly added dropwise to a solution of N,N-bis[(2,4-dimethoxybenzyl)]-2-[6-(4-tert-butylpiperazin-1-yppyridin-3-yl]-2-hydroxyethanesulfonamide (3.75 g) and triethylamine (0.7 g) in methylene chloride (20 ml), and then the solution was stirred at 40° C. for two hours. Then the organic phase was washed (NaCl solution, 50 ml), filtered, dried (Na$_2$SO$_4$) and concentrated. The residue was used without further workup.

N,N-bis(2,4-Dimethoxybenzyl)-2-[6-(4-tert-butylpiperazin-1-yl)pyridin-3-yl]ethanesulfonamide

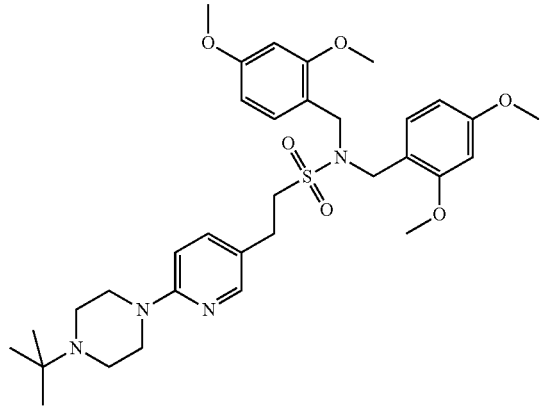 [SMILES: COc1ccc(CN(Cc2ccc(OC)cc2OC)S(=O)(=O)CCc2ccc(N3CCN(C(C)(C)C)CC3)nc2)c(OC)c1]

N,N-bis(2,4-Dimethoxybenzyl)-2-[6-(4-tert-butylpiperazin-1-yl)pyridin-3-yl]ethenesulfonamide was dissolved in ethanol, palladium on charcoal was added, and then the mixture was stirred under a 5 bar hydrogen atmosphere for 24 hours. The palladium was filtered off, the solution was concentrated and the residue was purified by chromatography (EtOAc/heptane).

N-(2,4-Dimethoxybenzyl)-2-phenylethanesulfonamide

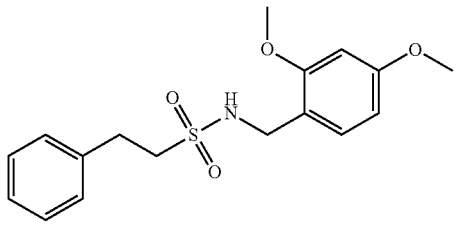 [SMILES: COc1ccc(CNS(=O)(=O)CCc2ccccc2)c(OC)c1]

To a solution of 2-phenylethanesulfonyl chloride (3 g) in dichloromethane (50 ml) was slowly added dropwise, at 0° C., 2,4-dimethoxybenzylamine (5 g) dissolved in dichloromethane (5 ml). The cooling was removed and the mixture was stirred for another two hours. The suspension formed was admixed with water (100 ml) and the organic phase was removed. The organic phase was then washed with 2N hydrochloric acid (100 ml) and saturated sodium hydrogencarbonate solution (100 ml), dried (Na$_2$SO$_4$), filtered and concentrated. This gave the product (5 g), which was used without further workup.

The following compounds were prepared in the same way:

N,N-bis(2,4-Dimethoxybenzyl)-2-(4-chlorophenyl)ethanesulfonamide

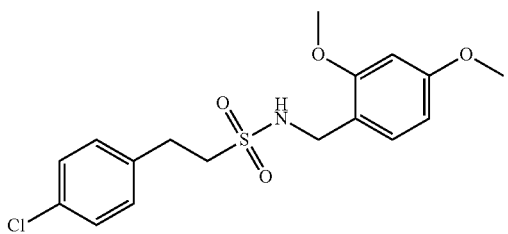 [SMILES: COc1ccc(CNS(=O)(=O)CCc2ccc(Cl)cc2)c(OC)c1]

N,N-bis(2,4-Dimethoxybenzyl)-2-naphthalen-1-ylethanesulfonamide

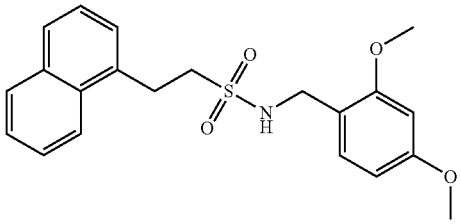 [SMILES: COc1ccc(CNS(=O)(=O)CCc2cccc3ccccc23)c(OC)c1]

3-Hydroxy-3-methyl-1-[4-(5-trifluoromethyl-pyridin-2-yl)phenyl]butane-2-sulfonamide

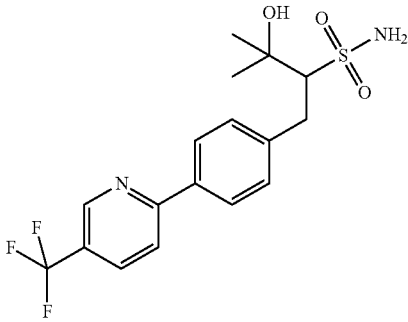 [SMILES: CC(C)(O)C(Cc1ccc(-c2ccc(C(F)(F)F)cn2)cc1)S(N)(=O)=O]

To a solution of N,N-bis(2,4-dimethoxybenzyl)-2-[4-(5-trifluoromethylpyridin-2-yl)phenyl]ethanesulfonamide (1.1 g) in THF (10 ml) was added dropwise, at −78° C., 1.8 N phenyllithium in hexane (2.9 ml), then the mixture was warmed up again to −20° C. for 5 minutes and then cooled again to −78° C. After addition of the acetone (0.9 ml), the mixture was stirred at this temperature for another fifteen minutes and then quenched with trifluoroacetic acid (1 ml). The solution was concentrated under reduced pressure, taken up in dichloromethane (10 ml) and admixed with trifluoroacetic acid (3 ml), and stirred overnight. The solution was concentrated and chromatographed without further workup (dichloromethane/methanol). This gave the product (0.29 g) with a molecular weight of 388.4 g/mol ($C_{17}H_{19}F_3N_2O_3S$), MS (ESI): (M+H+) 389 g/mol.

The following compounds were prepared in the same way:
1-Biphenyl-4-yl-3-hydroxy-3-methylbutane-2-sulfonamide

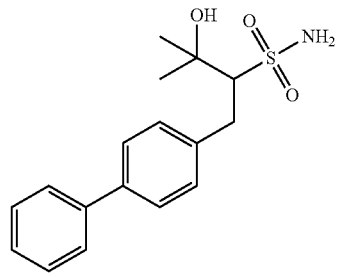 [SMILES: CC(C)(O)C(Cc1ccc(-c2ccccc2)cc1)S(N)(=O)=O]

1-Biphenyl-3-yl-3-hydroxy-3-methylbutane-2-sulfonamide

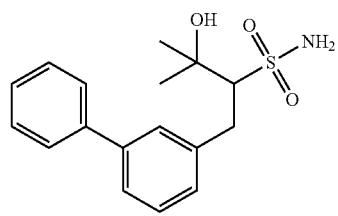 [SMILES: CC(C)(O)C(Cc1cccc(-c2ccccc2)c1)S(N)(=O)=O]

3-Hydroxy-3-methyl-1-phenylbutane-2-sulfonamide

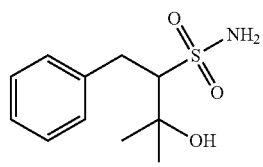 [SMILES: CC(C)(O)C(Cc1ccccc1)S(N)(=O)=O]

1-(4-Chlorophenyl)-3-hydroxy-3-methylbutane-2-sulfonamide

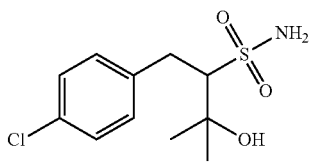 [SMILES: CC(C)(O)C(Cc1ccc(Cl)cc1)S(N)(=O)=O]

3-Hydroxy-3-methyl-1-naphthalen-1-ylbutane-2-sulfonamide

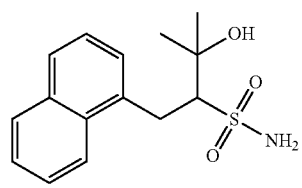 [SMILES: CC(C)(O)C(Cc1cccc2ccccc12)S(N)(=O)=O]

1-(6-Chloropyridin-3-yl)-3-hydroxy-3-methylbutane-2-sulfonamide

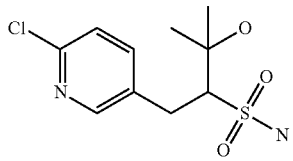 [SMILES: CC(C)(O)C(Cc1ccc(Cl)nc1)S(N)(=O)=O]

1-[6-(4-tert-Butylpiperazin-1-yl)pyridin-3-yl]-3-hydroxy-3-methylbutane-2-sulfonamide

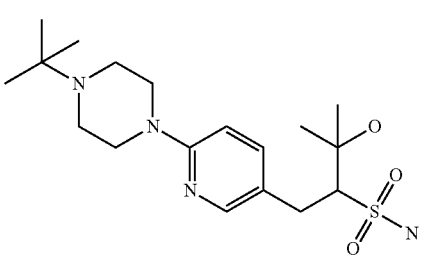 [SMILES: CC(C)(O)C(Cc1ccc(N2CCN(C(C)(C)C)CC2)nc1)S(N)(=O)=O]

2-Methoxy-6,6-dimethyl-5-[4-(5-trifluoromethyl-pyridin-2-yl)-benzyl]-5,6-dihydro[1,4,3]oxathiazine 4,4-dioxide

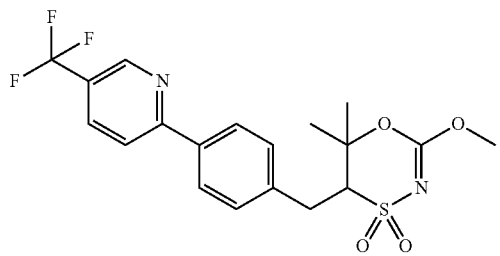 [SMILES: COC1=NS(=O)(=O)C(Cc2ccc(-c3ccc(C(F)(F)F)cn3)cc2)C(C)(C)O1]

A solution of 3-hydroxy-3-methyl-1-[4-(5-trifluoromethylpyridin-2-yl)phenyl]butane-2-sulfonamide (0.29 g) in acetic acid (1 ml) and tetramethyl orthocarbonate (5 g) was heated to 100° C. under an argon stream for five hours. In the course of this, methanol which formed was removed from the mixture. Subsequently, the solution was taken up with diatomaceous earth and purified by chromatography (ethyl acetate/heptane). This gave the product (0.085 g) with a molecular weight of 428.4 g/mol ($C_{19}H_{19}F_3N_2O_4S$), MS (ESI): (M+H+) 429 g/mol.

The following compounds were prepared in the same way:
5-Biphenyl-4-ylmethyl-2-methoxy-6,6-dimethyl-5,6-dihydro-[1,4,3]oxathiazine 4,4-dioxide

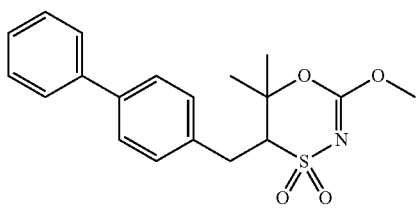 [SMILES: COC1=NS(=O)(=O)C(Cc2ccc(-c3ccccc3)cc2)C(C)(C)O1]

Biphenyl-3-ylmethyl-2-methoxy-6,6-dimethyl-5,6-dihydro-[1,4,3]oxathiazine 4,4-dioxide

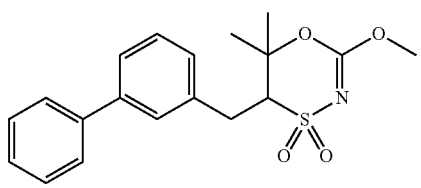 [SMILES: COC1=NS(=O)(=O)C(Cc2cccc(-c3ccccc3)c2)C(C)(C)O1]

2-Methoxy-6,6-dimethyl-5-naphthalen-1-ylmethyl-5,6-dihydro-[1,4,3]oxathiazine 4,4-dioxide

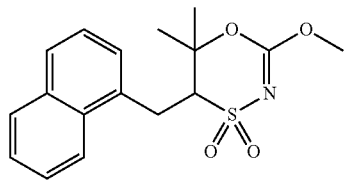 [SMILES: COC1=NS(=O)(=O)C(Cc2cccc3ccccc23)C(C)(C)O1]

5-(6-Chloropyridin-3-ylmethyl)-2-methoxy-6,6-dimethyl-5,6-dihydro-[1,4,3]oxathiazine 4,4-dioxide

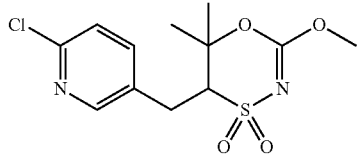 [SMILES: COC1=NS(=O)(=O)C(Cc2ccc(Cl)nc2)C(C)(C)O1]

5-[6-(4-tert-Butylpiperazin-1-yl)pyridin-3-ylmethyl]-2-methoxy-6,6-dimethyl-5,6-dihydro-[1,4,3]oxathiazine 4,4-dioxide

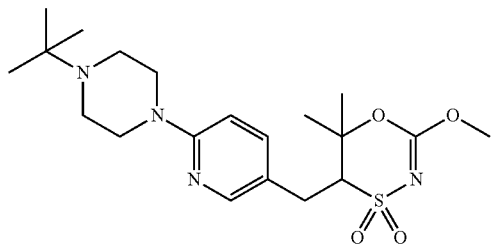 [SMILES: COC1=NS(=O)(=O)C(Cc2ccc(N3CCN(C(C)(C)C)CC3)nc2)C(C)(C)O1]

[(S)-3-(tert-Butyldimethylsilanyloxy)-1-(2-fluorophenyl) propyl]-[5,6,6-trimethyl-4,4-dioxo-5-(4-pyridin-2-ylbenzyl)-5,6-dihydro-4H-4lambda6-[1,4,3]oxathiazin-2-yl] amine

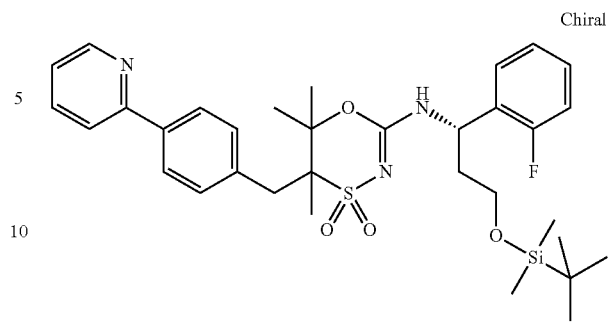

To a solution of pyridine-2-boronic acid (0.028 g) and $Cs_2CO_3$ (0.17 g) in degassed toluene/water (2.1 ml/0.9 ml) was [5-(4-bromobenzyl)-6,6-dimethyl-4,4-dioxo-5,6-dihydro-4H-4lambda6-[1,4,3]oxathiazin-2-yl]-[(S)-3-(tert-butyldimethylsilanyloxy)-1-(2-fluorophenyl)propyl]amine (0.11 g) and bis(benzylideneacetone)palladium (0.001 g) heated to 80° C. for six hours. After cooling, semiconcentrated sodium hydrogencarbonate solution (5 ml) was added and the suspension was extracted with ethyl acetate (3×20 ml). The organic solution was dried ($Na_2SO_4$), filtered and concentrated. The mixture was used further without further workup.

The following compounds were prepared in the same way:
[(S)-3-(tert-Butyldimethylsilanyloxy)-1-(2-fluorophenyl) propyl]-{5,6,6-trimethyl-4,4-dioxo-5-[4-(5-trifluoromethylpyridin-2-yl)benzyl]-5,6-dihydro-4H-4lambda6-[1,4,3]oxathiazin-2-yl}amine

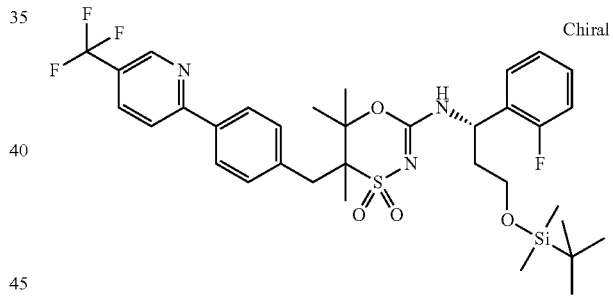

(S)-3-(2-Fluorophenyl)-3-[5,6,6-trimethyl-4,4-dioxo-5-(4-pyridin-2-ylbenzyl)-5,6-dihydro-4H-4lambda6-[1,4,3] oxathiazin-2-ylamino]propan-1-ol

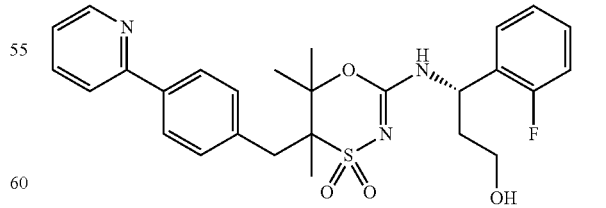

[(S)-3-(tert-Butyldimethylsilanyloxy)-1-(2-fluorophenyl) propyl]-[5,6,6-trimethyl-4,4-dioxo-5-(4-pyridin-2-yl-benzyl)-5,6-dihydro-4H-4lambda6-[1,4,3]oxathiazin-2-yl] amine (0.11 mg) was taken up in methanol (3 ml), concentrated hydrochloric acid (0.3 ml) was added and the mixture was stirred for one hour. Purification was effected from the solution by preparative HPLC. This gave the product (0.007 g) with a molecular weight of 511.6 g/mol ($C_{25}H_{29}FN_2O_4S$), MS (ESI): (M+H+) 512 g/mol.

The following compounds were prepared in the same way:

(S)-3-(2-Fluorophenyl)-3-{5,6,6-trimethyl-4,4-dioxo-5-[4-(5-trifluoromethylpyridin-2-yl)benzyl]-5,6-dihydro-4H-4lambda6-[1,4,3]oxathiazin-2-ylamino}propan-1-ol

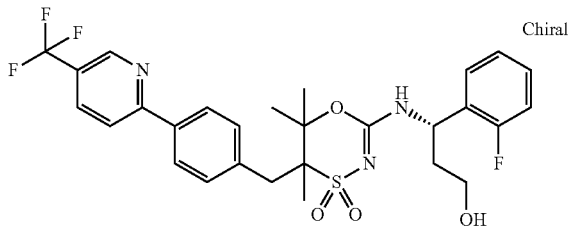 [SMILES: CC1(C)OC(N[C@@H](CCO)c2ccccc2F)=NS(=O)(=O)C1(C)Cc1ccc(-c2ccc(C(F)(F)F)cn2)cc1]

(S)-3-(5-Benzyl-6,6-dimethyl-4,4-dioxo-5,6-dihydro-4H-4lambda6-[1,4,3]oxathiazin-2-ylamino)-3-phenylpropan-1-ol

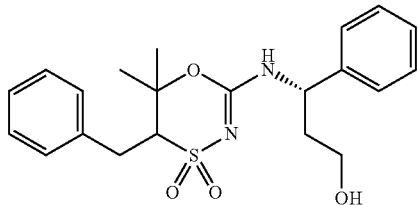 [SMILES: CC1(C)OC(N[C@@H](CCO)c2ccccc2)=NS(=O)(=O)C1Cc1ccccc1]

A solution of (S)-3-(tert-butyldimethylsilanyloxy)-1-phenylpropylamine (0.301 g) in dichloromethane (8 ml) was admixed with 1,1'-thiocarbonyldiimidazole (0.234 mg). After twenty minutes at room temperature, diethyl ether (10 ml) and n-pentane (10 ml) were added, and the mixture was washed with water (20 ml), dried ($Na_2SO_4$), filtered and concentrated under reduced pressure. The residue was dissolved in NMP (5 ml), and 3-hydroxy-3-methyl-1-phenylbutane-2-sulfonamide (0.24 g) dissolved in NMP (4 ml) was added. Then 2N sodium bistrimethylsilylamide (0.296 ml) was added and the mixture was stirred for one hour. Subsequently, N-bromosuccinimide (0.105 g) was added and the mixture was stirred for a further hour. The mixture was admixed with water (80 ml) and extracted with ethyl acetate (3×50 ml). The combined organic phases were washed once again with saturated sodium chloride solution (50 ml), dried ($Na_2SO_4$), filtered and concentrated. The residue was purified by preparative HPLC. This gave the product (0.063 g) with a molecular weight of 402.5 g/mol ($C_{21}H_{26}N_2O_4S$), MS (ESI): (M+H+) 403 g/mol.

The following compounds were prepared in the same way:

(S)-3-[5-(4-Chlorobenzyl)-6,6-dimethyl-4,4-dioxo-5,6-dihydro-4H-4lambda6-[1,4,3]oxathiazin-2-ylamino]-3-phenylpropan-1-ol

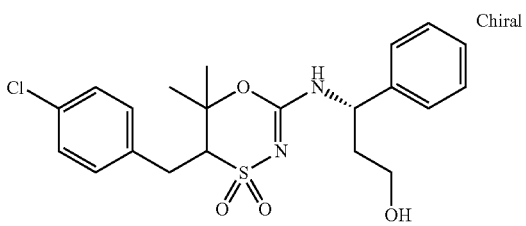 [SMILES: CC1(C)OC(N[C@@H](CCO)c2ccccc2)=NS(=O)(=O)C1Cc1ccc(Cl)cc1]

4-(4-{2-[(S)-3-(tert-Butyldimethylsilanyloxy)-1-(2-fluorophenyl)propylamino]-6,6-dim ethyl-4,4-dioxo-5,6-dihydro-4H-4lambda6-[1,4,3]oxathiazin-5-ylmethyl}phenyl)-3,6-dihydro-2H-pyridine-1-carboxylic acid tert-butyl ester

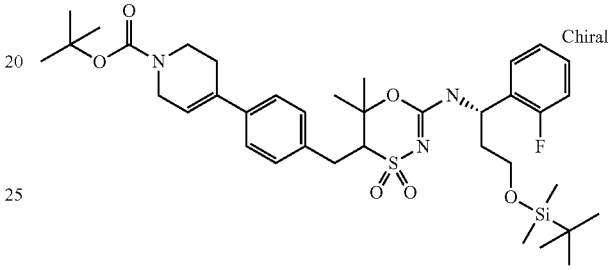

A solution of [5-(4-bromobenzyl)-6,6-dimethyl-4,4-dioxo-5,6-dihydro-4H-4lambda6-[1,4,3]oxathiazin-2-yl]-[(S)-3-(tert-butyldimethylsilanyloxy)-1-(2-fluorophenyl)propyl]amine (2.42 g), 4-(4,4,5,5-tetramethyl-[1,3,2]dioxaborolan-2-yl)-3,6-dihydro-2H-pyridine-1-carboxylic acid tert-butyl ester (1.49 g) and $Cs_2CO_3$ (2.57 g) in dioxane/water (30 ml/10 ml) was degassed with argon for 20 minutes. Subsequently, bis(dibenzylideneacetone)palladium(II) (0.23 g) and CTC-Q-Phos (0.56 g) were added and the mixture was stirred at 70° C. for 30 minutes. Subsequently, water (100 ml) was added and the aqueous emulsion was extracted with ethyl acetate (3×50 ml). The organic phase was then dried ($Na_2SO_4$), filtered and concentrated. The residue was purified by normal phase chromatography (1:4 ethyl acetate/heptane). This gave the product (2.08 g) with a molecular weight of 716 g/mol ($C_{37}H_{54}FN_3O_6SSi$), MS (ESI): (M+H+) 716 g/mol The following compounds were prepared in the same way:

4-(4-{2-[(S)-1-(2-Fluorophenyl)ethylamino]-6,6-dimethyl-4,4-dioxo-5,6-dihydro-4H-4lambda6-[1,4,3]oxathiazin-5-ylmethyl}phenyl)-3,6-dihydro-2H-pyridine-1-carboxylic acid tert-butyl ester

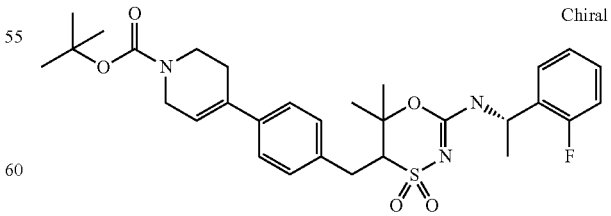

5-{2-[(S)-1-(2-Fluorophenyl)ethylamino]-6,6-dimethyl-4,4-dioxo-5,6-dihydro-4H-4lambda6-[1,4,3]oxathiazin-5-ylmethyl}-3',6'-dihydro-2'H-[2,4]bipyridinyl-1'-carboxylic acid tert-butyl ester

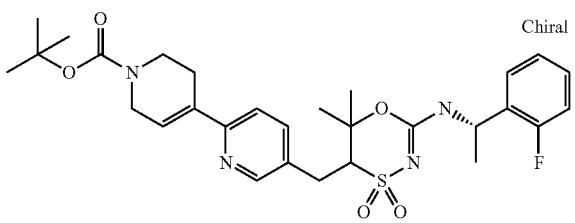 [SMILES: C[C@H](NC1=NS(=O)(=O)C(Cc2ccc(C3=CCN(C(=O)OC(C)(C)C)CC3)nc2)C(C)(C)O1)c1ccccc1F]

4-(4-{2-[(S)-1-(2-Chlorophenyl)ethylamino]-6,6-dimethyl-4,4-dioxo-5,6-dihydro-4H-4lambda6-[1,4,3]oxathiazin-5-ylmethyl}phenyl)-3,6-dihydro-2H-pyridine-1-carboxylic acid tert-butyl ester

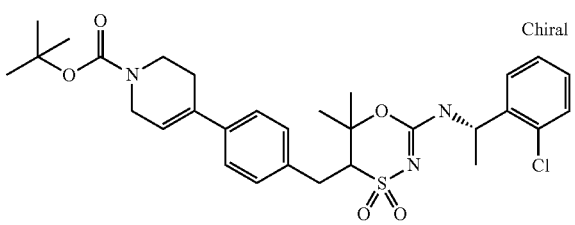 [SMILES: C[C@H](NC1=NS(=O)(=O)C(Cc2ccc(C3=CCN(C(=O)OC(C)(C)C)CC3)cc2)C(C)(C)O1)c1ccccc1Cl]

4-(4-{2-[(S)-3-(tert-Butyldimethylsilanyloxy)-1-(2-fluorophenyl)propylamino]-6,6-dimethyl-4,4-dioxo-5,6-dihydro-4H-4lambda6-[1,4,3]oxathiazin-5-ylmethyl}phenyl)piperidine-1-carboxylic acid tert-butyl ester

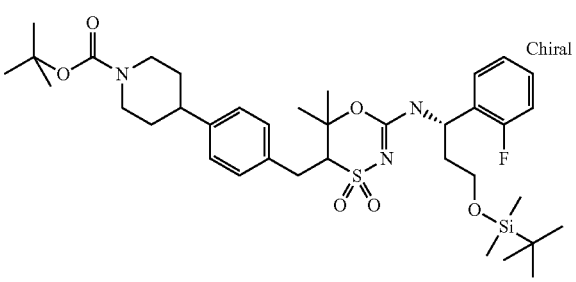 [SMILES: CC(C)(C)OC(=O)N1CCC(c2ccc(CC3C(C)(C)OC(N[C@@H](CCO[Si](C)(C)C(C)(C)C)c4ccccc4F)=NS3(=O)=O)cc2)CC1]

4-(4-{2-[(S)-3-(tert-Butyldimethylsilanyloxy)-1-(2-fluorophenyl)propylamino]-6,6-dimethyl-4,4-dioxo-5,6-dihydro-4H-4lambda6-[1,4,3]oxathiazin-5-ylmethyl}phenyl)-3,6-dihydro-2H-pyridine-1-carboxylic acid tert-butyl ester (1.8 g) was dissolved in ethanol, palladium on activated carbon was added and the mixture was stirred under a hydrogen atmosphere for two hours. The suspension was filtered and concentrated under reduced pressure. The residue was used further without further workup. This gave the product (1.8 g) with a molecular weight of 718 g/mol ($C_{37}H_{56}FN_3O_6SSi$), MS (ESI): (M+H+) 718 g/mol.

The following compounds were prepared in the same way:

4-(4-{2-[(S)-1-(2-Fluorophenyl)ethylamino]-6,6-dimethyl-4,4-dioxo-5,6-dihydro-4H-4lambda6-[1,4,3]oxathiazin-5-ylmethyl}phenyl)piperidine-1-carboxylic acid tert-butyl ester

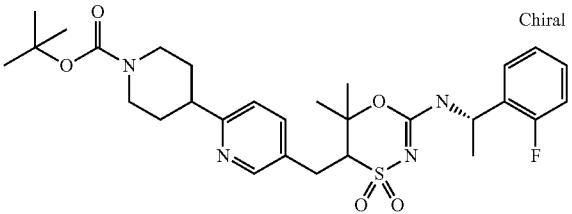 [SMILES: C[C@H](NC1=NS(=O)(=O)C(Cc2ccc(C3CCN(C(=O)OC(C)(C)C)CC3)nc2)C(C)(C)O1)c1ccccc1F]

5-{2-[(S)-1-(2-Fluorophenyl)ethylamino]-6,6-dimethyl-4,4-dioxo-5,6-dihydro-4H-4lambda6-[1,4,3]oxathiazin-5-ylmethyl}-3',4',5',6'-tetrahydro-2'H-[2,4']bipyridinyl-1'-carboxylic acid tert-butyl ester

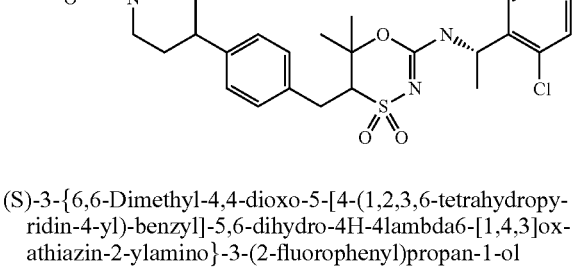

4-(4-{2-[(S)-1-(2-Chlorophenyl)ethylamino]-6,6-dimethyl-4,4-dioxo-5,6-dihydro-4H-4lambda6-[1,4,3]oxathiazin-5-ylmethyl}phenyl)piperidine-1-carboxylic acid tert-butyl ester (S)-3-{6,6-Dimethyl-4,4-dioxo-5-[4-(1,2,3,6-tetrahydropyridin-4-yl)-benzyl]-5,6-dihydro-4H-4lambda6-[1,4,3]oxathiazin-2-ylamino}-3-(2-fluorophenyl)propan-1-ol

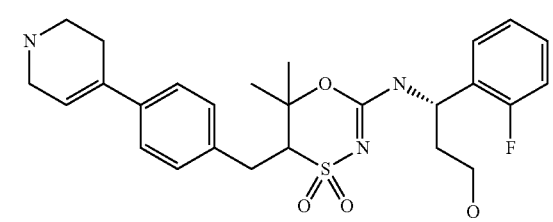

To a solution of 4-(4-{2-[(S)-3-(tert-butyldimethylsilanyloxy)-1-(2-fluorophenyl)propylamino]-6,6-dimethyl-4,4-dioxo-5,6-dihydro-4H-4lambda6-[1,4,3]oxathiazin-5-ylmethyl}phenyl)-3,6-dihydro-2H-pyridine-1-carboxylic acid tert-butyl ester (0.12 g) in methanol (2 ml) was added 37% hydrochloric acid (0.1 ml), and the mixture was stirred at room temperature overnight. The solution was then purified by preparative HPLC. This gave the product (0.085 g) with a molecular weight of 501 g/mol ($C_{26}H_{32}FN_3O_4S$), MS (ESI): (M+H+) 502 g/mol.

The following compound was prepared in the same way:
(S)-3-[6,6-Dimethyl-4,4-dioxo-5-(4-piperidin-4-ylbenzyl)-5,6-dihydro-4H-4lambda6-[1,4,3]oxathiazin-2-ylamino]-3-(2-fluorophenyl)propan-1-ol

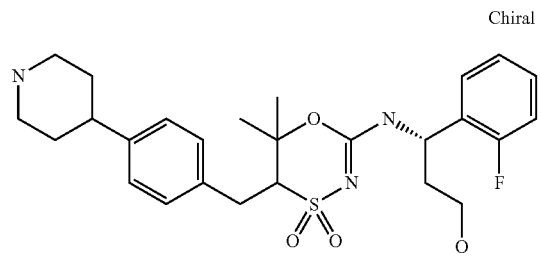 [SMILES: CC1(C)OC(N[C@@H](CCO)c2ccccc2F)=NS(=O)(=O)C1Cc1ccc(C2CCNCC2)cc1]

[6,6-Dimethyl-4,4-dioxo-5-(4-piperidin-4-yl-benzyl)-5,6-dihydro-4H-4lambda6-[1,4,3]oxathiazin-2-yl]-[(S)-1-(2-fluorophenyl)ethyl]amine

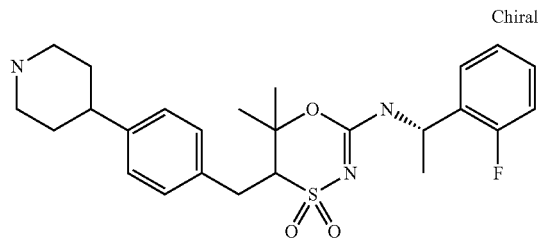 [SMILES: C[C@H](NC1=NS(=O)(=O)C(Cc2ccc(C3CCNCC3)cc2)C(C)(C)O1)c1ccccc1F]

[6,6-Dimethyl-4,4-dioxo-5-(4-piperidin-4-yl-benzyl)-5,6-dihydro-4H-4lambda6-[1,4,3]oxathiazin-2-yl]-[(S)-1-(2-chlorophenyl)ethyl]amine

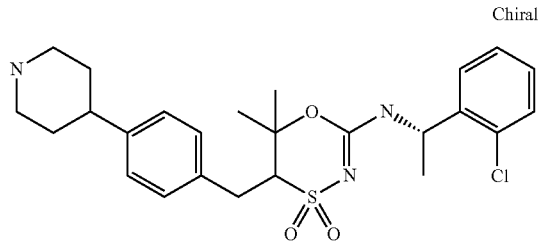 [SMILES: C[C@H](NC1=NS(=O)(=O)C(Cc2ccc(C3CCNCC3)cc2)C(C)(C)O1)c1ccccc1Cl]

[(R)-6,6-Dimethyl-4,4-dioxo-5-(4-piperazin-1-yl-benzyl)-5,6-dihydro-4H-4lambda6-[1,4,3]oxathiazin-2-yl]-[(S)-1-(2-fluorophenyl)ethyl]amine

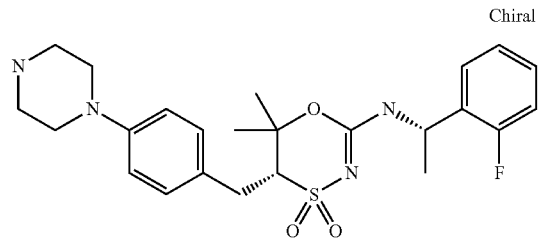 [SMILES: C[C@H](NC1=NS(=O)(=O)[C@H](Cc2ccc(N3CCNCC3)cc2)C(C)(C)O1)c1ccccc1F]

{5-[(R)-4-(2-Amino-2-methylpropoxy)benzyl]-6,6-dimethyl-4,4-dioxo-5,6-dihydro-4H-4lambda6-[1,4,3]oxathiazin-2-yl}-[(S)-1-(2-fluorophenyl)ethyl]amine

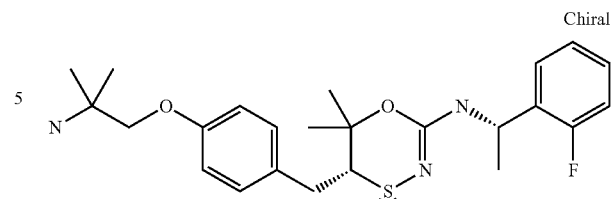

[(S)-1-(2-Fluorophenyl)ethyl]-5-(1',2',3',4',5',6'-hexahydro-[2,4']bipyridinyl-5-ylmethyl)-6,6-dimethyl-4,4-dioxo-5,6-dihydro-4H-4lambda6-[1,4,3]oxathiazin-2-yl]amine

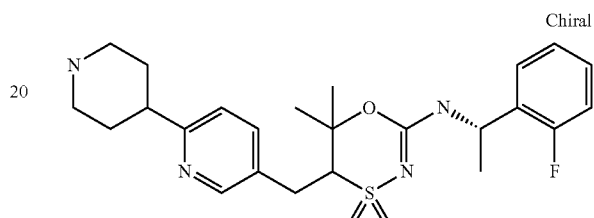

(S)-3-{6,6-Dimethyl-5-[4-(1-methyl-1,2,3,6-tetrahydropyridin-4-yl)benzyl]-4,4-dioxo-5,6-dihydro-4H-4lambda6-[1,4,3]oxathiazin-2-ylamino}-3-(2-fluorophenyl)propan-1-ol

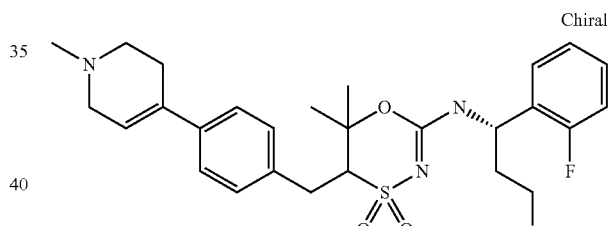

To a solution of (S)-3-{6,6-dimethyl-4,4-dioxo-5-[4-(1,2,3,6-tetrahydropyridin-4-yl)benzyl]-5,6-dihydro-4H-4lambda6-[1,4,3]oxathiazin-2-ylamino}-3-(2-fluorophenyl)propan-1-ol (0.07 g) in methanol (1 ml) were added paraformaldehyde (47 mg) and sodium cyanoborohydride (50 mg), and the mixture was heated under reflux for six hours. After cooling, the suspension was filtered. The methanol was removed under reduced pressure, and the residue was dissolved in ethyl acetate (50 ml) and extracted with 2N hydrochloric acid (2×30 ml). The acidic phase was then set to pH>13 with 2N NaOH and extracted with methylene chloride (2×30 ml). The organic solution was dried ($Na_2SO_4$), filtered and concentrated. This gave the product (0.085 g) with a molecular weight of 515 g/mol ($C_{27}H_{34}FN_3O_4S$), MS (ESI): (M+H+) 516 g/mol.

The following product was obtained in the same way:
(S)-3-{6,6-Dimethyl-5-[4-(1-methylpiperidin-4-yl)benzyl]-4,4-dioxo-5,6-dihydro-4H-4lambda6-[1,4,3]oxathiazin-2-ylamino}-3-(2-fluorophenyl)propan-1-ol

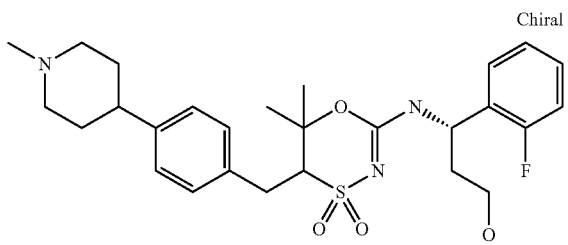 [SMILES: CN1CCC(c2ccc(CC3C(C)(C)OC(N[C@@H](CCO)c4ccccc4F)=NS3(=O)=O)cc2)CC1]

(S)-3-{(S)-6,6-Dimethyl-5-[4-(1-oxetan-3-ylpiperidin-4-yl)benzyl]-4,4-dioxo-5,6-dihydro-4H-4lambda6-[1,4,3]oxathiazin-2-ylamino}-3-(2-fluorophenyl)propan-1-ol

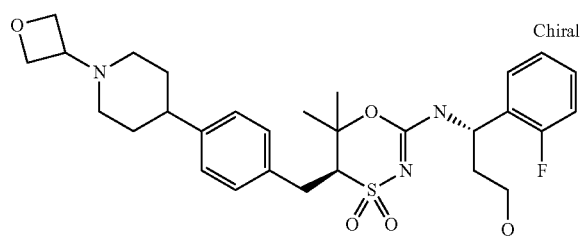 [SMILES: CC1(C)OC(N[C@@H](CCO)c2ccccc2F)=NS(=O)(=O)[C@H]1Cc1ccc(C2CCN(C3COC3)CC2)cc1]

{(S)-6,6-Dimethyl-5-[4-(1-oxetan-3-ylpiperidin-4-yl)benzyl]-4,4-dioxo-5,6-dihydro-4H-4lambda6-[1,4,3]oxathiazin-2-yl}-[(S)-1-(2-fluorophenyl)ethyl]amine

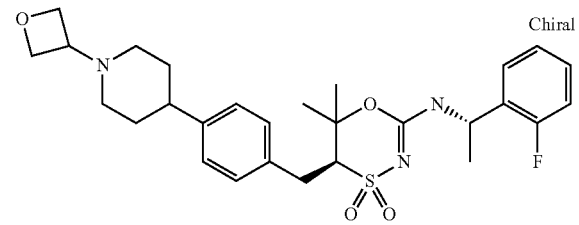 [SMILES: C[C@H](NC1=NS(=O)(=O)[C@@H](Cc2ccc(C3CCN(C4COC4)CC3)cc2)C(C)(C)O1)c1ccccc1F]

[6,6-Dimethyl-5-(1'-oxetan-3-yl-1',2',3',4',5',6'-hexahydro-[2,4]bipyridinyl-5-ylmethyl)-4,4-dioxo-5,6-dihydro-4H-4lambda6-[1,4,3]oxathiazin-2-yl]-[(S)-1-(2-fluorophenyl)ethyl]amine

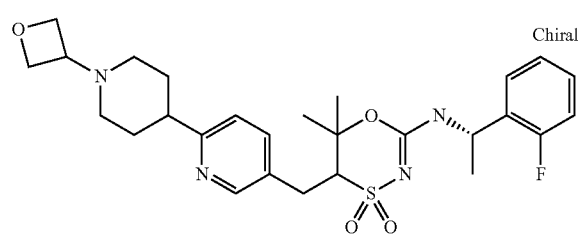 [SMILES: C[C@H](NC1=NS(=O)(=O)C(Cc2ccc(C3CCN(C4COC4)CC3)cc2)C(C)(C)O1)c1ccccc1Cl]

[(S)-1-(2-Chlorophenyl)ethyl]-6,6-dimethyl-5-[4-(1-oxetan-3-yl-piperidin-4-yl)benzyl]-4,4-dioxo-5,6-dihydro-4H-4lambda6-[1,4,3]oxathiazin-2-yl amine

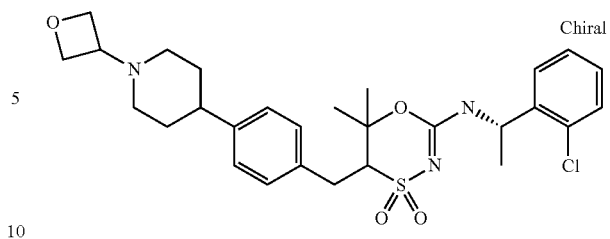

(S)-3-{5-[4-(1-Cyclopropylpiperidin-4-yl)benzyl]-6,6-dimethyl-4,4-dioxo-5,6-dihydro-4H-4lambda6-[1,4,3]oxathiazin-2-ylamino}-3-(2-fluorophenyl)propan-1-ol

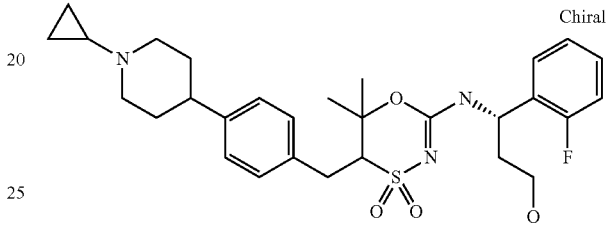

A solution of (S)-3-[6,6-dimethyl-4,4-dioxo-5-(4-piperidin-4-yl-benzyl)-5,6-dihydro-4H-4lambda6-[1,4,3]oxathiazin-2-ylamino]-3-(2-fluorophenyl)propan-1-ol (0.08 g), acetic acid (0.065 ml), sodium cyanoborohydride (0.01 g) and (1-ethoxycyclopropylmethyl)trimethylsilane (0.065 g) in DMF (1 ml) was stirred at 65° C. overnight. The suspension was admixed with water (20 ml) and set to pH>13. Subsequently, extraction was effected with methylene chloride (2×20 ml), and the organic phase was dried (Na$_2$SO$_4$), filtered and concentrated. The residue was purified by preparative HPLC. This gave the product (0.085 g) with a molecular weight of 543 g/mol (C$_{29}$H$_{38}$FN$_3$O$_4$S), MS (ESI): (M+H+) 544 g/mol.

The following products were obtained in the same way:

{5-[4-(1-Cyclopropylpiperidin-4-yl)benzyl]-6,6-dimethyl-4,4-dioxo-5,6-dihydro-4H-4lambda6-[1,4,3]oxathiazin-2-yl}-[(S)-1-(2-fluorophenyl)ethyl]amine

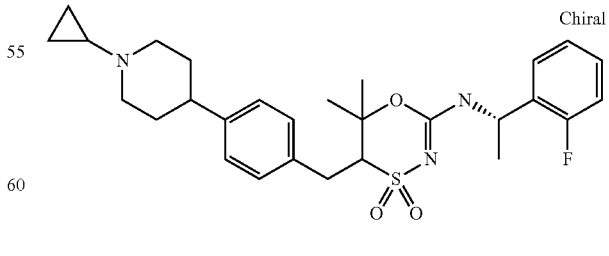

[5-(1'-Cyclopropyl-1',2',3',4',5',6'-hexahydro-[2,4]bipyridinyl-5-ylmethyl)-6,6-dimethyl-4,4-dioxo-5,6-dihydro-4H-4lambda6-[1,4,3]oxathiazin-2-yl]-[(S)-1-(2-fluorophenyl)ethyl]amine

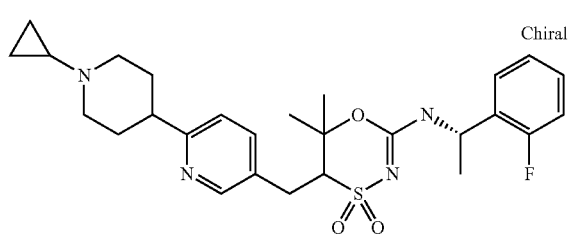 [SMILES: C[C@H](NC1=NS(=O)(=O)C(Cc2ccc(C3CCN(C4CC4)CC3)nc2)C(C)(C)O1)c1ccccc1F]

(S)-3-(2-Fluorophenyl)-3-(5-{4-[1-(2-hydroxyethyl)piperidin-4-yl]benzyl}-6,6-dimethyl-4,4-dioxo-5,6-dihydro-4H-4lambda6-[1,4,3]oxathiazin-2-ylamino)propan-1-ol

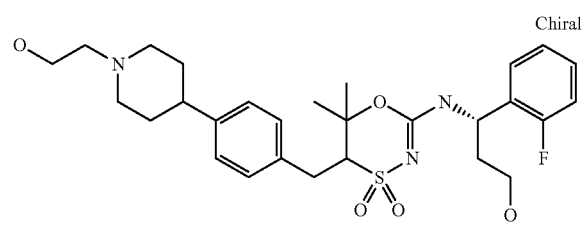 [SMILES: CC1(C)OC(N[C@@H](CCO)c2ccccc2F)=NS(=O)(=O)C1Cc1ccc(C2CCN(CCO)CC2)cc1]

To a solution of (S)-3-[6,6-dimethyl-4,4-dioxo-5-(4-piperidin-4-ylbenzyl)-5,6-dihydro-4H-4lambda6-[1,4,3]oxathiazin-2-ylamino]-3-(2-fluorophenyl)propan-1-ol (0.08 g) in DMF (1 ml) were added dropwise Hünig's base (0.065 ml) and 2-bromoethanol (0.013 ml), and then the mixture was stirred at 80° C. for 16 hours. After cooling, methylene chloride (20 ml) was added and the organic phase was extracted with 1N hydrochloric acid (2×20 ml). The aqueous phase was then set to pH>13 and extracted with methylene chloride. This gave the product (0.085 g) with a molecular weight of 547 g/mol ($C_{28}H_{38}FN_3O_5S$), MS (ESI): (M+H+) 548 g/mol.

The following products were obtained in the same way:

(S)-3-(2-Fluorophenyl)-3-(5-{4-[1-(3-hydroxypropyl)piperidin-4-yl]benzyl}-6,6-dimethyl-4,4-dioxo-5,6-dihydro-4H-4lambda6-[1,4,3]oxathiazin-2-ylamino)propan-1-ol

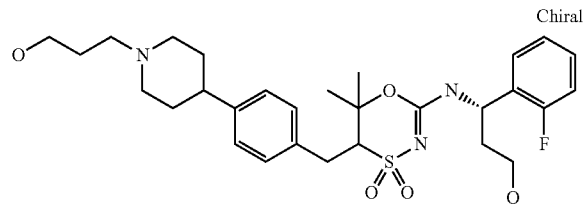 [SMILES: CC1(C)OC(N[C@@H](CCO)c2ccccc2F)=NS(=O)(=O)C1Cc1ccc(C2CCN(CCCO)CC2)cc1]

(S)-3-(6,6-Dimethyl-4,4-dioxo-5-{4-[1-(3,3,3-trifluoropropyl)piperidin-4-yl]benzyl}-5,6-dihydro-4H-4lambda6-[1,4,3]oxathiazin-2-ylamino)-3-(2-fluorophenyl)propan-1-ol

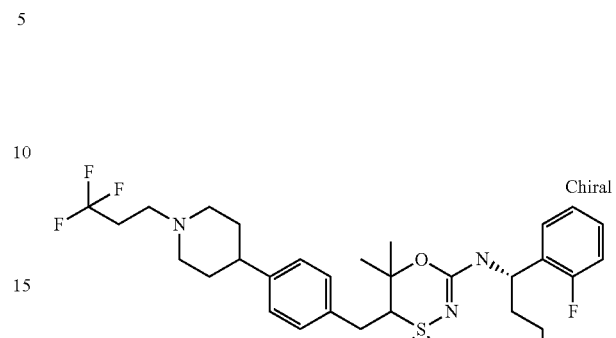

(S)-3-{5-[4-(1-Cyclopropylmethylpiperidin-4-yl)benzyl]-6,6-dimethyl-4,4-dioxo-5,6-dihydro-4H-4lambda6-[1,4,3]oxathiazin-2-ylamino}-3-(2-fluorophenyl)propan-1-ol

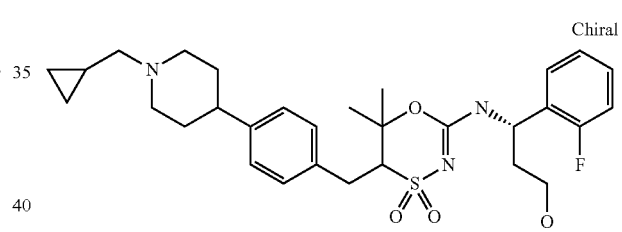

[3-(4-{2-[(S)-3-(tert-Butyldimethylsilanyloxy)-1-(2-fluorophenyl)propylamino]-6,6-dimethyl-4,4-dioxo-5,6-dihydro-4H-4lambda6-[1,4,3]oxathiazin-5-ylmethyl}phenyl)prop-2-ynyl]carbamic acid tert-butyl ester

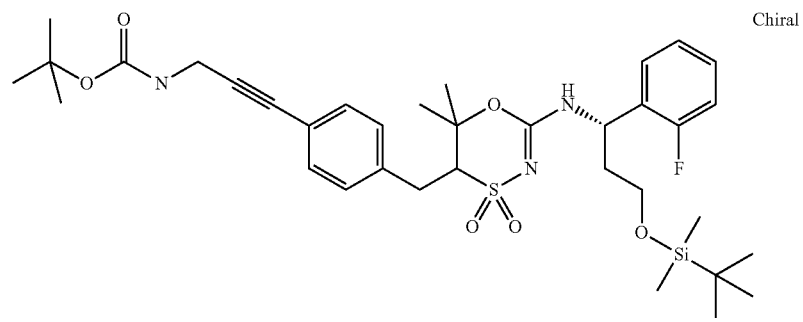 [SMILES: CC(C)(C)OC(=O)NCC#Cc1ccc(CC2C(C)(C)OC(N[C@@H](CCO[Si](C)(C)C(C)(C)C)c3ccccc3F)=NS2(=O)=O)cc1 ; "Chiral"]

To a suspension of bis(triphenylphosphine)palladium(II) dichloride (10 mg) and copper(I) iodide (5 mg) in dry dioxane (0.6 ml) were added successively triethylamine (120 μl) and a solution of [5-(4-bromobenzyl)-6,6-dimethyl-4,4-dioxo-5,6-dihydro-4H-4lambda6-[1,4,3]oxathiazin-2-yl]-[(S)-3-(tert-butyldimethylsilanyloxy)-1-(2-fluorophenyl)propyl]amine (100 mg) in dry dioxane (0.7 ml), and the mixture was stirred at 80° C. for 3 h and at 100° C. for 1 h. Subsequently, ethyl acetate was added and the mixture was washed with water. The organic phase was dried using a kieselguhr cartridge, filtered and concentrated under reduced pressure. This was followed by purification by column chromatography (ethyl acetate/heptane). This gave the product (79 mg) with a molecular weight of 687.9 g/mol ($C_{35}H_{50}FN_3O_6SSi$).

[3-(4-{2-[(S)-3-(tert-Butyldimethylsilanyloxy)-1-(2-fluorophenyl)propylamino]-6,6-dimethyl-4,4-dioxo-5,6-dihydro-4H-4lambda6-[1,4,3]oxathiazin-5-ylmethyl}phenyl)propyl]carbamic acid tert-butyl ester To a solution of [3-(4-{2-[(S)-3-(tert-butyldimethylsilanyloxy)-1-(2-fluorophenyl)propylamino]-6,6-dimethyl-4,4-dioxo-5,6-dihydro-4H-4lambda6-[1,4,3]oxathiazin-5-ylmethyl}phenyl)propyl]carbamic acid tert-butyl ester (45 mg) in methanol (2 ml) was added concentrated hydrochloric acid (0.2 ml), and the mixture was stirred for 2 days. The resulting mixture was purified in a purification laboratory by means of preparative HPLC. This gave the product (5 mg as the HCl salt after treatment with hydrochloric acid) with a molecular weight of 477.6 g/mol ($C_{23}H_{32}FN_3O_4S$); MS (ESI): m/e=478 (M+H+).

In an analogous manner, the following compounds were obtained:

(S)-3-{5-[4-(3-Dimethylaminopropyl)benzyl]-6,6-dimethyl-4,4-dioxo-5,6-dihydro-4H-4lambda6-[1,4,3]oxathiazin-2-ylamino}-3-(2-fluorophenyl)propan-1-ol

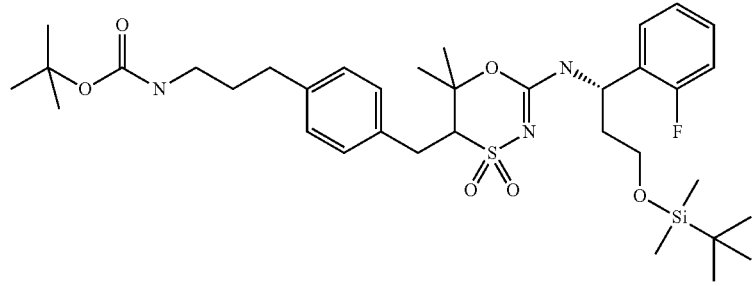

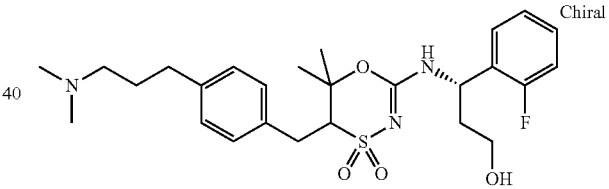

To a solution of [3-(4-{2-[(S)-3-(tert-butyldimethylsilanyloxy)-1-(2-fluorophenyl)propylamino]-6,6-dimethyl-4,4-dioxo-5,6-dihydro-4H-4lambda6-[1,4,3]oxathiazin-5-ylmethyl}phenyl)prop-2-ynyl]carbamic acid tert-butyl ester (79 mg) in methanol (25 ml) was added palladium on charcoal (5%, 25 mg) and the solution was stirred in a hydrogen atmosphere for 1 h. The mixture was filtered and the filtrate was concentrated. This was followed by purification by column chromatography (ethyl acetate/heptane). This gave the product (45 mg) with a molecular weight of 692.0 g/mol ($C_{35}H_{54}FN_3O_6SSi$).

(S)-3-{5-[4-(3-Aminopropyl)benzyl]-6,6-dimethyl-4,4-dioxo-5,6-dihydro-4H-4lambda6-[1,4,3]oxathiazin-2-ylamino}-3-(2-fluorophenyl)propan-1-ol (S)-3-{6,6-Dimethyl-5-[4-(3-morpholin-4-ylpropyl)benzyl]-4,4-dioxo-5,6-dihydro-4H-4lambda6-[1,4,3]oxathiazin-2-ylamino}-3-(2-fluorophenyl)propan-1-ol

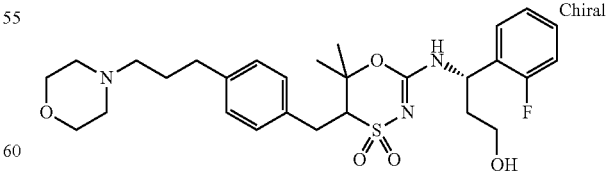

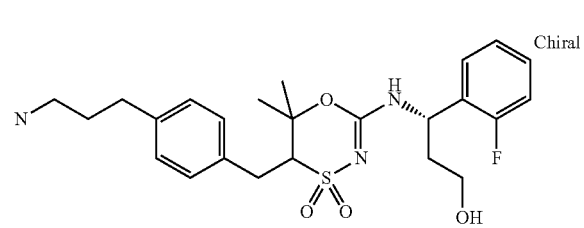

(S)-3-{6,6-Dimethyl-5-[4-(3-methylaminopropyl)benzyl]-4,4-dioxo-5,6-dihydro-4H-4lambda6-[1,4,3]oxathiazin-2-ylamino}-3-(2-fluorophenyl)propan-1-ol

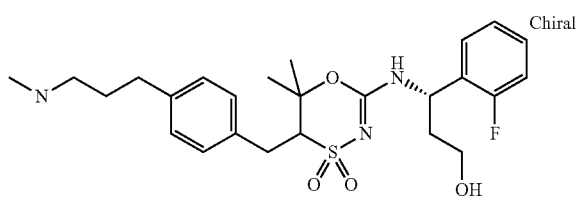

(S)-3-(2-Fluorophenyl)-3-[5-(4-{3-[(2-hydroxyethyl)methylamino]propyl}benzyl)-6,6-dimethyl-4,4-dioxo-5,6-dihydro-4H-4lambda6-[1,4,3]oxathiazin-2-ylamino]propan-1-ol

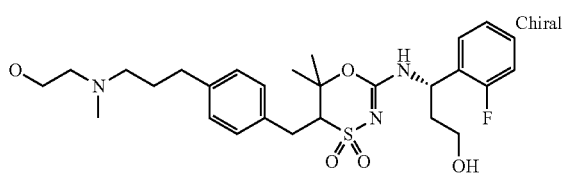

A solution of (S)-3-{6,6-dimethyl-5-[4-(3-methylaminopropyl)benzyl]-4,4-dioxo-5,6-dihydro-4H-4lambda6-[1,4,3]oxathiazin-2-ylamino}-(2-fluorophenyl)propan-1-ol (170 mg) and 2-bromoethanol (51 mg) in DMF (2.5 ml) was stirred at 50° C. for 8 h. The resulting mixture was purified in a purification laboratory by means of preparative HPLC. This gave the product (73 mg as the HCl salt after treatment with hydrochloric acid) with a molecular weight of 535.7 g/mol ($C_{27}H_{38}FN_3O_5S$); MS (ESI): m/e=536 (M+H$^+$).

In an analogous manner, the following compounds were obtained:

(S)-3-(2-Fluorophenyl)-3-(5-{4-[1-(2-methoxyethyl)piperidin-4-yl]benzyl}-6,6-dimethyl-4,4-dioxo-5,6-dihydro-4H-4lambda6-[1,4,3]oxathiazin-2-ylamino)propan-1-ol

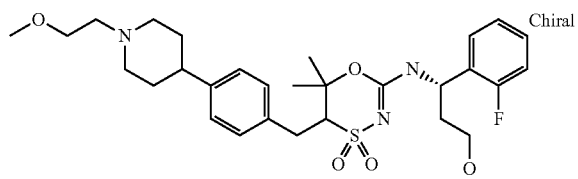

{6,6-Dimethyl-4,4-dioxo-5-[4-(4,4,5,5-tetramethyl-[1,3,2]dioxaborolan-2-yl)benzyl]-5,6-dihydro-4H-4lambda6-[1,4,3]oxathiazin-2-yl}-[(S)-1-(2-fluorophenyl)ethyl]amine

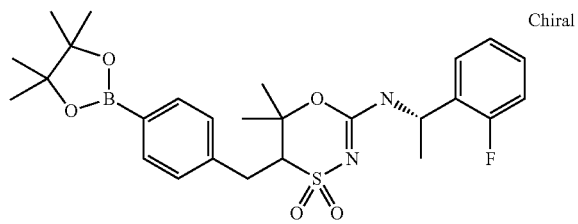

To a solution of [5-(4-bromobenzyl)-6,6-dimethyl-4,4-dioxo-5,6-dihydro-4H-4lambda6-[1,4,3]oxathiazin-2-yl]-[(S)-1-(2-fluorophenyl)ethyl]amine (470 mg) in dioxane were added Pd(dppf)Cl$_2$ (67 mg), bis(pinacolato)diboron (311 mg) and potassium acetate (241 mg), and the mixture was stirred at 80° C. for 1 h. After dilution with ethyl acetate, the mixture was washed with water and sodium chloride solution, dried over kieselguhr and concentrated. This was followed by purification by column chromatography (ethyl acetate/heptane). This gave the product (410 mg) with a molecular weight of 516.4 g/mol ($C_{26}H_{34}BFN_2O_5S$).

{6,6-Dimethyl-5-[4-(4-methylpiperazin-1-yl)benzyl]-4,4-dioxo-5,6-dihydro-4H-4lambda6-[1,4,3]oxathiazin-2-yl}-[(S)-1-(2-fluorophenyl)ethyl]amine

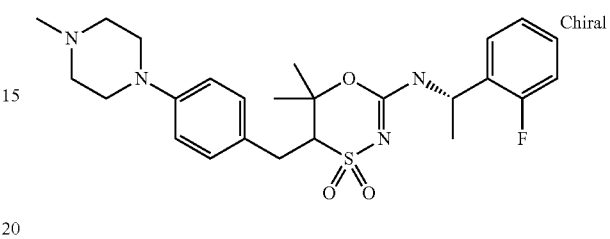

To a solution of {6,6-dimethyl-4,4-dioxo-5-[4-(4,4,5,5-tetramethyl-[1,3,2]dioxaborolan-2-yl)benzyl]-5,6-dihydro-4H-4lambda6-[1,4,3]oxathiazin-2-yl}-[(S)-1-(2-fluorophenyl)ethyl]amine (230 mg) in pyridine were added copper(11) acetate (76 mg) and 0.4 nm molecular sieve, and the mixture was stirred for 10 min. Subsequently, N-methylpiperazine (63 mg) was added and the mixture was stirred at 80° C. for 16 h. After dilution with ethyl acetate, the mixture was washed with sodium bicarbonate solution and sodium chloride solution, dried over magnesium sulfate and concentrated. The residue was purified in a purification laboratory by means of preparative HPLC. This gave the product (43 mg as the HCl salt after treatment with hydrochloric acid) with a molecular weight of 488.6 g/mol ($C_{25}H_{33}FN_4O_3S$); MS (ESI): m/e=489 (M+H$^+$).

In an analogous manner, the following compounds were obtained:

4-(4-{(R)-2-[(S)-1-(2-Fluorophenyl)ethylamino]-6,6-dimethyl-4,4-dioxo-5,6-dihydro-4H-4lambda6-[1,4,3]oxathiazin-5-ylmethyl}phenyl)piperazine-1-carbamic acid tert-butyl ester

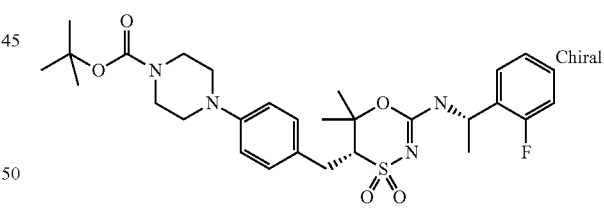

{(R)-5-[4-(4-tert-Butylpiperazin-1-yl)benzyl]-6,6-dimethyl-4,4-dioxo-5,6-dihydro-4H-4lambda6-[1,4,3]oxathiazin-2-yl}-[(S)-1-(2-fluorophenyl)ethyl]amine

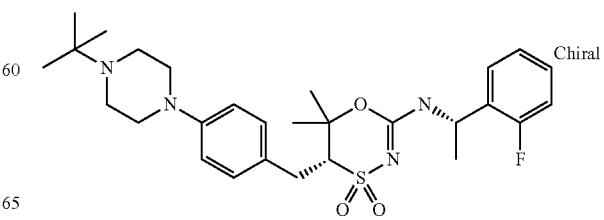

[2-(4-{(R)-2-[(S)-1-(2-Fluorophenyl)ethylamino]-6,6-dimethyl-4,4-dioxo-5,6-dihydro-4H-4lambda6-[1,4,3]oxathiazin-5-ylmethyl}phenoxy)-1,1-dimethylethyl]carbamic acid tert-butyl ester

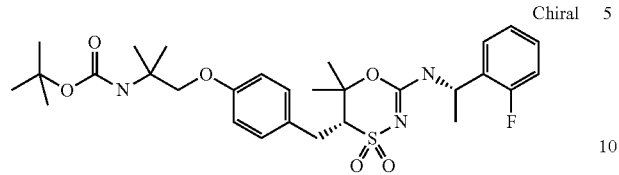

N-(4-{(R)-2-[(S)-1-(2-Fluorophenyl)ethylamino]-6,6-dimethyl-4,4-dioxo-5,6-dihydro-4H-4lambda6-[1,4,3]oxathiazin-5-ylmethyl}phenyl)-N',N'-dimethylethane-1,2-diamine

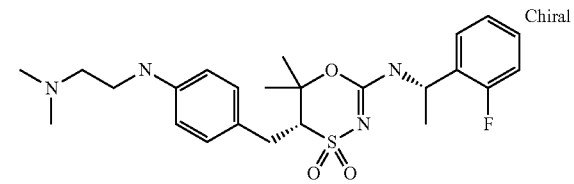

5-{2-[(S)-1-(2-Fluorophenyl)ethylamino]-6,6-dimethyl-4,4-dioxo-5,6-dihydro-4H-4lambda6-[1,4,3]oxathiazin-5-ylmethyl}-3',4',5',6'-tetrahydro-2'H-[2,4']bipyridinyl-1'-carboxylic acid methyl ester

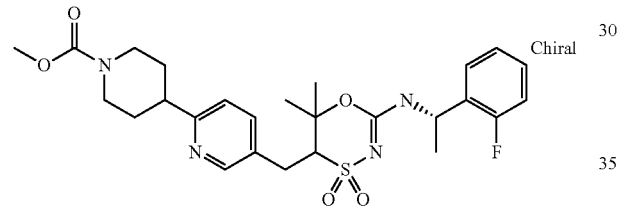

To [(S)-1-(2-fluorophenyl)ethyl]-[5-(1',2',3',4',5',6'-hexahydro-[2,4]bipyridinyl-5-ylmethyl)-6,6-dimethyl-4,4-dioxo-5,6-dihydro-4H-4lambda6-[1,4,3]oxathiazin-2-yl]amine (0.1 g) was added tetramethoxymethane (2 ml), and the mixture was heated to 100° C. for 2 hours. After dilution with ethyl acetate, the mixture was washed with sodium bicarbonate solution and sodium chloride solution, dried over magnesium sulfate and concentrated. The residue was purified in a purification laboratory by means of preparative HPLC. This gave the product (43 mg as the HCl salt after treatment with hydrochloric acid) with a molecular weight of 532.6 g/mol ($C_{26}H_{33}FN_4O_5S$); MS (ESI): m/e=533 (M+H$^+$).

The invention claimed is:
1. A compound of the formula I

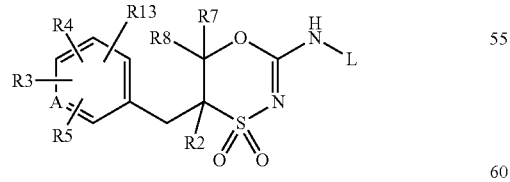

in which
A is CH, N;
L is R1, —CH(R10)(R11);
R10, R11 are each independently H, F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N(($C_1$-$C_6$)-alkyl)$_2$, COOH, COO—($C_1$-$C_6$)-alkyl, $CONH_2$, $CONH(C_1$-$C_6)$-alkyl, $CON(($C_1$-$C_6$)-alkyl)$_2$, $SF_5$, ($C_1$-$C_6$)-alkylene-(R6), ($C_3$-$C_8$)-cycloalkylene-(R6), ($C_1$-$C_6$)-alkylene-($C_3$-$C_8$)-cycloalkylene-(R6), ($C_6$-$C_8$)-aryl, ($C_1$-$C_6$)-alkylene-($C_6$-$C_{10}$)-aryl, —($C_6$-$C_{10}$)-heteroaryl, ($C_1$-$C_6$)-alkylene-($C_6$-$C_{10}$)-heteroaryl;
where the aryl radical or heteroaryl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N(($C_1$-$C_6$)-alkyl)$_2$, $SO_2$—$CH_3$, $SO_2$—$NH_2$, $SO_2$—$NH(C_1$-$C_6)$-alkyl, $SO_2$—$N(($C_1$-$C_6$)-alkyl)$_2$, COOH, COO—($C_1$-$C_6$)-alkyl, $CONH_2$, $CONH(C_1$-$C_6)$-alkyl, $CON(($C_1$-$C_6$)-alkyl)$_2$, $SF_5$;
R6 is H, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N(($C_1$-$C_6$)-alkyl)$_2$, $SO_2$—$CH_3$, $SO_2$—$NH_2$, $SO_2$—$NH(C_1$-$C_6)$-alkyl, $SO_2$—$N(($C_1$-$C_6$)-alkyl)$_2$, COOH, COO—($C_1$-$C_6$)-alkyl, $CONH_2$, $CONH(C_1$-$C_6)$-alkyl, $CON(($C_1$-$C_6$)-alkyl)$_2$, O—(CO)—$NH_2$, $SF_5$;
R1 is

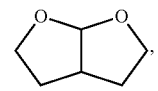

($C_6$-$C_{10}$)-aryl, ($C_3$-$C_8$)-cycloalkyl, ($C_3$-$C_8$)-carbocyclyl,
where the

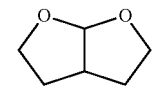

radical, aryl radical, cycloalkyl radical or carbocyclyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N(($C_1$-$C_6$)-alkyl)$_2$, $SO_2$—$CH_3$, $SO_2$—$NH_2$, $SO_2$—$NH(C_1$-$C_6)$-alkyl, $SO_2$—$N(($C_1$-$C_6$)-alkyl)$_2$, COOH, COO—($C_1$-$C_6$)-alkyl, $CONH_2$, $CONH(C_1$-$C_6)$-alkyl, $CON(($C_1$-$C_6$)-alkyl)$_2$, $SF_5$;
R2 is H, F, ($C_1$-$C_3$)-alkyl, where the alkyl radical may be mono- to trisubstituted by fluorine;
R3, R4, R5, R13 are each independently
H, F, Cl, Br, I, OH, $CF_3$, $CHF_2$, $CH_2F$, $NO_2$, CN, $OCF_3$, $OCHF_2$, —($C_1$-$C_6$)-alkylene-(R9), O—($C_1$-$C_6$)-alkylene-(R9), tert-butyl, isopropylene-(R9), (C=O)—($C_1$-$C_6$)-alkylene-(R9), ($C_1$-$C_6$)-alkylene-(R9), $NH_2$, $NH(C_1$-$C_6)$-alkylene-(R9), $N(($C_1$-$C_6$)-alkylene-R9)$_2$, ($C_1$-$C_6$)-alkylene-$NH_2$, ($C_1$-$C_6$)-alkylene-$NH(C_1$-$C_6)$-alkylene-(R9), ($C_1$-$C_6$)-alkylene-N(($C_1$-$C_6$)-alkylene-R9)$_2$, —O—($C_1$-$C_6$)-alkylene-$NH_2$, —O—($C_1$-$C_6$)-alkylene-$NH(C_1$-$C_6)$-alkylene-(R9), —O—($C_1$-$C_6$)-alkylene-N(($C_1$-$C_6$)-alkylene-R9)$_2$, —NH—($C_1$-$C_6$)-alkylene-$NH_2$, —NH—($C_1$-$C_6$)-alkylene-$NH(C_1$-$C_6)$-alkylene-(R9), —NH—($C_1$-$C_6$)-alkylene-N(($C_1$-$C_6$)-alkylene-R9)$_2$, $SO_2$—$CH_3$, $SO_2$—$NH_2$, $SO_2$—$NH(C_1$-$C_6)$-alkyl, $SO_2$—$N(($C_1$-$C_6$)-alkyl)$_2$, COOH, COO—($C_1$-$C_6$)-alkyl, $CONH_2$, $CONH(C_1$-$C_6)$-alkyl, $CON(($C_1$-$C_6$)-alkyl)$_2$, $SF_5$;

($C_6$-$C_{10}$)-aryl, —($C_1$-$C_6$)-alkylene-($C_6$-$C_{10}$)-aryl,
where the aryl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SO_2$—$CH_3$, $SO_2$—$NH_2$, $SO_2$—$NH(C_1$-$C_6)$-alkyl, $SO_2$—$N((C_1$-$C_6)$-alkyl)$_2$, COOH, COO—($C_1$-$C_6$)-alkyl, $CONH_2$, $CONH(C_1$-$C_6)$-alkyl, $CON((C_1$-$C_6)$-alkyl)$_2$, $SF_5$, ($C_6$-$C_{10}$)-aryl, ($C_3$-$C_8$)-cycloalkyl, 4 to 12-membered heterocycle;
where the ($C_6$-$C_{10}$)-aryl radical, ($C_3$-$C_8$)-cycloalkyl radical, 4 to 12-membered heterocycle radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SO_2$—$CH_3$, $SO_2$—$NH_2$, $SO_2$—$NH(C_1$-$C_6)$-alkyl, $SO_2$—$N((C_1$-$C_6)$-alkyl)$_2$, COOH, COO—($C_1$-$C_6$)-alkyl, $CONH_2$, $CONH(C_1$-$C_6)$-alkyl, $CON((C_1$-$C_6)$-alkyl)$_2$, $SF_5$;
4 to 12-membered heterocycle, —($C_1$-$C_6$)-alkylene-4 to 12-membered heterocycle,
where the heterocyclyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkylene-(R9), ($C_1$-$C_6$)-alkylene-(R9), $NH_2$, $NH(C_1$-$C_6)$-alkylene-(R9), $N((C_1$-$C_6)$-alkyl)$_2$, $SO_2$—($C_1$-$C_6$)-alkylene-(R9), $SO_2$—$C_2H_2F_3$, $SO_2$—$CH_3$, $SO_2$—$NH_2$, $SO_2$—NH($C_1$-$C_6$)-alkylene-(R9), $SO_2$—$N((C_1$-$C_6)$-alkyl)$_2$, COOH, COO—($C_1$-$C_6$)-alkylene-(R9), $CONH_2$, $CONH(C_1$-$C_6)$-alkylene-(R9), $CON((C_1$-$C_6)$-alkyl)$_2$, $SF_5$, ($C_6$-$C_{10}$)-aryl, ($C_3$-$C_8$)-cycloalkyl, 4 to 12-membered heterocycle;
where the ($C_6$-$C_{10}$)-aryl radical, ($C_3$-$C_8$)-cycloalkyl radical, 4 to 12-membered heterocycle radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SO_2$—$CH_3$, $SO_2$—$NH_2$, $SO_2$—$NH(C_1$-$C_6)$-alkyl, $SO_2$—$N((C_1$-$C_6)$-alkyl)$_2$, COOH, COO—($C_1$-$C_6$)-alkyl, $CONH_2$, $CONH(C_1$-$C_6)$-alkyl, $CON((C_1$-$C_6)$-alkyl)$_2$, $SF_5$;
or R4 and R5 together form a —CH=CH—CH=CH— chain;
R7, R8 are each independently H, mono- or poly-fluorine-substituted ($C_1$-$C_3$)-alkyl, or R7 and R8 together with the carbon atom to which they are bonded form a 3-8-membered carbocycle or heterocycle;
R9 is H, OH, $OCH_3$, $OCF_3$, $CHF_2$, $CF_3$;
and pharmaceutically acceptable salts thereof.

2. The compound of claim 1, wherein
A is CH, N;
L is R1, —CH(R10)(R11);
R10, R11 are each independently H, F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_{1-C_6})$-alkyl)$_2$, COOH, COO—($C_1$-$C_6$)-alkyl, $CONH_2$, $CONH(C_1$-$C_6)$-alkyl, $CON((C_1$-$C_6)$-alkyl)$_2$, $SF_5$, ($C_{1-C_6}$)-alkylene-(R6), ($C_3$-$C_8$)-cycloalkylene-(R6), ($C_1$-$C_6$)-alkylene-($C_3$-$C_8$)-cycloalkylene-(R6), ($C_6$-$C_{10}$)-aryl, ($C_1$-$C_6$)-alkylene-($C_6$-$C_{10}$)-aryl, —($C_6$-$C_{10}$)-heteroaryl, ($C_1$-$C_6$)-alkylene-($C_6$-$C_{10}$-heteroaryl;
where the aryl radical or heteroaryl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SO_2$—$CH_3$, $SO_2$—$NH_2$, $SO_2$—NH($C_1$-$C_6$)-alkyl, $SO_2$—$N((C_1$-$C_6)$-alkyl)$_2$, COOH, COO—($C_1$-$C_6$)-alkyl, $CONH_2$, $CONH(C_1$-$C_6)$-alkyl, $CON((C_1$-$C_6)$-alkyl)$_2$, $SF_5$;
R6 is H, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SO_2$—$CH_3$, $SO_2$—$NH_2$, $SO_2$—$NH(C_1$-$C_6)$-alkyl, $SO_2$—N (($C_1$-$C_6$)-alkyl)$_2$, COOH, COO—($C_1$-$C_6$)-alkyl, $CONH_2$, $CONH(C_1$-$C_6)$-alkyl, $CON((C_1$-$C_6)$-alkyl)$_2$, O—(CO)—$NH_2$, $SF_5$;
R1 is ($C_6$-$C_{10}$)-aryl, ($C_3$-$C_8$)-cycloalkyl, ($C_3$-$C_8$)-carbocyclyl,
where the aryl radical, cycloalkyl radical or carbocyclyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SO_2$—$CH_3$, $SO_2$—$NH_2$, $SO_2$—$NH(C_1$-$C_6)$-alkyl, $SO_2$—$N((C_1$-$C_6)$-alkyl)$_2$, COOH, COO—($C_1$-$C_6$)-alkyl, $CONH_2$, $CONH(C_1$-$C_6)$-alkyl, $CON((C_1$-$C_6)$-alkyl)$_2$, $SF_5$;
R2 is H, F, ($C_1$-$C_3$)-alkyl, where the alkyl radical may be mono- to trisubstituted by fluorine;
R3, R4, R5, R13 are each independently
H, F, Cl, Br, I, OH, $CF_3$, $CHF_2$, $CH_2F$, $NO_2$, CN, $OCF_3$, $OCHF_2$, —($C_1$-$C_6$)-alkylene-(R9), O—($C_1$-$C_6$)-alkylene-(R9), tert-butyl, isopropylene-(R9), (C=O)—($C_1$-$C_6$)-alkylene-(R9), ($C_1$-$C_6$)-alkylene-(R9), $NH_2$, $NH(C_1$-$C_6)$-alkylene-(R9), $N((C_1$-$C_6)$-alkylene-R9)$_2$, ($C_1$-$C_6$)-alkylene-$NH_2$, ($C_1$-$C_6$)-alkylene-$NH(C_1$-$C_6)$-alkylene-(R9), ($C_1$-$C_6$)-alkylene-$N((C_1$-$C_6)$-alkylene-R9)$_2$, —O—($C_1$-$C_6$)-alkylene-$NH_2$, —O—($C_1$-$C_6$)-alkylene-$NH(C_1$-$C_6)$-alkylene-(R9), —O—($C_1$-$C_6$)-alkylene-$N((C_1$-$C_6)$-alkylene-R9)$_2$, —NH—($C_1$-$C_6$)-alkylene-$NH_2$, —NH—($C_1$-$C_6$)-alkylene-$NH(C_1$-$C_6)$-alkylene-(R9), —NH—($C_1$-$C_6$)-alkylene-$N((C_1$-$C_6)$-alkylene-R9)$_2$, $SO_2$—$CH_3$, $SO_2$—$NH_2$, $SO_2$—$NH(C_1$-$C_6)$-alkyl, $SO_2$—$N((C_1$-$C_6)$-alkyl)$_2$, COOH, COO—($C_1$-$C_6$)-alkyl, $CONH_2$, $CONH(C_1$-$C_6)$-alkyl, $CON((C_1$-$C_6)$-alkyl)$_2$, $SF_5$;
phenyl,
where the phenyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SO_2$—$CH_3$, $SO_2$—$NH_2$, $SO_2$—$NH(C_1$-$C_6)$-alkyl, $SO_2$—$N((C_1$-$C_6)$-alkyl)$_2$, COOH, COO—($C_1$-$C_6$)-alkyl, $CONH_2$, $CONH(C_1$-$C_6)$-alkyl, $CON((C_1$-$C_6)$-alkyl)$_2$, $SF_5$, ($C_6$-$C_{10}$)-aryl, ($C_3$-$C_8$)-cycloalkyl, 4 to 12-membered heterocycle;
where the ($C_6$-$C_{10}$)-aryl radical, ($C_3$-$C_8$)-cycloalkyl radical, 4 to 12-membered heterocycle radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SO_2$—$CH_3$, $SO_2$—$NH_2$, $SO_2$—$NH(C_1$-$C_6)$-alkyl, $SO_2$—$N((C_1$-$C_6)$-alkyl)$_2$, COOH, COO—($C_1$-$C_6$)-alkyl, $CONH_2$, $CONH(C_1$-$C_6)$-alkyl, $CON((C_1$-$C_6)$-alkyl)$_2$, $SF_5$;
4 to 12-membered heterocycle, —($C_1$-$C_6$)-alkylene-4 to 12-membered heterocycle,
where the heterocyclyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkylene-(R9), ($C_1$-$C_6$)-alkylene-(R9), $NH_2$, $NH(C_1$-$C_6)$-alkylene-(R9), $N((C_1$-$C_6)$-alkyl)$_2$, $SO_2$—($C_1$-$C_6$)-alkylene-(R9), $SO_2$—$C_2H_2F_3$, $SO_2$—$CH_3$, $SO_2$—$NH_2$, $SO_2$—NH ($C_1$-$C_6$)-alkylene-(R9), $SO_2$—N(($C_1$-$C_6$)-alkyl)$_2$, COOH, COO—($C_1$-$C_6$)-alkylene-(R9), $CONH_2$, CONH($C_1$-$C_6$)-alkylene-(R9), CON(($C_1$-$C_6$)-alkyl)$_2$, $SF_5$, ($C_6$-$C_{10}$)-aryl, ($C_3$-$C_8$)-cycloalkyl, 4 to 12-membered heterocycle;
  where the ($C_6$-$C_{10}$)-aryl radical, ($C_3$-$C_8$)-cycloalkyl radical, 4 to 12-membered heterocycle radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$;
or R4 and R5 together form a —CH=CH—CH=CH— chain;
R7, R8 are each independently ($C_1$-$C_3$)-alkyl;
R9 is H, OH, $OCH_3$, $OCF_3$, $CHF_2$, $CF_3$;
and pharmaceutically acceptable salts thereof.

3. The compound of claim 1, wherein
A is CH, N;
L is R1, —CH(R10)(R11);
R10, R11 are each independently ($C_1$-$C_6$)-alkyl, ($C_1$-$C_6$)-alkylene-(R6), ($C_6$-$C_{10}$)-aryl, —($C_6$-$C_{10}$)-heteroaryl;
  where the aryl radical or heteroaryl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$;
R6 is H, OH, O—(CO)—$NH_2$, $SO_2NH_2$;
R1 is ($C_3$-$C_8$)-cycloalkyl, ($C_3$-$C_8$)-carbocyclyl,
  where the cycloalkyl radical or carbocyclyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$;
R2 is H, F, ($C_1$-$C_3$)-alkyl, where the alkyl radical may be mono- to trisubstituted by fluorine;
R3 is F, Cl, Br, I, OH, $CF_3$, $CHF_2$, $CH_2F$, $NO_2$, CN, $OCF_3$, $OCHF_2$, —($C_1$-$C_6$)-alkylene-(R9), O—($C_1$-$C_6$)-alkylene-(R9), tert-butyl, isopropylene-(R9), (C=O)—($C_1$-$C_6$)-alkylene-(R9), ($C_1$-$C_6$)-alkylene-(R9), $NH_2$, NH($C_1$-$C_6$)-alkylene-(R9), N(($C_1$-$C_6$)-alkylene-R9)$_2$, ($C_1$-$C_6$)-alkylene-$NH_2$, ($C_1$-$C_6$)-alkylene-NH($C_1$-$C_6$)-alkylene-(R9), ($C_1$-$C_6$)-alkylene-N(($C_1$-$C_6$)-alkylene-R9)$_2$, —O—($C_1$-$C_6$)-alkylene-$NH_2$, —O—($C_1$-$C_6$)-alkylene-NH($C_1$-$C_6$)-alkylene-(R9), —O—($C_1$-$C_6$)-alkylene-N(($C_1$-$C_6$)-alkylene-R9)$_2$, —NH—($C_1$-$C_6$)-alkylene-$NH_2$, —NH—($C_1$-$C_6$)-alkylene-NH($C_1$-$C_6$)-alkylene-(R9), —NH—($C_1$-$C_6$)-alkylene-N(($C_1$-$C_6$)-alkylene-R9)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$;
phenyl,
  where the phenyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$, ($C_6$-$C_{10}$)-aryl, ($C_3$-$C_8$)-cycloalkyl, 4 to 12-membered heterocycle;
  where the ($C_6$-$C_{10}$)-aryl radical, ($C_3$-$C_8$)-cycloalkyl radical, 4 to 12-membered heterocycle radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_o$)-alkyl, $CONH_2$, CONH($C_1$-$C_6$)-alkyl, CON(($C_1$-$C_6$)-alkyl)$_2$, $SF_5$;
4 to 12-membered heterocycle, —($C_1$-$C_6$)-alkylene-4 to 12-membered heterocycle, where the heterocyclyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkylene-(R9), ($C_1$-$C_6$)-alkylene-(R9), $NH_2$, NH($C_1$-$C_6$)-alkylene-(R9), N(($C_1$-$C_6$)-alkyl)$_2$, $SO_2$—($C_1$-$C_6$)-alkylene-(R9), $SO_2$—$C_2H_2F_3$, $SO_2$—$CH_3$, $SO_2$—$NH_2$, $SO_2$—NH($C_1$-$C_6$)-alkylene-(R9), $SO_2$—N(($C_1$-$C_6$)-alkyl)$_2$, COOH, COO—($C_1$-$C_6$)-alkylene-(R9), $CONH_2$, CONH($C_1$-$C_6$)-alkylene-(R9), CON(($C_1$-$C_6$)-alkyl)$_2$, $SF_5$, ($C_6$-$C_{10}$)-aryl, ($C_3$-$C_8$)-cycloalkyl, 4 to 12-membered heterocycle;
  where the ($C_6$-$C_{10}$)-aryl radical, ($C_3$-$C_8$)-cycloalkyl radical, 4 to 12-membered heterocycle radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$;
R4, R5, R13 are each independently
H, F, Cl, Br, I, OH, $CF_3$, $NO_2$, CN, $OCF_3$, —($C_1$-$C_6$)-alkylene-(R9), O—($C_1$-$C_6$)-alkylene-(R9), $NH_2$;
R7, R8 are each independently ($C_1$-$C_3$)-alkyl;
R9 is H, OH, $OCH_3$, $OCF_3$, $CHF_2$, $CF_3$;
and pharmaceutically acceptable salts thereof.

4. The compound of claim 1, wherein
A is CH, N;
L is R1, —CH(R10)(R11);
R10 is ($C_1$-$C_6$)-alkyl, ($C_1$-$C_6$)-alkylene-(R6);
R11 is ($C_6$-$C_{10}$)-aryl;
  where the aryl radical or heteroaryl radical may be mono- to trisubstituted by F, Cl, Br, ($C_1$-$C_6$)-alkyl;
R6 is OH;
R1 is 2,2,2-bicyclooctyl,
  where the 2,2,2-bicyclooctyl radical may be mono- to trisubstituted by F, Cl, Br;
R2 is H, ($C_1$-$C_3$)-alkyl;
R3 is F, Cl, Br, I, OH, $CF_3$, $CHF_2$, $CH_2F$, $NO_2$, CN, $OCF_3$, $OCHF_2$, —($C_1$-$C_6$)-alkylene-(R9), O—($C_1$-$C_6$)-alkylene-(R9), tert-butyl, isopropylene-(R9), (C=O)—($C_1$-$C_6$)-alkylene-(R9), ($C_1$-$C_6$)-alkylene-(R9), $NH_2$, NH($C_1$C_6$)-alkylene-(R9), N(($C_1$-$C_6$)-alkylene-R9)$_2$, ($C_1$-$C_6$)-alkylene-$NH_2$, ($C_1$-$C_6$)-alkylene-NH($C_1$-$C_6$)-alkylene-(R9), ($C_1$-$C_6$)-alkylene-N(($C_1$-$C_6$)-alkylene-R9)$_2$, —O—($C_1$-$C_6$)-alkylene-$NH_2$, —O—($C_1$-$C_6$)-alkylene-NH($C_1$-$C_6$)-alkylene-(R9), —O—($C_1$-$C_6$)-alkylene-N(($C_1$-$C_6$)-alkylene-R9)$_2$, —NH—($C_1$-$C_6$)-alkylene-$NH_2$, —NH—($C_1$-$C_6$)-alkylene-NH($C_1$-$C_6$)-alkylene-(R9), —NH—($C_1$-$C_6$)-alkylene-N(($C_1$-$C_6$)-alkylene-R9)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$;

phenyl,
where the phenyl radical may be mono- to trisubstituted by F, Cl, Br, I, OH, $CF_3$, $CHF_2$, $CH_2F$, $NO_2$, CN, $OCF_3$, $OCHF_2$, O—$(C_1$-$C_6)$-alkyl, $(C_1$-$C_6)$-alkyl, $NH_2$, $NH(C_1$-$C_6)$-alkyl, $N((C_1$-$C_6)$-alkyl$)_2$, $SO_2$—$CH_3$, $SO_2$—$NH_2$, $SO_2$—$NH(C_1$-$C_6)$-alkyl, $SO_2$—$N((C_1$-$C_6)$-alkyl$)_2$, COOH, COO—$(C_1$-$C_6)$-alkyl, $CONH_2$, $CONH(C_1$-$C_6)$-alkyl, CON$((C_1$-$C_6)$-alkyl$)_2$, $SF_5$;

pyridine, tetrahydropyridine, piperidine, morpholine, piperazine,
where the pyridine, tetrahydropyridine, piperidine, morpholine or piperazine radical may be mono- to trisubstituted by F, Cl, Br, I, OH, $CF_3$, $CHF_2$, $CH_2F$, $NO_2$, CN, $OCF_3$, $OCHF_2$, O—$(C_1$-$C_6)$-alkylene-(R9), $(C_1$-$C_6)$-alkylene-(R9), $NH_2$, $NH(C_1$-$C_6)$-alkylene-(R9), $N((C_1$-$C_6)$-alkyl$)_2$, $SO_2$—$(C_1$-$C_6)$-alkylene-(R9), $SO_2$—$C_2H_2F_3$, $SO_2$—$CH_3$, $SO_2$—$NH_2$, $SO_2$—$NH(C_1$-$C_6)$-alkylene-(R9), $SO_2$—N$((C_1$-$C_6)$-alkyl$)_2$, COOH, COO—$(C_1$-$C_6)$-alkylene-(R9), $CONH_2$, $CONH(C_1$-$C_6)$-alkylene-(R9), CON$((C_1$-$C_6)$-alkyl$)_2$, $SF_5$, $(C_6$-$C_{10})$-aryl, $(C_3$-$C_8)$-cycloalkyl, —$(C_1$-$C_6)$-alkylene-$(C_3$-$C_8)$-cycloalkyl, 4 to 12-membered heterocycle;

R4, R5, R13 are each independently
H, F, Cl, Br, I, OH, $CF_3$, $NO_2$, CN, $OCF_3$, —$(C_1$-$C_6)$-alkylene-(R9), O—$(C_1$-$C_6)$-alkylene-(R9), $NH_2$;

R7, R8 are each independently $(C_1$-$C_3)$-alkyl;
R9 is H, OH, $OCH_3$, $OCF_3$, $CHF_2$, $CF_3$;
and pharmaceutically acceptable salts thereof.

5. The compound of claim 1, wherein
A is CH, N;
L is R1, —CH(R10)(R11);
R10 is $(C_1$-$C_6)$-alkyl, $(C_1$-$C_6)$-alkylene-(R6);
R11 is $(C_6$-$C_{10})$-aryl;
where the aryl radical or heteroaryl radical may be mono- to trisubstituted by F, Cl, Br, $(C_1$-$C_6)$-alkyl;
R6 is OH;
R1 is 2,2,2-bicyclooctyl,
where the 2,2,2-bicyclooctyl radical may be mono- to trisubstituted by F, Cl, Br;
R2 is H, $(C_1$-$C_3)$-alkyl;
R3 is F, Cl, Br, I, OH, $CF_3$, $CHF_2$, $CH_2F$, $NO_2$, CN, $OCF_3$, $OCHF_2$, —$(C_1$-$C_6)$-alkylene-(R9), O—$(C_1$-$C_6)$-alkylene-(R9), tert-butyl, isopropylene-(R9), (C=O)—$(C_1$-$C_6)$-alkylene-(R9), $(C_1$-$C_6)$-alkylene-(R9), $NH_2$, $NH(C_1$-$C_6)$-alkylene-(R9), $N((C_1$-$C_6)$-alkylene-R9$)_2$, $(C_1$-$C_6)$-alkylene-$NH_2$, $(C_1$-$C_6)$-alkylene-$NH(C_1$-$C_6)$-alkylene-(R9), $(C_1$-$C_6)$-alkylene-$N((C_1$-$C_6)$-alkylene-R9$)_2$, —O—$(C_1$-$C_6)$-alkylene-$NH_2$, -O—$(C_1$-$C_6)$-alkylene-$NH(C_1$-$C_6)$-alkylene-(R9), —O—$(C_1$-$C_6)$-alkylene-$N((C_1$-$C_6)$-alkylene-R9$)_2$, —NH—$(C_1$-$C_6)$-alkylene-$NH_2$, —NH—$(C_1$-$C_6)$-alkylene-$NH(C_1$-$C_6)$-alkylene-(R9), —NH—$(C_1$-$C_6)$-alkylene-$N((C_1$-$C_6)$-alkylene-R9$)_2$, $SO_2$—$CH_3$, $SO_2$—$NH_2$, $SO_2$—$NH(C_1$-$C_6)$-alkyl, $SO_2$—$N((C_1$-$C_6)$-alkyl$)_2$, COOH, COO—$(C_1$-$C_6)$-alkyl, $CONH_2$, $CONH(C_1$-$C_6)$-alkyl, CON$((C_1$-$C_6)$-alkyl$)_2$, $SF_5$;
phenyl,
where the phenyl radical may be mono- to trisubstituted by F, Cl, Br, $CF_3$;
pyridine, tetrahydropyridine, piperidine, morpholine, piperazine,
where the pyridine, tetrahydropyridine, piperidine, morpholine or piperazine radical may be mono- to trisubstituted by F, Cl, Br, $CF_3$, $(C_1$-$C_6)$-alkylene-(R9), COO—$(C_1$-$C_6)$-alkylene-(R9), $(C_3$-$C_8)$-cycloalkyl, oxetane;

R4, R5, R13 are each independently
H, F, Cl, Br, I, OH, $CF_3$, $NO_2$, CN, $OCF_3$, —$(C_1$-$C_6)$-alkylene-(R9), O—$(C_1$-$C_6)$-alkylene-(R9), $NH_2$;

R7, R8 are each independently $(C_1$-$C_3)$-alkyl;
R9 is H, OH, $OCH_3$, $OCF_3$, $CHF_2$, $CF_3$;
and pharmaceutically acceptable salts thereof.

6. A pharmaceutical composition comprising the compound of claim 1, or pharmaceutically acceptable salts thereof, and a pharmaceutically acceptable carrier and/or excipient.

7. The pharmaceutical composition of claim 6, further comprising at least one further active ingredient.

8. The pharmaceutical composition of claim 7, wherein said active ingredient is one or more antidiabetics, active hypoglycemic ingredients, HMG-CoA reductase inhibitors, cholesterol absorption inhibitors, PPAR gamma agonists, PPAR alpha agonists, PPAR alpha/gamma agonists, PPAR delta agonists, fibrates, MTP inhibitors, bile acid absorption inhibitors, CETP inhibitors, polymeric bile acid adsorbers, LDL receptor inducers, ACAT inhibitors, antioxidants, lipoprotein lipase inhibitors, ATP citrate lyase inhibitors, squalene synthetase inhibitors, lipoprotein(a) antagonists, HM74A receptor agonists, lipase inhibitors, insulins, sulfonylureas, biguanides, meglitinides, thiazolidinediones, α-glucosidase inhibitors, active ingredients which act on the ATP-dependent potassium channel of the beta cells, glycogen phosphorylase inhibitors, glucagon receptor antagonists, activators of glucokinase, inhibitors of gluconeogenesis, inhibitors of fructose 1,6-biphosphatase, modulators of glucose transporter 4, inhibitors of glutamine:fructose-6-phosphate amidotransferase, inhibitors of dipeptidylpeptidase IV, inhibitors of 11-beta-hydroxysteroid dehydrogenase 1, inhibitors of protein tyrosine phosphatase 1B, modulators of the sodium-dependent glucose transporter 1 or 2, GPR40 modulators, inhibitors of hormone-sensitive lipase, inhibitors of acetyl-CoA carboxylase, inhibitors of phosphoenolpyruvate carboxykinase, inhibitors of glycogen synthase kinase-3 beta, inhibitors of protein kinase C beta, endothelin-A receptor antagonists, inhibitors of I kappaB kinase, modulators of the glucocorticoid receptor, CART agonists, NPY agonists, MC4 agonists, orexin agonists, H3 agonists, TNF agonists, CRF agonists, CRF BP antagonists, urocortin agonists, β3 agonists, CB1 receptor antagonists, MSH (melanocyte-stimulating hormone) agonists, CCK agonists, serotonin reuptake inhibitors, mixed serotoninergic and noradrenergic compounds, 5HT agonists, bombesin agonists, galanin antagonists, growth hormones, growth hormone-releasing compounds, TRH agonists, decoupling protein 2 or 3 modulators, leptin agonists, DA agonists, lipase/amylase inhibitors, PPAR modulators, RXR modulators or TR β agonists or amphetamines.

9. A process for preparing a pharmaceutical composition comprising mixing the compound of claim 1 with a pharmaceutically suitable carrier and converting said mixture is to a form suitable for administration.

10. A method of treating hyperglycemia comprising administering to a patient in need thereof a therapeutically effective amount of the pharmaceutical composition of claim 6.

11. A method of treating diabetes comprising administering to a patient in need thereof a therapeutically effective amount of the pharmaceutical composition of claim 6.

12. A method of treating insulin resistance comprising administering to a patient in need thereof a therapeutically effective amount of the pharmaceutical composition of claim 6.

13. A kit consisting of separate packages of
a) an effective amount of the compound of claim 1 and
b) an effective amount of a further active medicament ingredient.

* * * * *